(12) United States Patent
Kabiri

(10) Patent No.: US 12,188,866 B2
(45) Date of Patent: Jan. 7, 2025

(54) DEVICES FOR BIOLOGICAL ANALYSIS

(71) Applicant: CELLSBIN, INC., Guilford, CT (US)

(72) Inventor: Ali Kabiri, Guilford, CT (US)

(73) Assignee: CELLSBIN, INC., Guilford, CT (US)

( * ) Notice: Subject to any disclaimer, the term of this patent is extended or adjusted under 35 U.S.C. 154(b) by 0 days.

(21) Appl. No.: 18/412,346

(22) Filed: Jan. 12, 2024

(65) Prior Publication Data

US 2024/0210317 A1    Jun. 27, 2024

Related U.S. Application Data

(63) Continuation of application No. PCT/US2023/027948, filed on Jul. 17, 2023.

(60) Provisional application No. 63/476,100, filed on Dec. 19, 2022, provisional application No. 63/368,773, filed on Jul. 18, 2022.

(51) Int. Cl.
| | | |
|---|---|---|
| *G01N 21/47* | (2006.01) | |
| *B01L 3/00* | (2006.01) | |
| *G06T 17/00* | (2006.01) | |

(52) U.S. Cl.
CPC .... *G01N 21/4788* (2013.01); *B01L 3/502715* (2013.01); *G06T 17/00* (2013.01); *G01N 2201/061* (2013.01)

(58) Field of Classification Search
CPC ......... G01N 21/4788; G01N 2201/061; G01N 15/14; G01N 15/02; G01N 21/47; G01N 33/49; G01N 33/574; G01N 33/58; B01L 3/502715; G06T 17/00
See application file for complete search history.

(56) References Cited

U.S. PATENT DOCUMENTS

| | | | | |
|---|---|---|---|---|
| 6,522,775 | B2 * | 2/2003 | Nelson | G01N 23/046 |
| | | | | 382/133 |
| 10,481,092 | B2 * | 11/2019 | Loock | G01J 3/4406 |
| 10,620,121 | B2 * | 4/2020 | Zheng | G01N 15/14 |

(Continued)

FOREIGN PATENT DOCUMENTS

| | | | |
|---|---|---|---|
| CN | 104266955 A | * | 1/2015 |
| EP | 4016124 A1 | | 6/2022 |
| WO | WO-2024019988 A1 | | 1/2024 |

OTHER PUBLICATIONS

Ahmed, et al., "Rotational Manipulation of Single Cells and Organisms Using Acoustic Waves", Natural Communications 2016, 7. ( Year: 2016).*

(Continued)

*Primary Examiner* — Edmond C Lau
*Assistant Examiner* — Jarreas C Underwood
(74) *Attorney, Agent, or Firm* — WILSON SONSINI GOODRICH & ROSATI

(57) ABSTRACT

One aspect provided herein is an analyte processing device, comprising one or more flow channels, wherein at least one flow channel of the one or more flow channels comprise an analyte processing area; one or more excitation sources in optical communication with the analyte processing area and comprising an optical path from the one or more excitation sources to the analyte processing area; and one or more photodetectors in optical communication with the analyte processing area, wherein the optical path comprises a light scattering control system.

19 Claims, 27 Drawing Sheets

(56) References Cited

U.S. PATENT DOCUMENTS

| | | | | |
|---|---|---|---|---|
| 2003/0199758 | A1* | 10/2003 | Nelson | G01N 21/4795 |
| | | | | 600/425 |
| 2009/0208072 | A1* | 8/2009 | Seibel | G01N 15/1436 |
| | | | | 382/128 |
| 2013/0222547 | A1* | 8/2013 | Van Rooyen | G02B 21/0004 |
| | | | | 438/57 |
| 2013/0242301 | A1* | 9/2013 | Berg | G01N 15/1434 |
| | | | | 356/336 |
| 2014/0206546 | A1* | 7/2014 | Chenchik | C12N 15/1072 |
| | | | | 506/14 |
| 2015/0006445 | A1* | 1/2015 | Benz | A61P 35/00 |
| | | | | 706/12 |
| 2016/0282264 | A1* | 9/2016 | Wagner | G01N 15/147 |
| 2017/0016060 | A1* | 1/2017 | Sabounchi | B01L 3/502707 |
| 2017/0316487 | A1* | 11/2017 | Mazed | G06Q 30/0241 |
| 2018/0043687 | A1* | 2/2018 | Govyadinov | B41J 2/125 |
| 2018/0106782 | A1* | 4/2018 | Pruitt | C09K 11/06 |
| 2019/0239753 | A1* | 8/2019 | Wentz | G01J 3/2803 |
| 2020/0033514 | A1* | 1/2020 | Meng | G01J 3/10 |
| 2020/0206740 | A1* | 7/2020 | Chiu | G01N 15/1459 |
| 2021/0126025 | A1* | 4/2021 | Kennedy | H01L 27/1464 |
| 2021/0162414 | A1* | 6/2021 | Liu | B01L 3/502761 |
| 2021/0239590 | A1* | 8/2021 | Kwok | G01N 15/1429 |
| 2021/0331161 | A1* | 10/2021 | Meng | G02B 6/34 |
| 2022/0155229 | A1* | 5/2022 | Rothberg | H01L 27/14812 |
| | | | | 250/361 R |
| 2022/0163429 | A1* | 5/2022 | Qasaimeh | C12M 35/02 |
| 2022/0187430 | A1* | 6/2022 | Kulesh | G01S 7/4863 |
| 2022/0356461 | A1* | 11/2022 | Shendure | C12N 15/1093 |
| 2023/0045152 | A1* | 2/2023 | Saliu | G06T 7/70 |
| 2023/0174970 | A1* | 6/2023 | Alvarez | G01N 15/1429 |
| | | | | 506/4 |

OTHER PUBLICATIONS

An et al., Measuring cell deformation by microfluidics. Front Bioeng Biotechnol. 11:1214544, pp. 1-16 (2023).

Descamps et al., Microfluidic-based technologies for CTC isolation: A review of 10 years of intense efforts towards liquid biopsy. Int J Mol Sci. 23(4):1981, pp. 1-39 (2022).

Eroles et al., Advances in mechanical biomarkers. J Mol Recognit. 36(8):e3022, pp. 1-24 (2023).

Geddes, Metal-enhanced fluorescence. Phys. Chem. Chem. Phys. 15:19537, 1page (2013).

Gnyawali et al., Simultaneous acoustic and photoacoustic microfluidic flow cytometry for label-free analysis. Sci Rep. 9(1):1585, pp. 1-11 (2019).

Kang et al., Dynamical machine learning volumetric reconstruction of objects' interiors from limited angular views. Light Sci Appl. 10(1):74, pp. 1-21 (2021).

Mancuso et al., Stretching of red blood cells at high strain rates. Phys Rev Fluids 2(10):101101(R), pp. 1-7 (2017). Available at https://link.aps.org/accepted/10.1103/PhysRevFluids.2.101101.

Meinhardt et al., Trackformer: Multi-object tracking with transformers. Proceedings of the IEEE/CVF Conference on Computer Vision and Pattern Recognition (CVPR) pp. 8844-8854; (2022).

Obi et al., The design and synthesis of circular RNAs. Methods. 196:85-103 (2021).

PCT/US2023/027948 International Search Report and Written Opinion dated Nov. 23, 2023.

Plochowietz et al., Stable end-sealed DNA as robust nano-rulers for in vivo single-molecule fluorescence. Chem Sci. 7(7):4418-4422 (2016).

Ren et al., Entrapment of prostate cancer circulating tumor cells with a sequential size-based microfluidic chip. Anal. Chem. 90(12):7526-7534 (2018).

Renier et al., Label-free isolation of prostate circulating tumor cells using Vortex microfluidic technology. NPJ Precis Oncol. 1(1):15, pp. 1-15 (2017).

Rodenberg et al., Ptychography. Springer Handbook of Microscopy (Eds. Hawkes and Spence), (2019), 138 pages. Available at https://eprints.whiterose.ac.uk/127795.

Sung et al., Optical diffraction tomography for high resolution live cell imaging. Optics Express. 17(1):266-277 (2009).

Yeh et al., Speckle-structured illumination for 3D phase and fluorescence computational microscopy. Biomedical Optics Express. 10(7):3635-3653 (2019).

Yeo et al., Surface acoustic wave microfluidics. Annu Rev Fluid Mech. 46:379-406 (2014).

* cited by examiner

Measured optical signal of dyed microspheres via uncorrelated time lapse microscopy vs time correlated single photon counting Time lapse microscopy imaging optical signal quality Uncorrelated time lapse imaging optical signal quality False Positive = 6.5%

DEVICES FOR BIOLOGICAL ANALYSIS

CROSS-REFERENCE

This application is a continuation of International Application No. PCT/US2023/027948, filed Jul. 17, 2023, which claims the benefit of U.S. Provisional Application No. 63/368,773, filed on Jul. 18, 2022; and U.S. Provisional Application No. 63/476,100, filed on Dec. 19, 2022; the contents of each of which of which are incorporated by reference herein in their entireties.

BACKGROUND

Flow cytometry (FC) devices and systems can be used to characterize and analyze particles in fluid, e.g., physical and biochemical properties of cells and biochemical molecules or molecule clusters based on their optical responses as they are interrogated by external light sources in a serial manner. Optical signals from such particles can be collected by an optical detector, such as a photomultiplier tube (PMT), and are analyzed or processed to extract information carried by the optical properties of the particles. The optical signals from the particles can be caused by one or more interactions between the input light and the particles such as forward scattering (FSC), side scattering (SSC), and fluorescence. There is currently a gap between demand to characterize biological systems and the devices which are capable to perform such characterization.

SUMMARY

Efficient and favorable conditions for characterizing biological systems optically are valuable to human endeavors.

In some embodiments, provided herein is an analyte processing device, comprising: one or more flow channels, wherein at least one flow channel of the one or more flow channels comprise an analyte processing area; one or more excitation sources in optical communication with the analyte processing area and comprising an optical path from the one or more excitation sources to the analyte processing area; and one or more photodetectors in optical communication with the analyte processing area, wherein the optical path comprises a light scattering control system.

In some embodiments, provided herein is an analyte processing device, comprising: one or more flow channels, wherein at least one flow channel of the one or more flow channels comprise an analyte processing area; one or more excitation sources in optical communication with the analyte processing area and comprising an optical path from the one or more excitation sources to the analyte processing area; and one or more photodetectors in optical communication with the analyte processing area, wherein the optical path comprises a light scattering control system, wherein (i), (ii), (iii), or any combination thereof are integrated monothically, system-in-package, heterogeneously, three-dimensionally integrated, or a combination thereof. In some embodiments, the optical path is configured to yield an evanescent light beam from the one or more excitation sources. In some embodiments, the one or more flow channels comprise more than one analyte processing area. In some embodiments, the one or more excitation sources are integrated with the analyte processing device. In some embodiments, the one or more photodetectors are layered below the one or more flow channels. In some embodiments, the light scattering control system comprises an optical membrane comprising a polarizer, waveplate, absorber, filter, blocker, concentrator, reflector, or mirror. In some embodiments, the one or more photodetectors comprise a shutter configured to reduce overexposure of light. In some embodiments, the one or more photodetectors comprise a single photodetector pixel. In some embodiments, the one or more photodetector pixels are 10 microns by 10 microns in size. In some embodiments, the one or more photodetector pixels are 20 microns by 20 microns in size. In some embodiments, the one or more photodetector pixels are 20 microns by 10 microns in size. In some embodiments, the analyte processing device comprises two or more photodetectors, wherein the two or more photodetectors are positioned 20 microns apart from one another. In some embodiments, at least one of the one or more excitation sources is a reference excitation source. In some embodiments, the one or more excitation sources is integrated with the analyte processing device. In some embodiments, the one or more photodetectors is integrated with the analyte processing device. In some embodiments, the light scattering control system comprises a dichroic optical component configured to redirect scattered light distal from the one or more photodetectors. In some embodiments, the light scattering control system is configured to improve signal to noise ratio by at least a factor of five. In some embodiments, the filter is comprised of at least one layer of dielectric material configured to absorb unwanted light wavelengths and improve signal to noise ratio by a factor of at least five. In some embodiments, the filter is comprised of at least one layer of semiconductor material configured to absorb unwanted light wavelengths and improve signal to noise ratio by a factor of at least five. In some embodiments, the filter is comprised of at least one layer of metallic material configured to absorb unwanted light wavelengths and improve signal to noise ratio by a factor of at least five. In some embodiments, the filter is comprised of at least two layers of dielectric, semiconductor, or metallic material configured to absorb unwanted light wavelengths and improve signal to noise ratio by a factor of at least 5. In some embodiments, the blocker comprises a layer of absorptive material configured to transmit specific wavelengths. In some embodiments, the blocker is tuned to absorb specific photonic wavelength ranges. In some embodiments, the filter is comprised of at least two layers of dielectric, semiconductor, or metallic material configured to absorb unwanted light wavelengths and improve signal to noise ratio. In some embodiments, the filter is comprised of a polarizing light filter. In some embodiments, the blocker comprises a layer of absorptive material configured to transmit specific wavelengths of light. In some embodiments, the blocker is tuned to absorb specific photonic wavelength ranges. In some embodiments, the one or more photodetectors comprise a complementary metal oxide sensor (CMOS) imager. In some embodiments, the CMOS imager is configured to flush electrons generated with scattered light upon excitation. In some embodiments, the CMOS imager is spectral. In some embodiments, the CMOS imager is configured for photon intensity. In some embodiments, the CMOS imager is configured for photon wavelength. In some embodiments, the CMOS imager is a pinned photodiode. In some embodiments, the CMOS imager is a single photon avalanche diode array. In some embodiments, the CMOS imager comprises one or more arrays of single photon avalanche diodes. In some embodiments, the CMOS imager further comprises one or more event cameras. In some embodiments, the CMOS imager further comprises one or more time-delay integration (TDI) camera. In some embodiments, the one or more excitation sources further comprise a waveguide. In some embodiments, the one or more flow channels comprise multiple single inlets and a single outlet. In some embodiments, the one or more flow channels comprise multiple single inlets and a doublet outlet. In some embodiments, the one or more flow channels comprise a single inlet and multiple outlets. In some embodiments, the one or more excitation sources further comprise an interposer. In some embodiments, the one or more excitation sources further comprise a transducer. In some embodiments, the transducer is integrated into the chip. In some embodiments, the transducer is external to the chip. In some embodiments, the one or more excitation sources comprise one laser. In some embodiments, the one or more excitation sources comprises one or more light emitting diodes (LED). In some embodiments, the LED is a micro LED. In some embodiments, the one or more excitation sources comprise multiple lasers. In some embodiments, the one or more excitation sources comprise external lasers. In some embodiments, the one or more excitation sources comprise bonded lasers. In some embodiments, the one or more excitation sources comprise at least one continuous laser. In some embodiments, the one or more excitation sources comprise at least one pulsed laser. In some embodiments, the one or more excitation sources comprise at least one tunable laser. In some embodiments, the one or more excitation sources comprise at least one laser tuned to near IR to visible range wavelengths of light. In some embodiments, the concentrator is a microlens concentrator. In some embodiments, the concentrator comprises a flat lens concentrator. In some embodiments, the concentrator comprises a diffractive lens. In some embodiments, the concentrator comprises an absorptive lens. In some embodiments, the concentrator comprises a non-absorptive lens. In some embodiments, the concentrator comprises a polarization sensitive lens. In some embodiments, the concentrator comprises a dielectric. In some embodiments, the concentrator comprises a dielectric block. In some embodiments, the concentrator comprises a dielectric block at least 100 nanometers thick. In some embodiments, the concentrator comprises a dielectric block at least one micrometer thick. In some embodiments, the one or more excitation sources comprise an optical circuit comprising one or more light entry sections, one or more optical dividers, and a light delivery section. In some embodiments, the light delivery section further comprises one or more dichroic optical components configured to redirect scattered light away from the light delivery section. In some embodiments, the light entry section comprises vertical couplers. In some embodiments, the light entry section comprises optical grating. In some embodiments, the light entry section further comprises a lateral coupler. In some embodiments, the light entry section is a pinhole. In some embodiments, the reflector is configured to improve the coupling efficiency of the vertical couplers. In some embodiments, the mirror is configured to improve the coupling efficiency of vertical couplers. In some embodiments, the analyte processing area is located at a bottom surface of one or more flow channels. In some embodiments, the one or more flow channels is configured to generate a displacement effect on an analyte located in the at least one flow channel, thereby selectively displacing the analyte in the one or more analyte processing areas. In some embodiments, the displacement is acoustical. In some embodiments, the displacement is electrical. In some embodiments, the displacement is magnetic. In some embodiments, the displacement is caused by a fluid wave. In some embodiments, the displacement is caused by a structure of a flow channel. In some embodiments, the displacement is caused by a density wave. In some embodiments, the displacement is via droplet displacement. In some embodiments, the one or more flow channels further comprises a gate. In some embodiments, the one or more flow channels further comprises a sealable chamber. In some embodiments, the one or more flow channels further comprises one or more pneumatically driven valves. In some embodiments, the one or more flow channels further comprises one or more fluid reservoirs. In some embodiments, the one or more flow channels further comprises one or more peristaltic pumps.

In some embodiments, provided herein is an analyte imaging device comprising: a light modifying substrate; one or more photodetectors, wherein the one or more photodetectors is adjacent to the light modifying substrate; and one or more flow channels, wherein the one or more flow channels is adjacent to a surface of the light modifying substrate, and wherein a cross sectional dimension of the one or more flow channels is configured to allow the passage of a single cell.

In some embodiments, the light modifying substrate is displaced between the one or more photodetectors and the one or more flow channels. In some embodiments, the light modifying substrate comprises a diffractive optic layer. In some embodiments, the light modifying substrate is displaced between the one or more photodetectors and the one or more flow channels. In some embodiments, a diffractive optic layer is displaced between the one or more photodetectors and the one or more flow channels. In some embodiments, the one or more flow channels are displaced on or above the diffractive optic layer. In some embodiments, the light modifying substrate is configured to send and receive one or more photons to and from the one or more flow channels. In some embodiments, the diffractive optic layer is configured to send and receive one or more photons to and from the one or more flow channels. In some embodiments, the one or more photodetectors is configured to receive one or more photons from the light modifying substrate.

In some embodiments, the one or more photodetectors is configured to receive one or more photons from the diffractive optic layer.

In some embodiments, provided herein is a chip comprising one or more flow channels, wherein the one or more flow channels comprise one or more light scatter control elements adjacent to one or more analyte processing areas. In some embodiments, the one or more flow channels are configured to rotate a cell on an axis. In some embodiments, the one or light scatter control elements comprise one or more diffractive optic layers. In some embodiments, the one or light scatter control elements comprise one or more light scattering control elements. In some embodiments, the one or light scatter control elements are integrated with the chip. In some embodiments, the flow channel comprises one or more features configured to displace the cell. In some embodiments, the flow channel comprises one or more chemical functionalizations. In some embodiments, the one or more chemical functionalizations are configured to interact with one or more analytes. In some embodiments, the one or more flow channels is configured to receive an acoustic wave, wherein the acoustic wave is configured to rotate the cell on an axis. In some embodiments, the flow channel comprises one or more features configured to rotate the cell on an axis. In some embodiments, the one or more flow channels are configured to contact a light scattering control system. In some embodiments, the one or more flow channels have a width configured to pass one cell at a time. In some embodiments, the width of the one or more flow channels is 100 nanometers. In some embodiments, the one or more light scatter control elements reduces the signal to noise ratio of one or more optical signals emitted from the chip by at least a factor of 10. In some embodiments, the chip comprises at least 20 flow channels. In some embodiments, the chip comprises at least 100 flow channels. In some embodiments, the chip is integrated with a circuit. In some embodiments, the chip is integrated with a microfluidic circuit. In some embodiments, the chip is integrated with an electrical circuit. In some embodiments, the chip is integrated with a photonic circuit. In some embodiments, the chip is configured to connect to an analyte processing device disclosed herein.

In some embodiments, provided herein is an analyte processing device, comprising: one or more flow channels, at least one flow channel of the one or more flow channels comprising an analyte processing area; one or more excitation sources in optical communication with the analyte processing area; and one or more photodetectors in optical communication with the analyte processing area, the one or more photodetectors being configured to perform detection of a surface of one or more analytes in fluid motion, wherein the one or more photodetectors are configured to collect one or more two-dimensional images of one or more analytes, wherein the one or more two-dimensional images undergo processing to produce a three-dimensional structure of the one or more analytes.

In some embodiments, the one or more photodetectors are configured to simultaneously collect the one or more two-dimensional images. In some embodiments, the one or more photodetectors are configured to simultaneously collect the one or more two-dimensional images. In some embodiments, the one or more photodetectors are configured to collect the one or more two-dimensional images without the use of markers or labels. In some embodiments, the one or more photodetector(s) comprises at least one of: a spectral detector, an emissions detector, or a scattering detector. In some embodiments, the analyte processing device comprises at least one emissions detector and at least one scattering detector. In some embodiments, the one or more two-dimensional images determines the absolute or relative size of the analyte. In some embodiments, the three-dimensional structure of the analyte maps the surface of the analyte. In some embodiments, the three-dimensional structure of the analyte comprises deformed representations of the analyte. In some embodiments, the deformed representations of the same analyte represent different deformations. In some embodiments, the deformed representations of the analyte represent an unchanged deformation. In some embodiments, the one or more flow channels are a space-constrained tube relative to the analyte. In some embodiments, the three-dimensional structure of the analyte comprises stretched representations of the analyte while the analyte passes through the space-constrained tube. In some embodiments, the stretched representations of the analyte are differently stretched. In some embodiments, the stretched representations of the analyte are identically stretched. In some embodiments, the stretched representations of the analyte determine elasticity. In some embodiments, the stretched representations of the analyte determine granularity. In some embodiments, the one or more excitation sources in optical communication with the analyte processing area comprises an optical path from the one or more excitation sources to the analyte processing area, the optical path comprising a light scattering control system. In some embodiments, the analyte comprises multiple analytes comprising at least one of: small molecules, polymers, cellular structures, or surface markers. In some embodiments, the multiple analytes comprise materials from biological systems. In some embodiments, the materials from biological systems comprise cells or internal cell organelles. In some embodiments, the multiple analytes comprise free floating or secreted proteins. In some embodiments, the multiple analytes comprise a nucleotide. In some embodiments, the multiple analytes comprise or are contained within exosomes. In some embodiments, the multiple analytes comprise or are contained within neutrophils. In some embodiments, the multiple analytes comprise nucleotides. In some embodiments, the multiple analytes are extravesicular. In some embodiments, the three-dimensional structures of each of the multiple analytes is analyzed individually. In some embodiments, the three-dimensional structure of each of the multiple analytes may produce a new three-dimensional structure of an additional, larger analyte. In some embodiments, structural integrity of the multiple analytes is preserved after displacement in the one or more flow channels. In some embodiments, the surface markers comprise cell surface markers. In some embodiments, the processing is performed using Artificial Intelligence (AI). In some embodiments, the analyte processing area comprises a photomultiplier tube. In some embodiments, the one or more photodetectors comprises one or more single-photon avalanche diode (SPAD) arrays. In some embodiments, the one or more photodetectors comprise a single-photon avalanche diodes (SPAD) array. In some embodiments, the one or more photodetectors comprise one or more silicon photomultipliers (SiPM). In some embodiments, the one or more two-dimensional images comprises 1 pixel. In some embodiments, the one or more two-dimensional images has a 1:1 aspect ratio of the analyte. In some embodiments, the one or more two-dimensional images each depict an area on a surface of the analyte having a length of from 0.5 microns to 100 microns and a width from 0.5 microns to 100 microns, and a width being equal to or smaller than the length. In some embodiments, the one or more two-dimensional images having the 1:1 aspect ratio are combined with separate two-dimensional images of the same analyte with the same aspect ratio to produce the three-dimensional structure of an analyte. In some embodiments, the aspect ratios from the one or more two-dimensional images with the 1:1 aspect ratio are combined with separate two-dimensional images with different aspect ratios when producing the three-dimensional structure of one or more analytes. In some embodiments, the three-dimensional structure depicts a holistic distribution of surface markers of the one or more analytes. In some embodiments, the holistic distribution of surface markers can be defined as localized or partial. In some embodiments, the holistic distribution of surface markers can be defined as random. In some embodiments, the holistic distribution of surface markers can determine a parameter of a chemical or biological test. In some embodiments, a defined stretch or a deformation can determine a false positive for a chemical or biological test. In some embodiments, the parameter of a chemical or biological test can separate a false positive from a true positive. In some embodiments, the light scattering control system is configured to improve signal to noise ratio by at least a factor of five relative to photodetecting only unscattered or specular light.

In some embodiments, provided herein is a method for analyzing an analyte, comprising: providing a device comprising (i) a flow channel and (ii) one or more photodetectors in optical communication with the flow channel, wherein the one or more photodetectors comprises a light scattering control element; using the one or more photodetectors to acquire an optical signal from the analyte flowing through the flow channel; and processing the optical signal to identify a presence of the cell in the fluid flowing through the flow channel.

In some embodiments, provided herein is a method for analyzing an analyte, comprising: providing a device comprising (i) a flow channel comprising the analyte, and (ii) one or more photodetectors in optical communication with the flow channel; using the one or more photodetectors to acquire a first optical signal from the flow channel at a first position within the flow channel at a first time point; using the one or more photodetectors to acquire a second optical signal from the flow channel at a second position within the flow channel at a second time point subsequent to the first time point, wherein the second position is downstream of the first position; and processing the first optical signal and the second optical signal to identify the analyte flowing through the flow channel.

In some embodiments, the method further comprises using the one or more photodetectors to acquire a third optical signal at a third position within the flow channel. In some embodiments, the third position is downstream from the second position. In some embodiments, the first position, the second position, and the third position are equidistant from one other. In some embodiments, the difference between the second time point and the first time point is substantially equal to a difference between the third time point and the second time point. In some embodiments, the device comprises one or more excitation sources. In some embodiments, the one or more excitation sources provide excitation energy to the flow channel to yield the first optical signal, the second optical signal, or the third optical signal. In some embodiments, the one or more excitation sources comprises at least one continuous wave laser. In some embodiments, the one or more excitation sources comprises at least one pulsed laser. In some embodiments, the one or more excitation sources comprises at least one tunable laser. In some embodiments, the one or more excitation sources comprises a laser tuned to near IR to visible wavelengths. In some embodiments, the one or more excitation sources comprises a single laser. In some embodiments, the one or more excitation sources comprises multiple lasers. In some embodiments, the one or more excitation sources comprises bonded lasers. In some embodiments, the one or more excitation sources comprises external lasers. In some embodiments, the one or more photodetectors comprise a single pixel photodetector. In some embodiments, the flow channel is on a substrate. In some embodiments, the photodetectors are on the substrate. In some embodiments, the flow channel and the one or more photodetectors are on layers on the substrate. In some embodiments, the processing comprises Time-correlated Single Photon Counting (TCSPC). In some embodiments, the processing comprises Uncorrelated Time-lapse Microscopy (UTLM). In some embodiments, the method further comprises an analyte sorting operation. In some embodiments, the analyte motion is laminar. In some embodiments, the analyte motion is turbulent. In some embodiments, the analyte is not in motion. In some embodiments, the analyte is an aerosol. In some embodiments, the analyte is in the gas phase. In some embodiments, the analyte is in the liquid phase. In some embodiments, the analyte is an aqueous solution. In some embodiments, the analyte comprises one or more cells. In some embodiments, the analyte comprises blood. In some embodiments, the analyte comprises lymph. In some embodiments, the analyte comprises a cell line. In some embodiments, the analyte comprises a cell culture. In some embodiments, the analyte comprises a human cell. In some embodiments, the analyte comprises a bacterial cell. In some embodiments, the analyte comprises urine. In some embodiments, the analyte comprises bodily fluids. In some embodiments, the analyte comprises feces. In some embodiments, the analyte comprises peritoneal cavity fluid. In some embodiments, the analyte comprises bone marrow fluid. In some embodiments, the analyte comprises cerebrospinal fluid. In some embodiments, the analyte comprises cells purified from a subject's blood sample. In some embodiments, the analyte comprises blood serum or plasma. In some embodiments, the flow channel is configured to result in displacement of the analyte. In some embodiments, the displacement is electrical. In some embodiments, the displacement is magnetic. In some embodiments, the analyte displacement is thermal. In some embodiments, the one or more photodetectors is configured for spectral range. In some embodiments, the one or more photodetectors is configured for photon intensity. In some embodiments, the one or more photodetectors is configured for photon wavelength. In some embodiments, the one or more photodetectors comprises a pinned photodiode. In some embodiments, the one or more photodetectors comprises a single photon avalanche diode. In some embodiments, the processing comprises time of flight processing.

In some embodiments, provided herein is a method of imaging an analyte in motion, comprising: providing a flow channel adjacent to one or more photodetectors, wherein the flow channel comprises an analyte processing area configured for one or more photodetection events; providing conditions sufficient for the analyte to travel along a path in the flow channel; using the one or more photodetectors to probe the analyte in motion N times within the analyte processing area, wherein N is a number greater than one; repeating the first through third operation (i-iii) M times to generate an N×M time of flight (TOF) data for the analyte in motion, wherein M is a number greater than one; and using the N×M TOF data to classify the analyte in motion at an accuracy greater than 80%.

In some embodiments, using the N×M TOF data classifies the analyte in motion at an accuracy greater than 90%. In some embodiments, using the N×M TOF data classifies the analyte in motion at an accuracy greater than 95%. In some embodiments, using the N×M TOF data classifies the analyte in motion at an accuracy greater than 98%. In some embodiments, using the N×M TOF data classifies the analyte in motion at an accuracy greater than 99%. In some embodiments, the analyte in motion is probed at spatially separate locations along the analyte processing area. In some embodiments, the flow channel further comprises one or more pneumatically driven valves. In some embodiments, the flow channel further comprises one or more fluid reservoirs. In some embodiments, the flow channel further comprises one or more peristaltic pump valves. In some embodiments, the flow channel further comprises one or more peristaltic pump valves. In some embodiments, the classification confirms a biotherapeutic analytical characterization. In some embodiments, the classification comprises classifying a cellular phenotype. In some embodiments, the classification comprises using a machine learning algorithm. In some embodiments, the machine learning algorithm is a convolutional neural network. In some embodiments, the machine learning algorithm is a generational neural network. In some embodiments, the convolutional neural network is a 1D neural network trained using a training data set comprising at least 100 data sets. In some embodiments, the machine learning algorithm classifies cells as cancerous or non-cancerous. In some embodiments, the machine learning algorithm classifies at least 100,000 cells per second. In some embodiments, the machine learning algorithm classifies with a false negative rate of less than one in one billion. In some embodiments, the machine learning algorithm classifies with a false positive rate of less than one in one billion. In some embodiments, the machine learning algorithm classifies with a true positive rate of at least 99.9 percent.

In some embodiments, provided herein is a method of determining a dimension of an analyte or a cell, the method comprising subjecting the analyte or the cell to flow along a flow channel; and repeatedly detecting one or more beams of light, wherein the one or more beams of light are scattered by the analyte or the cell, and wherein the one or more beams of light comprise an angular light scattering pattern, wherein the angular light scattering pattern identifies the dimension of the analyte or the cell. In some embodiments, provided herein is a method of determining a dimension of an analyte or a cell, the method comprising subjecting the analyte or the cell to flow along a flow channel; and repeatedly detecting one or more beams of light, wherein the one or more beams of light are scattered by the particle or the cell, and wherein the one or more beams of light comprise a light scattering spectral pattern, wherein the light scattering spectral pattern identifies the dimension of the analyte or the cell. In some embodiments, provided herein is a method for processing or analyzing a cell, comprising (a) subjecting the cell to flow along a flow channel and (b) detecting a signal from the cell to identify the cellular size at an accuracy of at least 10−9 m in a time period of at most 10 minutes. In some embodiments, provided herein is a method for processing or analyzing a cell, comprising (a) subjecting the cell to flow along a flow channel and (b) detecting a signal from the cell to identify the cellular organelle size at an accuracy of at least 10−9 m in a time period of at most 10 minutes. In some embodiments, provided herein is a method for processing or analyzing a cell, comprising (a) subjecting the cell to flow along a flow channel and (b) detecting a signal from the cell to identify a number of cellular mitochondria at an accuracy of at least 95 percent in a time period of at most 10 minutes. In some embodiments, provided herein is a method for processing or analyzing a cell, comprising (a) subjecting the cell to flow along a flow channel and (b) detecting a signal from the cell to identify a population of at least 1,000 cells in a time period of at most 10 minutes. In some embodiments, provided herein is a method of imaging a surface of a cell, the method comprising: providing a fluidic microchannel configured to receive the cell, wherein the fluidic microchannel comprises at least two detection zones along a length of the fluidic microchannel, wherein each of the at least two detection zones comprise an imager, and wherein the microfluidic channel comprises a feature adjacent to the at least two detection zones, wherein the feature is configured to induce a rotation along an axis of the cell upon contact with the cell; disposing the cell in the fluidic microchannel; providing a force adjacent to the fluidic microchannel, thereby traversing the cell across the length of the fluidic microchannel, wherein the feature does not terminate the traversing of the cell across the length of the fluidic microchannel; and capturing at least two, two dimensional images of the cell. In some embodiments, the at least two, two dimensional images of the cell are at least super-resolution. In some embodiments, the method further comprises generating a three-dimensional structure of the cell derived from the at least two, two dimensional images of the cell. In some embodiments, provided herein is a method of imaging a surface of a cell in three dimensions, the method comprising:

a. providing a flow channel configured to receive the cell, wherein the flow channel comprises at least a first detection zone and a second detection zone along a length of the flow channel, wherein the first detection zone, the second detection zone, or both, comprises an imager, and wherein the microfluidic channel comprises a feature adjacent to the first detection zone or the second detection zone, wherein the feature is configured to induce a rotation along an axis of the cell upon contact with the cell; (b) disposing the cell in the flow channel; (c) subjecting the cell to flow through the flow channel; (d) capturing one or more images of the cell as the cell passes the first detection zone and the second detection zone; and (e) generating a three-dimensional structure of the cell derived from the one or more images of the cell. In some embodiments, the feature does not terminate the flow of the cell through the fluidic microchannel. In some embodiments, the three-dimensional structure comprises an atlas of the cell. In some embodiments, the three-dimensional structure of the cell is at least super-resolution. In some embodiments, the three-dimensional structure comprises a classification of one or more membrane bound structures of the cell. In some embodiments, the three-dimensional structure comprises a morphometric classification of the cell. In some embodiments, the three-dimensional structure comprises a topography map of one or more membrane bound structures of the cell. In some embodiments, the three-dimensional structure comprises a map comprising a location of the one or more membrane bound structures on the surface of the cell. In some embodiments, the three-dimensional structure further comprises a motion dynamic characterization of the cell. In some embodiments, the detection comprises a spatial density map of one or more analytes. In some embodiments, the three-dimensional structure comprises one or more dynamic topographical data of the cell. In some embodiments, the cell is a single cell of a population of cells, and wherein the method further comprises repeating (b)-(e) for a second cell of the population of cells. In some embodiments, the steps (b)-(e) for the second cell of the population of cells occurs simultaneously to the first cell. In some embodiments, the repeating (b)-(e) for the second cell of the population of cells occurs subsequent to the first cell. In some embodiments, the first cell is a single cell of a population of cells, and wherein the method further comprises repeating (b)-(e) for a hundredth cell of the population of cells. In some embodiments, the repeating (b)-(e) for the hundredth cell of the population of cells occurs simultaneously to the first cell. In some embodiments, the repeating (b)-(e) for the hundredth cell of the population of cells occurs subsequent to the first cell. In some embodiments, provided herein is a method of analyzing a subject's blood comprising connecting a subject's blood flow to a device or analyte processing device disclosed herein. In some embodiments, the analysis comprises cancer cell detection. In some embodiments, the analysis comprises preparation of a subject's blood prior to analysis. In some embodiments, the analysis further comprises removal of cancer cells. In some embodiments, the analysis comprises intermittent sampling of the subject's blood. In some embodiments, provided herein is a method of spatially identifying one or more markers on an analyte surface, comprising: subjecting the analyte to flow through a flow channel; subjecting the analyte to one or more excitation sources, wherein the one or more excitation sources generates a light scattering pattern of the analyte surface; processing the light scattering pattern algorithmically to generate a topographic map of the analyte surface. In some embodiments, the topographic map comprises a location map of one or more markers. In some embodiments, the topographic map comprises an intensity map of one or more markers. In some embodiments, the topographic map comprises a density map of one or more markers.

In some embodiments, provided herein is a method for analyzing an analyte, comprising: providing a device comprising (i) a flow channel comprising the analyte, and (ii) one or more photodetectors in optical communication with the one or more flow channels; using the one or more photodetectors to acquire a first optical signal from the one or more flow channels at a first time point; using the one or more photodetectors to acquire a second optical signal from the one or more flow channels at a second time point subsequent to the first time point; and processing the first optical signal and the second optical signal to identify the analyte flowing through the one or more flow channels, collecting one or more two-dimensional images of the analyte, wherein the one or more two-dimensional images are combined and optimized algorithmically to produce a three-dimensional structure of the analyte, wherein the analyte in fluid motion is imaged as if it were static.

In some embodiments, the method further comprises using the one or more photodetectors to acquire a third optical signal at a third time point within the one or more flow channels. In some embodiments, the device further comprises one or more excitation sources in optical communication with the analyte processing area. In some embodiments, the method further comprises processing the three-dimensional structures to improve analyte analysis. In some embodiments, the method further comprises using the three-dimensional structure to determine analyte characteristics for a chemical or biological test. In some embodiments, the analyte characteristics reduce the number of false positives. In some embodiments, the analyte characteristics of multiple analytes is used to determine analyte characteristic distribution of a population of analytes. In some embodiments, the reduced number of false positives results in a change in a treatment protocol. In some embodiments, the method further comprises using the three-dimensional structure to separate false positive cancer tests from true cancer positives, wherein the results are used to create an individualized cancer treatment plan. In some embodiments, the analyte characteristic distribution of a population of analytes indicates the severity of multiple myeloma for a subject. In some embodiments, the characterization of the population of analytes can be used to extrapolate a causal factor of multiple myeloma present in the subject.

In some embodiments, provided herein is a method of spatially identifying one or more characteristics on an analyte surface, comprising: subjecting the analyte to flow through a flow channel; photodetecting by a single-photon avalanche diode (SPAD) array light emission from the analyte during the flow through the flow channel, wherein the analyte is in motion; and processing the light emission to generate a topographic map of the analyte surface.

In some embodiments, provided herein is a method of spatially identifying one or more characteristics on an analyte surface, comprising: subjecting the analyte to flow through a flow channel; subjecting the analyte to light from one or more excitation sources, wherein the light is polarized by a light scattering control system; photodetecting by a single-photon avalanche diode (SPAD) array light emission from the analyte; and processing the light emission to generate a topographic map of the analyte surface.

In some embodiments, provided herein is a method of spatially identifying one or more characteristics on an analyte surface, comprising: subjecting the analyte to flow through a flow channel; photodetecting by a single-photon avalanche diode (SPAD) array light emission from the analyte due to light from one or more excitation sources, wherein the light is polarized by a light scattering control system; and algorithmically processing the light emission to generate a topographic map of the analyte surface.

In some embodiments, provided herein is a method of spatially identifying one or more characteristics on an analyte surface, comprising: subjecting the analyte to flow through a flow channel, wherein the analyte; photodetecting by a single-photon avalanche diode (SPAD) array light emission from the analyte the analyte to one or more excitation sources, wherein the one or more excitation sources generates a polarized light scattering pattern of the analyte surface; processing the polarized light scattering pattern algorithmically to generate a topographic map of the analyte surface. In some embodiments, the light scattering control system is adjacent to one or more photodetectors. In some embodiments, the light scattering control system is adjacent to the flow channel. In some embodiments, the light scattering control system is adjacent to the light scattering control system. In some embodiments, the topographic map comprises an atlas of cellular expression.

In some embodiments, provided herein is a method for processing or analyzing a cell, comprising (a) subjecting the cell to flow along a flow channel and (b) detecting one or more two-dimensional images from the cell to generate a two-dimensional structure of the cell, wherein the two-dimensional structure comprises a topographic map.

In some embodiments, provided herein is a method for processing or analyzing a cell, comprising (a) subjecting the cell to flow along a flow channel and (b) detecting one or more two-dimensional images from the cell to generate a three-dimensional structure of the cell, wherein the three-dimensional structure comprises a topographic map.

In some embodiments, provided herein is a method for processing or analyzing a population of cells, comprising (a) subjecting the population of cells to flow along a flow channel and (b) detecting one or more two-dimensional images from the population of cells to generate one or more three-dimensional structures of the population of cells, wherein the population of cells is at least 1,000 cells, wherein the three-dimensional structures comprise a topographic map.

In some embodiments, provided herein is a method for processing or analyzing a cell, comprising (a) subjecting the cell to flow along a flow channel and (b) detecting one or more two-dimensional images from the cell to generate a three-dimensional structure of the cell in a time period of at most 10 minutes, wherein the three-dimensional structure comprises a topographic map. In some embodiments, the cell is amongst a population of at least 1,000 cells.

In some embodiments, provided herein is a system for spatially identifying one or more markers on an analyte surface, the system comprising: subjecting the analyte to flow through a flow channel; subjecting the analyte to one or more excitation sources, wherein the one or more excitation sources generates a light scattering pattern of the analyte surface; and processing the light scattering pattern algorithmically to generate a topographic map of the analyte surface.

In some embodiments, provided herein is a method of spatially identifying one or more markers on an analyte surface, comprising: subjecting the analyte to flow through a flow channel; subjecting the analyte to one or more excitation sources, wherein the one or more excitation sources generates a light scattering pattern of the analyte surface; using the light scattering pattern of the analyte surface to generate a topographic map of the analyte surface.

In some embodiments, provided herein is a system for spatially identifying one or more markers on an analyte surface, comprising: subjecting the analyte to flow through a flow channel; subjecting the analyte to one or more excitation sources, wherein the one or more excitation sources generates a light scattering pattern of the analyte surface; and using the light scattering pattern of a surface of an analyte to generate a topographic map of the analyte surface.

In some embodiments, provided herein is a method for processing or analyzing a cell, comprising (a) subjecting the cell to flow along a flow channel and (b) detecting one or more two-dimensional images from the cell to generate a three-dimensional structure of the cell, wherein the three-dimensional structure comprises a topographic map.

In some embodiments, provided herein is a method for processing or analyzing a population of cells, comprising (a) subjecting the population of cells to flow along a flow channel and (b) detecting one or more two-dimensional images from the population of cells to generate one or more three-dimensional structures of the population of cells, wherein the population of cells is at least 1,000 cells, wherein the three-dimensional structure comprises a topographic map.

In some embodiments, provided herein is a method for processing or analyzing a cell, comprising (a) subjecting the cell to flow along a flow channel and (b) detecting one or more two-dimensional images from the cell to generate a three-dimensional structure of the cell in a time period of at most 10 minutes, wherein the three-dimensional structure comprises a topographic map. In some embodiments, the cell is amongst a population of at least 1,000 cells.

In some embodiments, provided herein is a system for spatially identifying one or more markers on an analyte surface, the system comprising: subjecting the analyte to flow through a flow channel; subjecting the analyte to one or more excitation sources, wherein the one or more excitation sources generates a light scattering pattern of the analyte surface; and processing the light scattering pattern algorithmically to generate a topographic map of the analyte surface.

In some embodiments, provided herein is a method of spatially identifying one or more markers on an analyte surface, comprising: subjecting the analyte to flow through a flow channel; subjecting the analyte to one or more excitation sources, wherein the one or more excitation sources generates a light scattering pattern of the analyte surface; using the light scattering pattern of a surface of an analyte to generate a topographic map of the analyte surface.

In some embodiments, provided herein is a system for spatially identifying one or more markers on an analyte surface, comprising: subjecting the analyte to flow through a flow channel; subjecting the analyte to one or more excitation sources, wherein the one or more excitation sources generates a light scattering pattern of the analyte surface; and using the light scattering pattern of a surface of an analyte to generate a topographic map of the analyte surface.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

INCORPORATION BY REFERENCE

All publications, patents, and patent applications mentioned in this specification are herein incorporated by reference to the same extent as if each individual publication, patent, or patent application was specifically and individually indicated to be incorporated by reference.

DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides devices, methods, and systems for high resolution imaging and high throughput analyte identification, under mild conditions within a flow channel. The present disclosure provides a platform for multi-omics analysis including genome, epigenome, transcriptome, and proteome studies. Devices provided herein can perform comprehensive, accurate assessments of populations of analytes and cells, including the heterogeneity of cells. An embodiment of the present invention comprises the integration or coupling of independent elements of analyte detection systems. An embodiment of the present invention comprises the integration or coupling of independent elements of analyte detection systems into high resolution imaging and high throughput analyte identification devices and methods. There are many challenges to achieving high throughput analyte detection using devices, methods, and systems comprising a photodetector array, a microfluidic channel, and one or more excitation sources integrated together. For some embodiments, the device comprises a photodetector array, a microfluidic channel, one or more excitation sources, and one or more light scattering control systems integrated together to yield the precision and scale of the device. For another example, one or more photodetectors may be coupled with one or more flow channels, and one or more light scattering control elements. The light scattering control systems disclosed herein can be used to reduce unwanted noise during imaging of biological entities within a flow channel. For example, dichroic optical elements may reduce optical signal transmitted between a cellular substrate and one or more photodetectors. For some embodiments, the device comprises a chip comprising an integrated photodetector array, a microfluidic channel, and one or more excitation sources integrated together.

Figure 1A:
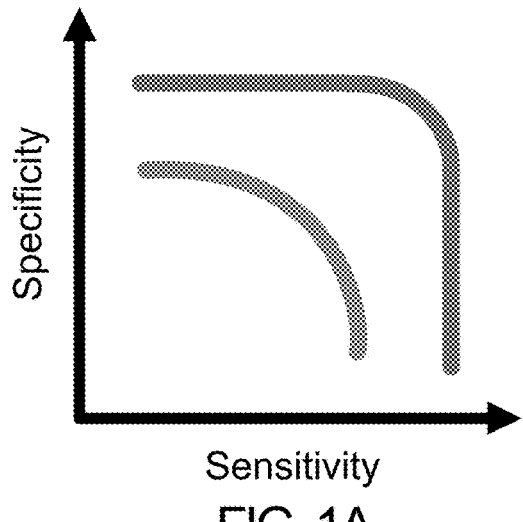
FIG. 1A illustrates aspects of the sensitivity and specificity improvements with the analyte processing device disclosed herein, analyte processing device disclosed herein, including run multiplexing, cell imaging modality, cell multi-imaging, and cell sorting.
Figure 1D:
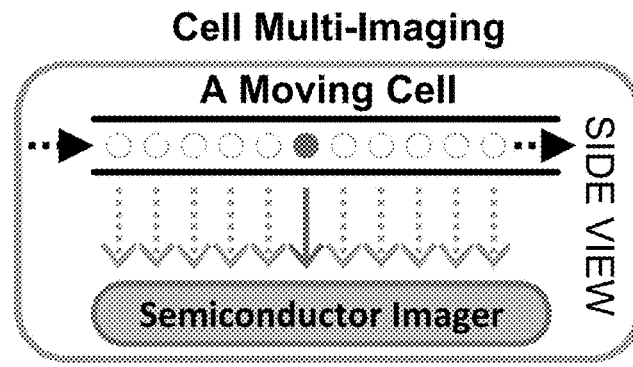
FIG. 1D shows a cell multi-imaging modality.
Figure 1B:
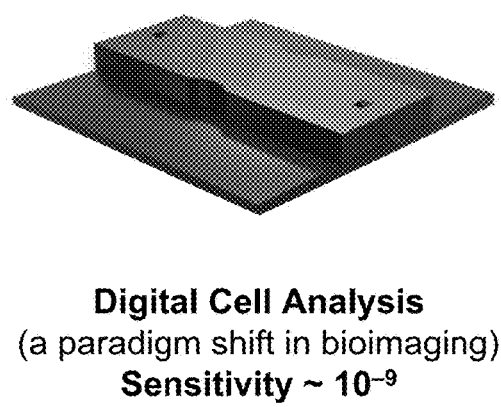
FIG. 1B shows digital cell analysis possible with the analyte processing device disclosed herein.
Figure 1E:
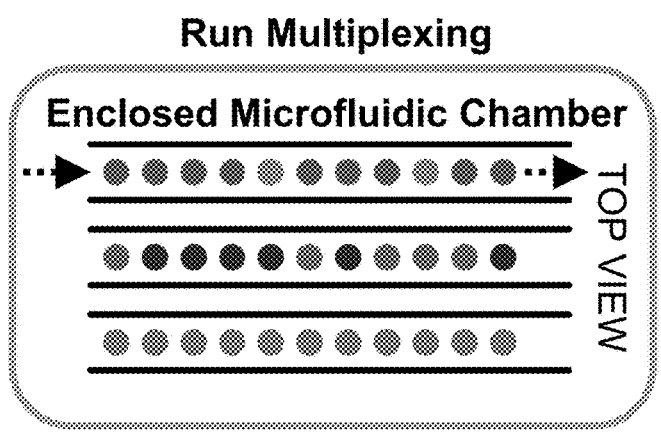
FIG. 1E shows run multiplexing with enclosed microfluidic chambers disclosed herein.
Figure 1C:
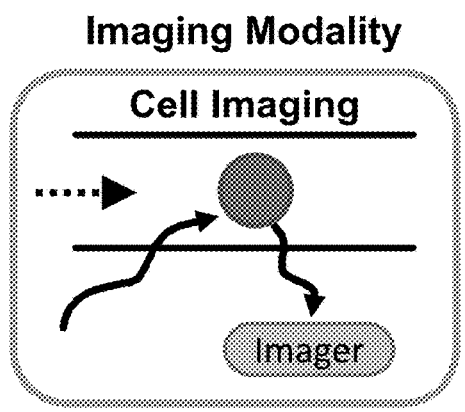
FIG. 1C shows a cell imaging modality.
Figure 1F:
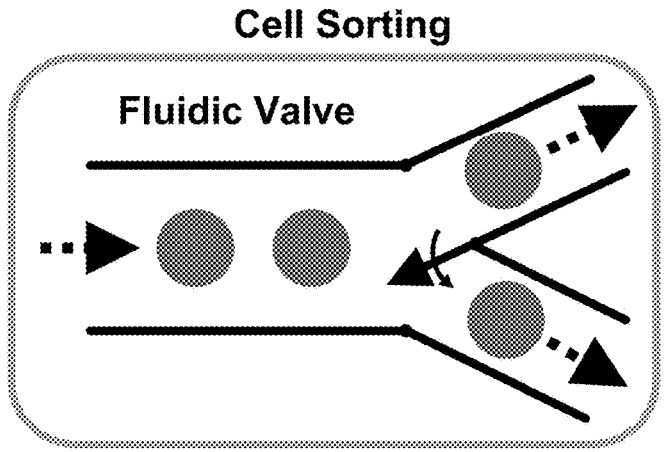
FIG. 1F shows a cell sorting modality.
Figure 2:
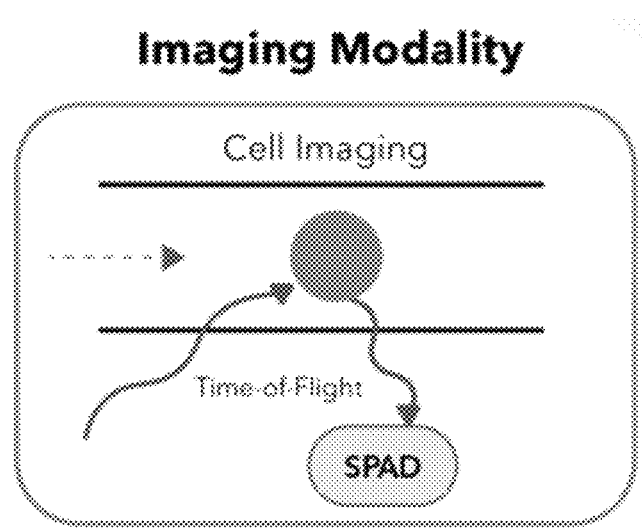
FIG. 2 illustrates a time of flight cell imaging modality of the device described herein via a single photon avalanche diode (SPAD) array.
Figure 3:
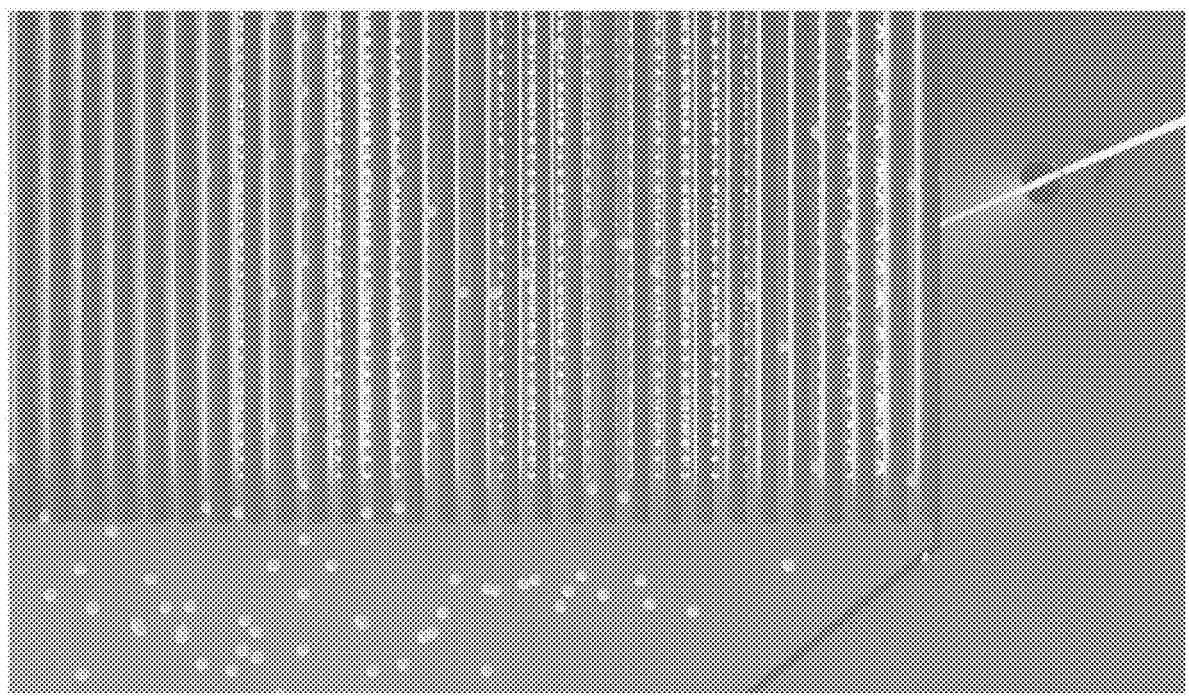
FIG. 3 depicts cells entering in a single column into the detector.
Figure 4:
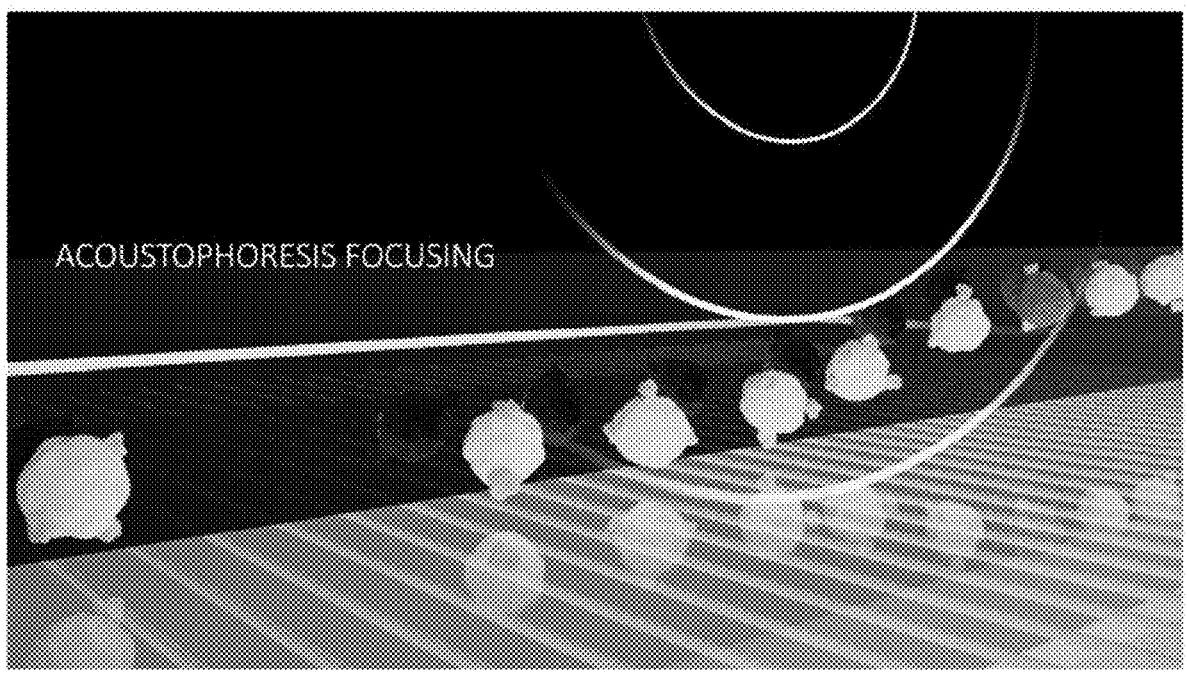
FIG. 4 depicts acoustophoresis effect on cells.
Figure 5:
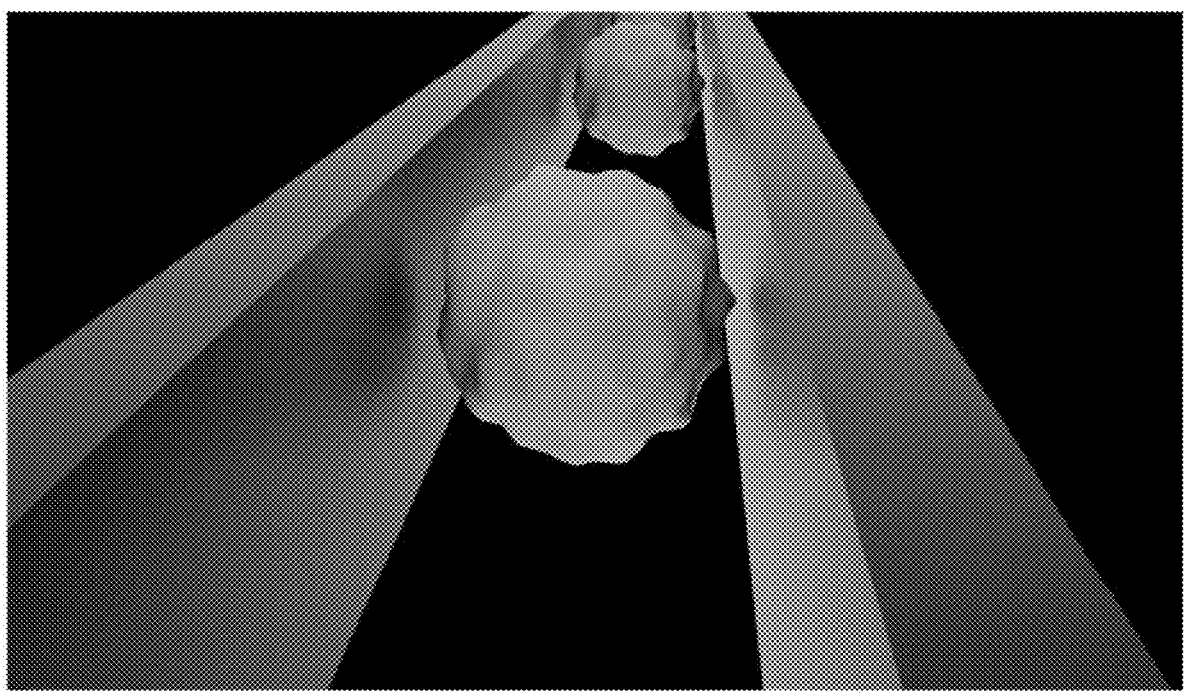
FIG. 5 depicts a cell moving through a microfluidic channel.
Figure 6:
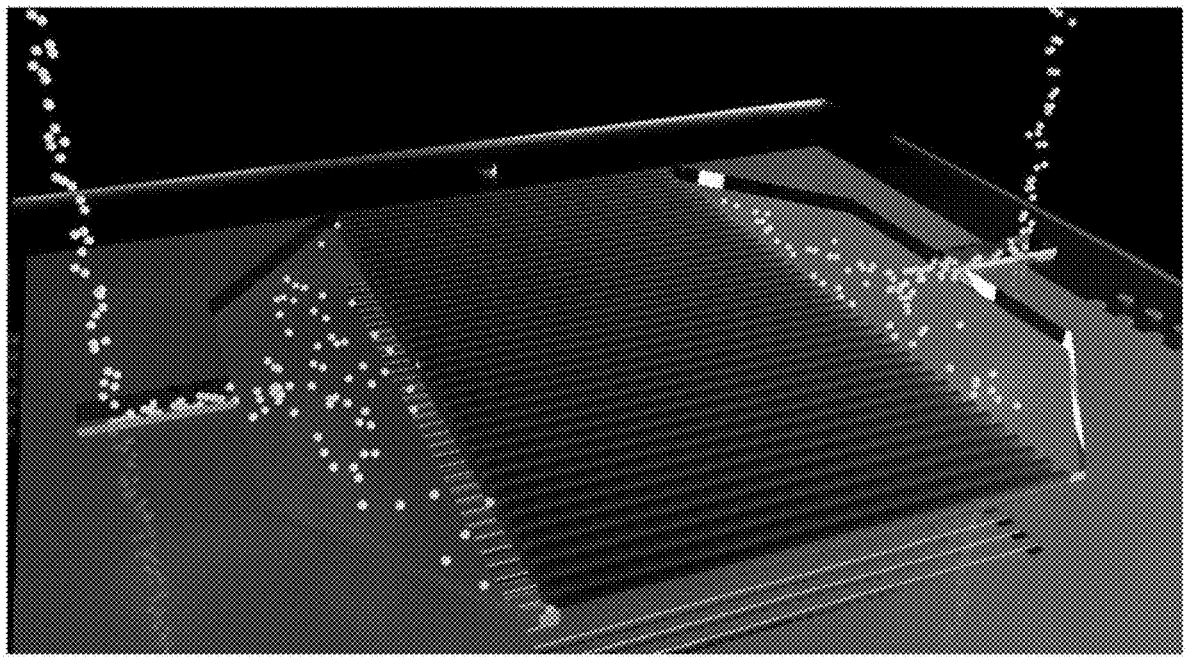
FIG. 6 depicts microfluidic channel system.
Figure 7:
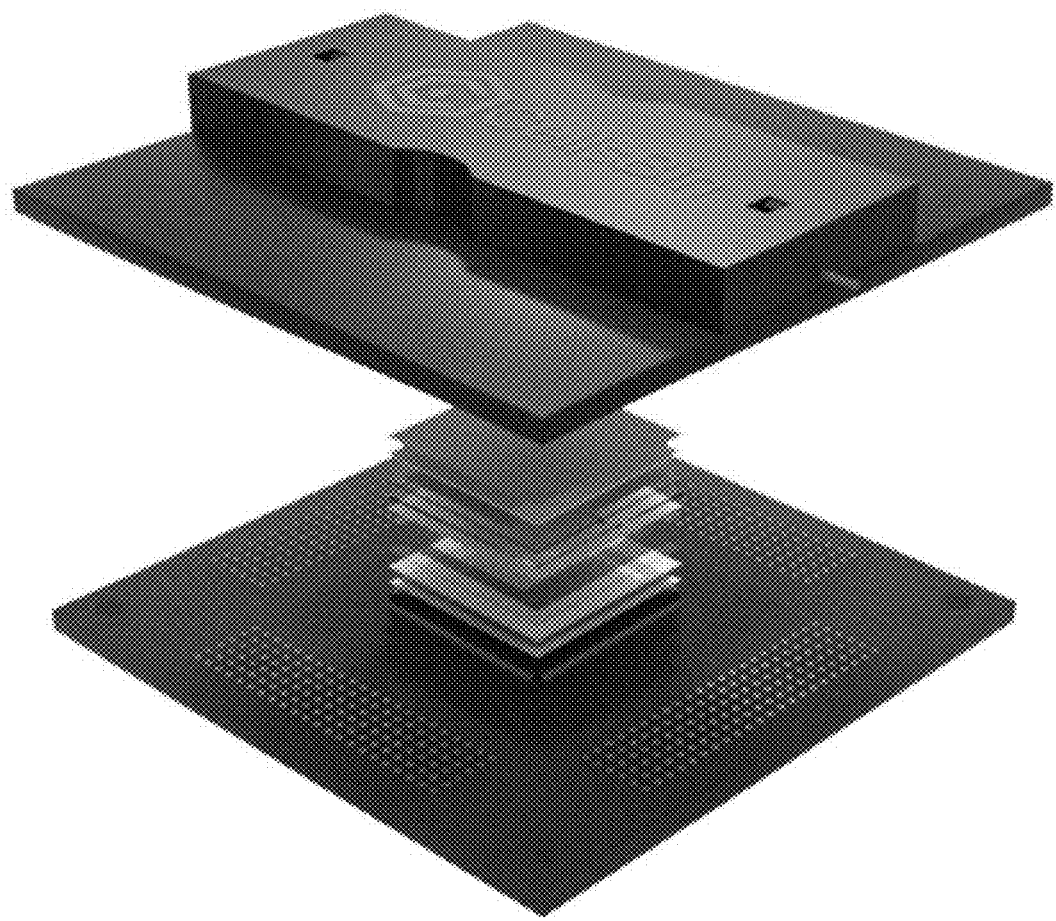
FIG. 7 shows an example of an integrated circuit disclosed herein.
Figure 8:
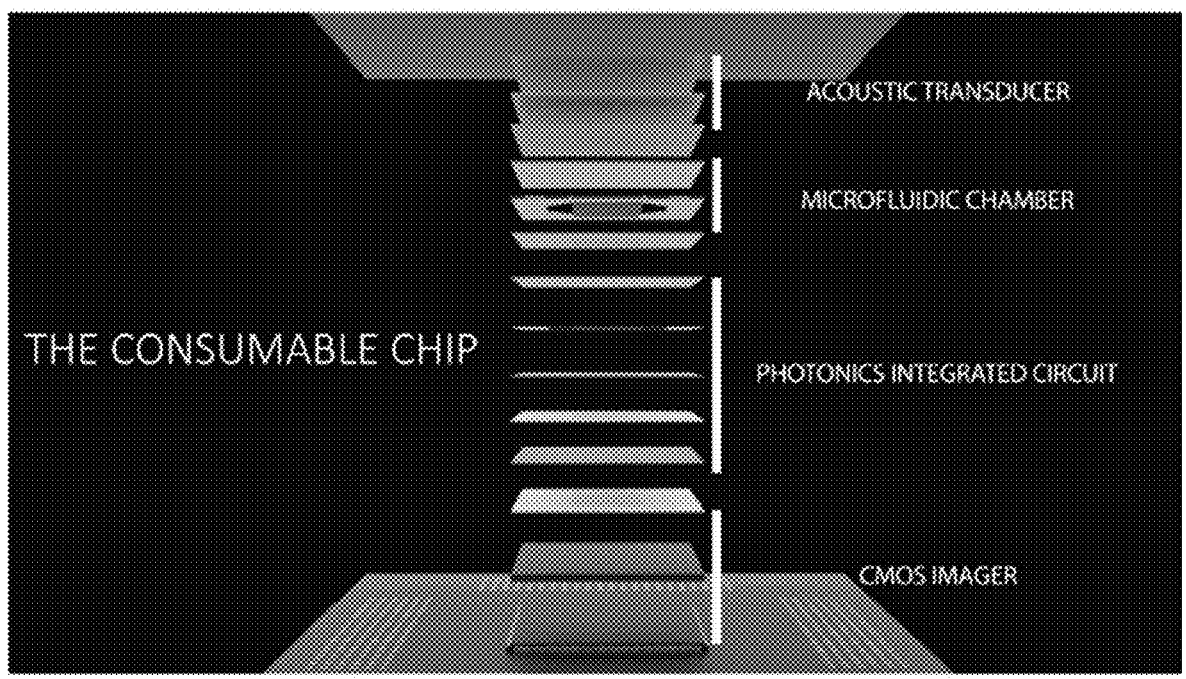
FIG. 8 shows an example of layers comprising a microfluidic device disclosed herein.

The devices and methods provided herein may provide rapid, high-throughput, parallel, multiplexable genetic, protein, and other cellular analyses down to single-molecule or single-cell level and can be used for several applications including but not limited to the isolation and detection of immune cells, circulating tumor cells (CTCs), cell-free nucleic acids and exosomes, cancer initiating cells, cell drug interaction and resistance, cell-cell communication in tumor microenvironments, and the analysis of genomes and epigenomes using single-cell next-generation imaging technologies. In order to yield the information for such analysis, delicate imaging techniques are implemented with an analyte while also having the precision to accurately characterize said analytes. In some embodiments of the methods and devices disclosed herein achieves the precision and sensitivity through an arrangement of photodetection and light modifying materials. The resulting optical communication along the optical path between the one or more photodetectors reduces signal interference by noise during imaging. The effect on sensitivity, error rate of identification, and false positive rate can be observed in FIG. 9A, FIG. 9B, and FIG. 10A. The resulting analyte processing device can achieve measurement precision at the nanometer scale, as well as achieving the capacity to efficiently and rapidly sort analytes upon imaging and characterization. An important feature of the analyte processing device is its ability to perform high throughput analysis while also featuring low levels of shear stress on analytes and cells. The viability rate, for example, of the resulting analyzed cells after imaging is thus superior to other imaging methods with harsher conditions. Cell tolerability also means more sophisticated imaging methods are possible with otherwise unstable cell types. Furthermore, the throughput of analysis possible with the analyte processing device described herein is improved over existing technology, with the possibility of thousands of cells or analytes to be processed, imaged, or distributed in short periods of time. FIG. 1A, FIG. 1B, FIG. 1C, FIG. 1D, FIG. 1E, and FIG. 1F show some aspects of the device described herein. FIG. 2 shows the imaging modality and how it provides a mechanism to perform time of flight imaging via a photodetector array within a flow channel. FIG. 3, FIG. 4, FIG. 5, and FIG. 6 show depictions of cells moving with a microfluidic device described herein. FIG. 4 shows the effect of acoustophoresis on cells within a microfluidic channel described herein. FIG. 7 show an example of a microfluidic device comprising an integrated circuit, including the layers of the microfluidic device. FIG. 8 shows an example of a consumable chip and its layers, including an acoustic transducer layer, a microfluidic chamber layer, a photonics integrated circuit layer, and a CMOS imager layer.

Analyte Processing Device

An aspect of the present disclosure provides an analyte processing device for detecting a presence or absence of an analyte in a solution. In some embodiments, provided herein is an analyte processing device, comprising: one or more flow channels, wherein at least one flow channel of the one or more flow channels comprise an analyte processing area; one or more excitation sources in optical communication with the analyte processing area and comprising an optical path from the one or more excitation sources to the analyte processing area; and one or more photodetectors in optical communication with the analyte processing area, wherein the optical path comprises a light scattering control system.

In some embodiments, provided herein is an analyte processing device, comprising: one or more flow channels, wherein at least one flow channel of the one or more flow channels comprise an analyte processing area; one or more excitation sources in optical communication with the analyte processing area and comprising an optical path from the one or more excitation sources to the analyte processing area; and one or more photodetectors in optical communication with the analyte processing area, wherein the optical path comprises a light scattering control system, wherein (i), (ii), (iii), or any combination thereof are integrated monothically, system-in-package, heterogeneously, three-dimensionally integrated, or a combination thereof. In some embodiments, provided herein is an analyte processing device, comprising: one or more flow channels, at least one flow channel of the one or more flow channels comprising an analyte processing area; one or more excitation sources in optical communication with the analyte processing area; and one or more photodetectors in optical communication with the analyte processing area, the one or more photodetectors being configured to perform detection of a surface of one or more analytes in fluid motion, wherein the one or more photodetectors are configured to collect one or more two-dimensional images of one or more analytes, wherein the one or more two-dimensional images undergo processing to produce a three-dimensional structure of the one or more analytes.

In other embodiments, the analyte processing device measures an analytes size, texture, surface area, or other physical property. During cellular analysis, the analyte processing device may be used to determine organelle size, cell membrane size, mitochondrial count, organelle count, or other physical parameters of biological systems. The methods and devices of the present disclosure may also be used to detect, analyze, or quantify, a plurality of analytes present in an aqueous sample. The geometric arrangement, material, and circuitry of the analyte processing device may vary for imaging performance under flow channel conditions.

In some embodiments, the analyte processing device comprises one or more of the following: $SiO_2$, TiN, Ti, $Si_3N_4$, glass, or other similar material. In some embodiments, the analyte processing device comprises a series of layers. In some embodiments, the analyte processing device comprises one or more light scattering control elements. In some embodiments the analyte processing device comprises one or more light scattering control elements forming one or more layers. In some embodiments, the analyte processing device comprises an acoustophoretic layer. In some embodiments, the analyte processing device comprises a flow channel layer. In some embodiments, the analyte processing device comprises a microfluidic channel layer. In some embodiments, the analyte processing device comprises a photonics circuit layer comprising one or more excitation sources or one or more optical circuits. In some embodiments, the analyte processing device comprises an analyte processing area. In some embodiments, the analyte processing device comprises one or more analyte processing areas. In some embodiments, the analyte processing device comprises a substrate, element, or membrane to manipulate the scattering of light. In some embodiments, the analyte processing device comprises a substrate, element, or membrane to manipulate the propagation of light.

In some embodiments, the analyte processing device comprises a chip. In some embodiments, the analyte processing device comprises a cartridge. In some embodiments, the analyte processing device comprises a replaceable cartridge. In some embodiments, the analyte processing device comprises a replaceable or consumable element. In some embodiments, the chip is integrated with one or more photodetectors, the one or more excitation sources, one or more flow channels, one or more light scattering control elements, or any combination thereof. In some embodiments, the analyte processing device comprises a semiconductor chip. In some embodiments, the analyte processing device comprises a photonics chip. In some embodiments, the chip is integrated with one or more light modifying elements. In some embodiments, the chip is integrated with one or more light scattering control systems. In some embodiments, the analyte processing device comprises one or more stacked layers. In some embodiments, the one or more stacked layers are integrated with a chip. In some embodiments, the analyte processing device comprises one or more stacked layers integrated with a chip. In some embodiments, the chip may comprise several layers including but not limited to: an acoustophoresis layer, a microfluidic chamber layer, a microfluidic channel layer, a flow channel layer, a light modifying membrane layer, a photodetector layer, an excitation source layer, an optical circuit layer, a photonics circuit layer, or a light modifying substrate layer. In some embodiments, the optical circuit comprises one or more light entry sections, one or more optical dividers, a light delivery section, or any combination thereof. In some embodiments, the analyte processing device comprises an energy source. In some embodiments, the energy source is a battery. In some embodiments, the energy source is integrated with the analyte processing device. In some embodiments, the device comprises one or more excitation sources. In some embodiments, the one or more excitation sources provide excitation energy to the flow channel to yield the first optical signal, the second optical signal, or the third optical signal.

In some embodiments, provided herein is a chip comprising one or more flow channels, wherein the one or more flow channels comprise one or more light scatter control elements adjacent to one or more analyte processing areas. In some embodiments, the chip comprises an application specific integrated circuit. In some embodiments, the chip comprises an integrated circuit. In some embodiments, the chip is integrated with one or more other aspects of the analyte processing device, including but not limited to: one or more flow channels, one or more light scattering control elements, a power source, one or more photodetectors, one or more excitation sources, or one or more displacement/phoresis elements, one or more circuits, or one or more chips. In some embodiments, the chip comprises an optical circuit. In some embodiments, readout circuitry may be operatively coupled to the analyte processing device, wherein the readout circuitry is configured to transmit the data from the analyte processing device to memory. In some embodiments, the chip comprises at least 20 flow channels. In some embodiments, the chip comprises at least 100 flow channels. In some embodiments, the chip is integrated with a circuit. In some embodiments, the chip is integrated with a microfluidic circuit. In some embodiments, the chip is integrated with an electrical circuit. In some embodiments, the chip is integrated with a photonic circuit. In some embodiments, the chip is configured to connect to an analyte processing device disclosed herein.

Analyte Imaging Device

An aspect of the present disclosure provides an analyte imaging device for detecting a presence or absence of an analyte in a solution. In some embodiments, provided herein is an analyte imaging device comprising: a light modifying substrate; one or more photodetectors, wherein the one or more photodetectors is adjacent to the light modifying substrate; and one or more flow channels, wherein the one or more flow channels is adjacent to a surface of the light modifying substrate, and wherein a cross sectional dimension of the one or more flow channels is configured to allow the passage of a single cell. In other embodiments, the analyte imaging device measures an analyte's size, texture, surface area, or other physical property. During cellular analysis, the analyte imaging device may be used to determine organelle size, cell membrane size, mitochondrial count, organelle count, or other physical parameters of biological systems. The methods and devices of the present disclosure may also be used to detect, analyze, or quantify, a plurality of analytes present in an aqueous sample. The geometric arrangement, material, and circuitry of the analyte imaging device may vary for imaging performance under flow channel conditions. analyte imaging device In some embodiments, the analyte imaging device comprises one or more of the following: $SiO_2$, TiN, Ti, $Si_3N_4$, glass, or other similar material. In some embodiments, the analyte imaging device comprises one or more of the following: $SiO_2$, TiN, Ti, $Si_3N_4$, and glass. In some embodiments, the analyte imaging device comprises one or more of layers. In some embodiments, the analyte imaging device comprises one or more light scattering control elements. In some embodiments the analyte imaging device comprises one or more light scattering control elements forming one or more layers. In some embodiments, the analyte imaging device comprises an acoustophoretic layer. In some embodiments, the analyte imaging device comprises a flow channel layer. In some embodiments, the analyte imaging device comprises a microfluidic channel layer. In some embodiments, the analyte imaging device comprises a photonics circuit layer comprising one or more excitation sources or one or more optical circuits. In some embodiments, the analyte imaging device comprises an analyte processing area. In some embodiments, the analyte imaging device comprises one or more analyte processing areas. In some embodiments, the analyte imaging device comprises a substrate, element, or membrane to manipulate the scattering of light. In some embodiments, the analyte imaging device comprises a substrate, element, or membrane to manipulate the propagation of light.

In some embodiments, the analyte imaging device comprises a chip. In some embodiments, the analyte processing device comprises a cartridge. In some embodiments, the analyte imaging device comprises a replaceable cartridge. In some embodiments, the analyte imaging device comprises a replaceable or consumable element. In some embodiments, the chip is integrated with one or more photodetectors, the one or more excitation sources, one or more flow channels, one or more light scattering control elements, or any combination thereof. In some embodiments, the analyte processing device comprises a semiconductor chip. In some embodiments, the analyte processing device comprises a photonics chip. In some embodiments, the chip is integrated with one or more light modifying elements. In some embodiments, the chip is integrated with one or more light scattering control systems. In some embodiments, the analyte imaging device comprises one or more stacked layers. In some embodiments, the one or more stacked layers are integrated with a chip. In some embodiments, the analyte imaging device comprises one or more stacked layers integrated with a chip. In some embodiments, the chip may comprise several layers including but not limited to: an acoustophoresis layer, a microfluidic chamber layer, a microfluidic channel layer, a flow channel layer, a light modifying membrane layer, a photodetector layer, an excitation source layer, an optical circuit layer, a photonics circuit layer, or a light modifying substrate layer. In some embodiments, the optical circuit comprises one or more light entry sections, one or more optical dividers, a light delivery section, or any combination thereof. In some embodiments, the analyte imaging device comprises an energy source. In some embodiments, the energy source is a battery. In some embodiments, the energy source is integrated with the analyte imaging device. In some embodiments, the device comprises one or more excitation sources. In some embodiments, the one or more excitation sources provide excitation energy to the flow channel to yield the first optical signal, the second optical signal, or the third optical signal.

In some embodiments, the chip comprises an application specific integrated circuit. In some embodiments, the chip comprises an integrated circuit. In some embodiments, the chip is integrated with one or more other aspects of the analyte imaging device, including but not limited to: one or more flow channels, one or more light scattering control elements, a power source, one or more photodetectors, one or more excitation sources, or one or more displacement/phoresis elements, one or more circuits, or one or more chips. In some embodiments, the chip comprises an optical circuit. In some embodiments, readout circuitry may be operatively coupled to the analyte imaging device, wherein the readout circuitry is configured to transmit the data from the analyte imaging device to memory. In some embodiments, the flow channel is configured to result in displacement of the analyte. In some embodiments, the displacement is electrical. In some embodiments, the displacement is magnetic. In some embodiments, the analyte displacement is thermal. In some embodiments, the one or more photodetectors is configured for spectral range. In some embodiments, the one or more photodetectors is configured for photon intensity. In some embodiments, the one or more photodetectors is configured for photon wavelength. In some embodiments, the one or more photodetectors comprises a pinned photodiode. In some embodiments, the one or more photodetectors comprises a single photon avalanche diode. In some embodiments, the processing comprises time of flight processing.

Dimensions

A dimension of an object or analyte may be the subject of processing or analysis by devices disclosed herein. In some embodiments, the dimension comprises the volume. In some embodiments, the dimension comprises the shape. In some embodiments, the dimension comprises the position. In some embodiments, the dimension comprises the depth. In some embodiments, the dimension comprises the circumference. In some embodiments, the dimension comprises the thickness. In some embodiments, the dimension comprises the voltage. In some embodiments, the dimension comprises the velocity. In some embodiments, the dimension comprises the temperature. In some embodiments, the dimension comprises the frequency. In some embodiments, the processing is performed using Artificial Intelligence (AI). In some embodiments, the three-dimensional structure of the analyte comprises stretched representations of the analyte while the analyte passes through the space-constrained tube. In some embodiments, the stretched representations of the analyte are differently stretched. In some embodiments, the stretched representations of the analyte are identically stretched. In some embodiments, the stretched representations of the analyte determine elasticity. In some embodiments, the stretched representations of the analyte determine granularity.

Analytes

The devices described herein may be used to evaluate, identify, or process a wide variety of analytes of interest. In some embodiments, the analyte is a cell. In some embodiments, the analyte comprises an emulsion. In some embodiments, the analyte comprises a peptide. In some embodiments, the analyte comprises a small molecule. In some embodiments, the analyte comprises a conjugate molecule. In some embodiments, the analyte comprises a fluorescent molecule. In some embodiments, the analyte comprises an antigen. In some embodiments, the analyte comprises a lipid. In some embodiments, the analyte comprises a gaseous compound.

In some embodiments, the analyte comprises a biological sample. In some embodiments, the analyte comprises at least one cell. In some embodiments, the analyte is a population of cells. In some embodiments, the at least one cell is a mammalian cell, a eukaryotic cell, a yeast cell, a bacterial cell, a primary cell, an immortalized cell, a cancer cell, a hybrid cell, or a derivative or an engineered form thereof. In some embodiments, the analyte is blood. In some embodiments, the analyte is plasma. In some embodiments, the analyte is cerebrospinal fluid. In some embodiments, the analyte is lymph tissue. In some embodiments, the analyte is a specific type of cell from a subject. In some embodiments, the analyte is a specific type of cell that is from the brain, liver, heart, intestine, colon, muscle, kidney, pancreas, or other organ. In some embodiments, the analyte comprises skin cells, heart cells, immune system cells such as B-cells, lymphocytes, T-cells, kidney cells, liver cells, muscle cells, nervous system cells such as astral cells, glial cells, neuronal cells, bacterial cells, or peripheral blood mononuclear cells.

In some embodiments, the analyte is in the liquid phase. In some embodiments, the analyte is in the gas phase. In some embodiments, the analyte is an aqueous solution. In some embodiments, the analyte is solvated in an organic solution (e.g., acetone, methanol, acetonitrile, tetrahydrofuran, or other organic solvent). In some embodiments, the analyte is at least partially aerosolized. In some embodiments, the analyte is an aerosol. In some embodiments, the analyte motion is laminar motion. In some embodiments, the analyte motion is turbulent. In some embodiments, the analyte comprises one or more additional solutes. In some embodiments, the analyte further comprises a solvent that is phosphate buffered saline (PBS).

In some embodiments, the analyte is processed prior to analysis. In some embodiments, the analyte is reacted with a fluorophore, dye, labeling agent, or other similar chemical reagent. In some embodiments, the analyte is centrifuged prior to analysis. In some embodiments, the analyte is heated prior to analysis. In some embodiments, the analyte is cooled prior to analysis. In some embodiments, the analyte is frozen, or flash frozen, prior to analysis. In some embodiments, the analyte is a suspension. In some embodiments, the analyte is homogenous. In some embodiments, the analyte is heterogenous. In some embodiments, the analyte may be labelled with a fluorophore, a fluorescent molecule, a dye, or other similar moiety. In some embodiments, the analyte is at least one cell that may be labelled with a fluorophore or expresses a fluorescent molecule. In some embodiments, the analyte comprises at least once cell that may express a molecule including, but not limited, to a fluorescent molecule, a phosphorescent molecule, a chemiluminescent molecule, or a bioluminescent molecule. In some embodiments, the analyte comprises fluorophores that can be used as labels for specific target analytes, in applications where the targets can be chemically modified to incorporate a TGF fluorophore. Examples include, but are not limited to, Northern blots, Southern blots, DNA microarrays, quantitative Polymerase Chain Reaction (PCR), digital PCR, and diagnostic assays.

Flow Channel

Another aspect of the analyte processing device is the flow channel. In some embodiments, the analyte processing device comprises more than one flow channel. In some embodiments, the analyte processing device comprises more than two, more than four, more than eight, or more than 16 flow channels. In some embodiments, the analyte processing device comprises more than two, more than 64, more than 128, or more than 256 flow channels. In some embodiments, the flow channel comprises at least one outlet, at least two outlets, at least three outlets, or at least four outlets. In some embodiments, the flow channel comprises at least 16 outlets, at least 64 outlets, at least 128 outlets, at least 256 outlets, at least 1028 outlets. In some embodiments, the flow channel comprises at least one inlet, at least two inlets, at least three inlets, or at least four inlets. In some embodiments, the flow channel comprises at least 16 inlets, at least 64 inlets, at least 128 inlets, at least 256 inlets, at least 1028 inlets. In some embodiments, the flow channel is rectangular. In some embodiments, the flow channel is curved, indented, or similarly modified. In some embodiments, the flow channel is integrated with the analyte processing device. In some embodiments, the flow channel is configured to generate electrophoresis such as acoustophoresis, electrophoresis, or magnetophoresis. In some embodiments, the flow channel is configured to displace analytes within the flow channel. In some embodiments, the flow channel comprises one or more pumps. In some embodiments, the flow channel comprises one or more double-sided indents. In some embodiments, the flow channel comprises one or more single sided indents. In some embodiments, the flow channel comprises one or more single sided pinches. In some embodiments, the flow channel comprises one or more double sided pinches. In some embodiments, the flow channel comprises one or more curves. In some embodiments, the flow channel comprises one or more posts. In some embodiments, the flow channel comprises one or more bisections. In some embodiments, the flow channel comprises one or more intersections. In some embodiments, the flow channel comprises one or more convergence sections. In some embodiments, the flow channel comprises one or more bumps. In some embodiments, the flow channel comprises one or more posts. In some embodiments, the flow channel comprises one or more surface acoustic wave sources. In some embodiments, the flow channel comprises one or more flow channels. In some embodiments, the one or more flow channels comprise more than one analyte processing area. In some embodiments, the one or more excitation sources are integrated with the analyte processing device. In some embodiments, the one or more photodetectors are layered below the one or more flow channels. In some embodiments, the one or more flow channels are configured to rotate a cell on an axis. In some embodiments, the one or light scatter control elements comprise one or more diffractive optic layers. In some embodiments, the one or light scatter control elements comprise one or more light scattering control elements. In some embodiments, the one or light scatter control elements are integrated with the chip. In some embodiments, the flow channel comprises one or more features configured to displace the cell. In some embodiments, the flow channel comprises one or more chemical functionalizations. In some embodiments, the one or more chemical functionalizations are configured to interact with one or more analytes. In some embodiments, the one or more flow channels is configured to receive an acoustic wave, wherein the acoustic wave is configured to rotate the cell on an axis. In some embodiments, the flow channel comprises one or more features configured to rotate the cell on an axis. In some embodiments, the one or more flow channels are configured to contact a light scattering control system. In some embodiments, the one or more flow channels have a width configured to pass one cell at a time. In some embodiments, the width of the one or more flow channels is 100 nanometers.

In some embodiments, the flow channel comprises a gate. In some embodiments, the flow channel comprises one or more gates. In some embodiments, the flow channel comprises a sorting junction. In some embodiments, the flow channel comprises one or more sorting junction. In some embodiments, the flow channel comprises a series of sorting junctions. In some embodiments, the flow channel comprises one or more chambers. In some embodiments, the flow channel comprises more than five, more than 10, more than 50, or more than 100 chambers. In some embodiments, the flow channel comprises a fluid reservoir. In some embodiments, the flow channel comprises more than one fluid reservoir. In some embodiments, the flow channel comprises one or more pneumatically driven valves. In some embodiments, the flow channel comprises one or more fluid reservoirs. In some embodiments, the flow channel further comprises one or more peristaltic pumps. In some embodiments, the flow channel comprises Polydimethylsiloxane (PDMS). In some embodiments, the microfluidic channel comprises Polydimethylsiloxane (PDMS). In some embodiments, the flow channel comprises glass. In some embodiments, the microfluidic channel comprises glass. In some embodiments, the flow channel comprises plastic. In some embodiments, the microfluidic channel comprises plastic. In some embodiments, the flow channel comprises PMMA. In some embodiments, the microfluidic channel comprises PMMA. In some embodiments, the flow channel comprises polycarbonate. In some embodiments, the microfluidic channel comprises polycarbonate. In some embodiments, the microfluidic channel comprises a width of between about 10 µm to about 100 µm. In some embodiments, the microfluidic channel comprises a width of between about 10 µm to about 30 µm. In some embodiments, the microfluidic channel comprises a width of between about 1 µm to about 10 µm. In some embodiments, the microfluidic channel comprises a width of between about 0.1 µm to about 1.0 µm. In some embodiments, the microfluidic channel comprises a width of between about 0.01 µm to about 0.1 µm. In some embodiments, the microfluidic channel comprises a width of between about 0.001 µm to about 0.01 µm. In some embodiments, the microfluidic channel comprises a width of between about 0.001 µm to about 1.0 µm. In some embodiments, the microfluidic channel comprises a height of between about 10 µm to about 100 µm. In some embodiments, the microfluidic channel comprises a height of between about 10 µm to about 30 µm. In some embodiments, the microfluidic channel comprises a height of between about 1 µm to about 10 µm. In some embodiments, the microfluidic channel comprises a height of between about 0.1 µm to about 1.0 µm. In some embodiments, the microfluidic channel comprises a height of between about 0.01 µm to about 0.1 µm. In some embodiments, the microfluidic channel comprises a height of between about 0.001 µm to about 0.01 µm. In some embodiments, the microfluidic channel comprises a height of between about 0.001 µm to about 1.0 µm. In some embodiments, the microfluidic channel comprises a length of between about 10 µm to about 100 mm. In some embodiments, the microfluidic channel comprises a length of between about 10 µm to about 10 mm. In some embodiments, the microfluidic channel comprises a length of between about 1 µm to about 10 µm. In some embodiments, the microfluidic channel comprises a length of between about 0.1 µm to about 1.0 mm. In some embodiments, the microfluidic channel comprises a length of between about 0.01 µm to about 0.1 mm. In some embodiments, the microfluidic channel comprises a length of between about 0.001 µm to about 0.01 mm. In some embodiments, the microfluidic channel comprises a length of between about 0.001 µm to about 1.0 mm. In some embodiments, the one or more flow channels comprise multiple single inlets and a single outlet. In some embodiments, the one or more flow channels comprise multiple single inlets and a doublet outlet. In some embodiments, the one or more flow channels comprise a single inlet and multiple outlets.

In some embodiments, the flow channel comprises a feedback loop. In some embodiments, the flow channel comprises an inline pump. In some embodiments, the flow channel comprises a pump. In some embodiments, the flow channel comprises a cell injector. In some embodiments, the flow channel comprises a cell cartridge. In some embodiments, the flow channel comprises a cell collector. In some embodiments, the flow channel comprises a buffer reservoir. In some embodiments, the flow channel may branch in an 1×N pattern, where N is an integer greater than one. In some embodiments, the flow channel may branch in a series of 1×N patterns, where N is an integer greater than one.

In some embodiments, the analyte processing device comprises a substrate, element, or membrane to manipulate the scattering of light. In some embodiments, the analyte processing device comprises a substrate, element, or membrane to manipulate the propagation of light. In some embodiments, the flow channel comprises a light modifying system. In some embodiments, the flow channel comprises a light modifying substrate. In some embodiments, the flow channel comprises a light modifying element. In some embodiments, the light modifying element may be a dichroic optical component, a mirror, a membrane, a concentrator, a lens, a blocker, optical grating, a reflector, vertical couplers, lateral couplers, a filter, or a light entry section. In some embodiments, the analyte processing device comprises a light entry section. In some embodiments, the light entry section is a pinhole. In some embodiments, the light entry section comprises vertical couplers. In some embodiments, the light entry section comprises lateral couplers. In some embodiments, the light entry section comprises optical grating. In some embodiments, the light entry section comprises one or more dichroic optical components. In some embodiments, the filter is a dielectric material. In some embodiments, the filter is a metallic material. In some embodiments, the filter is a semiconductor material. In some embodiments, the filter is a combination of a dielectric, metallic, or semiconductor material, or combination thereof. In some embodiments, the filter comprises more than layer of filters. In some embodiments, the blocker comprises a layer of absorptive material configured to absorb specific light wavelengths. In some embodiments, the blocker comprises a layer of material configured to transmit specific wavelengths of light. In some embodiments, the blocker comprises a layer of material configured to transmit specific ranges of wavelengths of light. In some embodiments, the blocker comprises a layer of material configured to absorb specific ranges of wavelengths of light. In some embodiments, a blocker increases the signal to noise ratio by a factor of two. In some embodiments, a blocker increases the signal to noise ratio by a factor of at least two, at least 10, at least 100, at least 1,000, or at least 10,000. In some embodiments, the concentrator comprises a lens. In some embodiments, the lens is a microlens, a flat lens, a diffractive lens, an absorptive lens, or a non-absorptive lens. In some embodiments, the concentrator is a dielectric block. In some embodiments, the dielectric block is at least 100 nanometers thick. In some embodiments, dielectric block is at least 1 micrometer thick. In some embodiments, the mirror is configured to improve the coupling efficiency of vertical couplers. In some embodiments, the reflector is configured to improve the coupling efficiency of vertical couplers. In some embodiments, the mirror is configured to improve the coupling efficiency of lateral couplers. In some embodiments, the reflector is configured to improve the coupling efficiency of lateral couplers. In some embodiments, the one or more flow channels is configured to generate a displacement effect on an analyte located in the at least one flow channel, thereby selectively displacing the analyte in the one or more analyte processing areas. In some embodiments, the displacement is acoustical. In some embodiments, the displacement is electrical. In some embodiments, the displacement is magnetic. In some embodiments, the displacement is caused by a fluid wave. In some embodiments, the displacement is caused by a structure of a flow channel. In some embodiments, the displacement is caused by a density wave. In some embodiments, the displacement is via droplet displacement. In some embodiments, the one or more flow channels further comprises a gate. In some embodiments, the one or more flow channels further comprises a sealable chamber. In some embodiments, the one or more flow channels further comprises one or more pneumatically driven valves. In some embodiments, the one or more flow channels further comprises one or more fluid reservoirs. In some embodiments, the one or more flow channels further comprises one or more peristaltic pumps. In some embodiments, the one or more flow channels are a space-constrained tube relative to the analyte.

Excitation Sources

Several arrangements are possible to yield an excitation within the context of the analyte processing device described herein. In some embodiments, the device comprises one excitation source. In some embodiments, the device comprises more than one, more than two, more than three, more than four, or more than five excitation sources. In some embodiments, the device comprises at least 10, at least 20, at least 30, or at least 40 excitation sources. In some embodiments, the device comprises one or more excitation sources integrated with the device. In some embodiments, the device comprises one or more excitation sources integrated with a chip. In some embodiments, the one or more excitation sources comprises a photon array. In some embodiments, the one or more excitation sources comprises one or more photon arrays. In some embodiments, the one or more excitation sources comprises a waveguide. In some embodiments, the one or more excitation sources are configured to yield specific wavelengths of lights. In some embodiments, the one or more excitation sources comprises an interposer. In some embodiments, the one or more excitation sources comprises a transducer. In some embodiments, the one or more excitation sources comprises a laser. In some embodiments, the one or more excitation sources comprises an integrated circuit. In some embodiments, the one or more excitation sources comprises an interposer. In some embodiments, the excitation source comprises a transducer. In some embodiments, the excitation source comprises an interposer. In some embodiments, the excitation source comprises more than one interposer. In some embodiments, the excitation source comprises a transducer. In some embodiments, the excitation source comprises one or more transducers. In some embodiments, the excitation source comprises a laser. In some embodiments, the excitation source comprises more than one laser, more than 10 lasers, more than 100 lasers, or more than 1,000 lasers. In some embodiments, the laser is a bonded laser. In some embodiments, the laser is an external laser. In some embodiments, the laser is a continuous laser. In some embodiments, the laser is a pulsed laser. In some embodiments, the one or more lasers are a tunable laser. In some embodiments, the one or more excitation sources is configured to generate a light wavelength between 300 nm and 1,200 nm. In some embodiments, the one or more excitation sources is configured to generate a light with a height between at least 80 nm and at most 200 nm. In some embodiments, the one or more excitation sources is configured to generate light intensity of at least 1 $\mu W/\mu m^2$. In some embodiments, the one or more excitation sources generates a light intensity of less than 10 1 $\mu W/\mu m^2$. In some embodiments, at least one of the one or more excitation sources is a reference excitation source. In some embodiments, the one or more excitation sources is integrated with the analyte processing device. In some embodiments, the one or more photodetectors is integrated with the analyte processing device. In some embodiments, the one or more excitation sources further comprise a waveguide.

In some embodiments, the one or more lasers are integrated with a chip. In some embodiments, the excitation source is integrated with a chip. In some embodiments, the chip is integrated with one flow channel. In some embodiments, the chip is integrated with more than one flow channel. In some embodiments, the chip is integrated with a phoresis mechanism. In some embodiments, the chip is integrated with one or more excitation sources. In some embodiments, the chip is integrated with one or more microfluidic channels. In some embodiments, the chip is integrated with one or more micro-optics components. In some embodiments, the chip is integrated with one or more photonic circuits. In some embodiments, the chip is integrated with one or more CMOS photodetectors. In some embodiments, the chip is integrated with one or more photodetectors. In some embodiments, the chip is integrated with one or more light scattering control elements. In some embodiments, the semiconductor chip comprises a power source, one or more controllers, one or more readouts, and one or more photodetector pixels.

In some embodiments, the excitation source comprises a waveguide. In some embodiments, the excitation source comprises an optical waveguide. In some embodiments, the optical waveguide may branch in an 1×N pattern, where N is an integer greater than one. In some embodiments, the optical waveguide comprises more than one branching point. In some embodiments, the optical waveguide may comprise one or more 1×2 branching points. In some embodiments, the excitation source is configured to excite light at specific wavelengths. In some embodiments, the excitation source is configured to excite light at specific ranges of light wavelengths. In some embodiments, the excitation source is configured to excite light in the ultraviolet range. In some embodiments, the excitation source is configured to excite light in the microwave range. In some embodiments, the excitation source is configured to excite light in the IR to visible light range. In some embodiments, the excitation source comprises a pinhole for light entry. In some embodiments, the excitation source comprises an optical circuit. In some embodiments, the optical circuit comprises one or more light entry sections.

In some embodiments, the excitation source is programmed to generate an evanescent light field. In some embodiments, the excitation source is programmed to generate a superposition of light fields. In some embodiments, the excitation sources are programmed to synchronize with other elements of the analyte processing device sources. In some embodiments, the one or more excitation sources are programmed to synchronize with other excitation sources. In some embodiments, the one or more excitation sources further comprise an interposer. In some embodiments, the one or more excitation sources further comprise a transducer. In some embodiments, the transducer is integrated into the chip. In some embodiments, the transducer is external to the chip. In some embodiments, the one or more excitation sources comprise one laser. In some embodiments, the one or more excitation sources comprises one or more light emitting diodes (LED). In some embodiments, the LED is a micro LED. In some embodiments, the one or more excitation sources comprise multiple lasers. In some embodiments, the one or more excitation sources comprise external lasers. In some embodiments, the one or more excitation sources comprise bonded lasers. In some embodiments, the one or more excitation sources comprise at least one continuous laser. In some embodiments, the one or more excitation sources comprise at least one pulsed laser. In some embodiments, the one or more excitation sources comprise at least one tunable laser. In some embodiments, the one or more excitation sources comprise at least one laser tuned to near IR to visible range wavelengths of light.

Photodetectors

In some aspects of the disclosure herein, the analyte processing area is configured to enable photodetectors to yield high resolution images of an analyte. In some cases, the analyte processing device comprises one photodetector. In some cases, the analyte processing device comprises more than one photodetector, more than two photodetectors, more than four photodetectors, more than eight photodetectors, or more than 16 photodetectors. In some cases, the analyte processing device comprises more than 32 photodetector, more than 64 photodetectors, more than 128 photodetectors, more than 256 photodetectors, or more than 512 photodetectors. In some embodiments, the photodetector comprises a semiconductor imager. In some embodiments, the photodetector comprises one or more semiconductor imagers. In some embodiments, the photodetector comprises a pixel. In some embodiments, the photodetector comprises more than one pixel. In some embodiments, the photodetector comprises more than 10, more than 100, more than 1,000 or more than 10,000 pixels. In some embodiments, the photodetectors are positioned 10 microns apart from each other. In some embodiments, the photodetectors are positioned 15 microns apart from each other. In some embodiments, the photodetectors are positioned 20 microns apart from each other. In some embodiments, the photodetectors are positioned at least 5 microns apart from each other. In some embodiments, the photodetectors are positioned at least 10 microns apart from each other. In some embodiments, the photodetectors are positioned at least 20 microns apart from each other. In some embodiments, the photodetector comprises one or more pixels. In some embodiments, the photodetector pixel size is 10 microns by 10 microns. In some embodiments, the photodetector pixel size is 20 microns by 10 microns. In some embodiments, the photodetector pixel size is 20 microns by 20 microns. In some embodiments, a photodetector may comprise a camera or camera-like detector with a square, rectangular, or linear array of pixels. In some embodiments, the photodetector may be spatially arranged in a specific manner. In some embodiments, the analyte processing device comprises one photodetector station. In some embodiments, the analyte processing device comprises at least 2, at least 4, at least 8, at least 16, or at least 64 photodetector stations. In some embodiments, the analyte processing device comprises at least 128, at least 512, or at least 1028 photodetector stations. In some embodiments, the one or more photodetectors comprise a single photodetector pixel. In some embodiments, the one or more photodetector pixels are 10 microns by 10 microns in size. In some embodiments, the one or more photodetector pixels are 20 microns by 20 microns in size. In some embodiments, the one or more photodetector pixels are 20 microns by 10 microns in size. In some embodiments, the analyte processing device comprises two or more photodetectors, wherein the two or more photodetectors are positioned 20 microns apart from one another. In some embodiments, the one or more excitation sources in optical communication with the analyte processing area comprises an optical path from the one or more excitation sources to the analyte processing area, the optical path comprising a light scattering control system.

In some cases, one or more photodetectors are located on the bottom of the flow channel. In some cases, one or more photodetectors are located on the side of the flow channel. In some cases, one or more photodetectors are located on the top of the flow channel. In some embodiments, one or more photodetectors covers a section of the flow channel surface. In some embodiments, the photodetector comprises a complementary metal oxide sensor (CMOS) imager. In some embodiments, the photodetector comprises one or more complementary metal oxide sensor (CMOS) imagers. In some embodiments, the photodetector comprises a CMOS imager configured to flush electrons generated with scattered light upon excitation. In some embodiments, the photodetector comprises a spectral CMOS imager. In some embodiments, the photodetector comprises a CMOS imager configured for photon wavelength. In some embodiments, the photodetector comprises a CMOS imager configured for photon intensity. In some embodiments, the photodetector comprises a pinned photodiode CMOS imager. In some embodiments, the photodetector comprises a single-photon avalanche diode CMOS imager. In some embodiments, the one or more photodetectors comprise a complementary metal oxide sensor (CMOS) imager. In some embodiments, the CMOS imager is configured to flush electrons generated with scattered light upon excitation. In some embodiments, the CMOS imager is spectral. In some embodiments, the CMOS imager is configured for photon intensity. In some embodiments, the CMOS imager is configured for photon wavelength. In some embodiments, the CMOS imager is a pinned photodiode. In some embodiments, the CMOS imager is a single photon avalanche diode array. In some embodiments, the CMOS imager comprises one or more arrays of single photon avalanche diodes. In some embodiments, the CMOS imager further comprises one or more event cameras. In some embodiments, the CMOS imager further comprises one or more time-delay integration (TDI) camera.

In some embodiments, the one or more photodetectors forms an optical path with the analyte processing area. In some embodiments, the one or more photodetectors forms an optical path with one or more analyte processing areas. In some embodiments, the one or more photodetectors forms one or more optical paths with the analyte processing area.

In some embodiments, the optical path comprises light modifying substrates, layers, or elements. In some embodiments, the optical path comprises a light entry section, an optical circuit, optical grating, a reflector, vertical couplers, lateral couplers, a filter, a blocker, a concentrator, a mirror, or an optical membrane. In some embodiments, the optical path comprises one or more light modifying substrates, layers, or elements. In some embodiments, the one or more photodetectors are configured to simultaneously collect the one or more two-dimensional images. In some embodiments, the one or more photodetectors are configured to simultaneously collect the one or more two-dimensional images. In some embodiments, the one or more photodetectors are configured to collect the one or more two-dimensional images without the use of markers or labels. In some embodiments, the one or more photodetector(s) comprises at least one of: a spectral detector, an emissions detector, or a scattering detector. In some embodiments, the analyte processing device comprises at least one emissions detector and at least one scattering detector. In some embodiments, the one or more two-dimensional images determines the absolute or relative size of the analyte. In some embodiments, the three-dimensional structure of the analyte maps the surface of the analyte. In some embodiments, the three-dimensional structure of the analyte comprise deformed representations of the analyte. In some embodiments, the deformed representations of the same analyte represent different deformations. In some embodiments, the deformed representations of the analyte represent an unchanged deformation.

In some embodiments, the one or more photodetectors comprises one or more single-photon avalanche diode (SPAD) arrays. In some embodiments, the one or more photodetectors comprise a single-photon avalanche diodes (SPAD) array. In some embodiments, the one or more photodetectors comprise one or more silicon photomultipliers (SiPM). In some embodiments, the one or more two-dimensional images comprises 1 pixel. In some embodiments, the one or more two-dimensional images has a 1:1 aspect ratio of the analyte. In some embodiments, the one or more two-dimensional images each depict an area on a surface of the analyte having a length of from 0.5 microns to 100 microns and a width from 0.5 microns to 100 microns, and a width being equal to or smaller than the length. In some embodiments, the one or more two-dimensional images having the 1:1 aspect ratio are combined with separate two-dimensional images of the same analyte with the same aspect ratio to produce the three-dimensional structure of an analyte. In some embodiments, the aspect ratios from the one or more two-dimensional images with the 1:1 aspect ratio are combined with separate two-dimensional images with different aspect ratios when producing the three-dimensional structure of one or more analytes. In some embodiments, the three-dimensional structure depicts a holistic distribution of surface markers of the one or more analytes. In some embodiments, the holistic distribution of surface markers can be defined as localized or partial. In some embodiments, the holistic distribution of surface markers can be defined as random. In some embodiments, the holistic distribution of surface markers can determine a parameter of a chemical or biological test. In some embodiments, a defined stretch or a deformation can determine a false positive for a chemical or biological test. In some embodiments, the parameter of a chemical or biological test can separate a false positive from a true positive. In some embodiments, the light scattering control system is configured to improve signal to noise ratio by at least a factor of five relative to photodetecting only unscattered or specular light.

Analyte Processing Area

The analyte processing area may comprise multiple individual sections or elements to optimize imaging under specific circumstances. The analyte processing area may also be geometrically arranged to optimize imaging under a useful circumstance. In some embodiments, the analyte processing device comprises one or more analyte processing areas. In some embodiments, the analyte processing area forms an optical path with the one or more excitation sources. In some embodiments, the analyte processing area forms an optical path with the one or more photodetectors. In some embodiments, the analyte processing area may be between a sorting junction and a gate. In some embodiments, the analyte processing area may be between more than one sorting junction or more than one gate. In some embodiments, the analyte processing area comprises a light scattering control system. In some embodiments, the analyte processing area comprises a light scattering control element. In some embodiments, the analyte processing area comprises one or more light scattering control elements. In some embodiments, the analyte processing area comprises an optical membrane. In some embodiments, the analyte processing area comprises a light modifying substrate or light modifying element. In some embodiments, the analyte processing area comprises an optical membrane. In some embodiments, the analyte processing area comprises a layer of light modifying substrates. In some embodiments, the flow channel comprises an analyte processing area. In some embodiments, the flow channel comprises one or more analyte processing areas. In some embodiments, the analyte processing area is at the bottom surface. In some embodiments, the analyte processing area is at the top surface. In some embodiments, the analyte processing area is on the side of the surface. In some embodiments, the analyte processing area comprises one or more diffractive optic layers. In some embodiments, the analyte processing area is adjacent to one or more diffractive optic layers. In some embodiments, the analyte processing area is adjacent to a diffractive optic layer. In some embodiments, the analyte processing area is above one or more photodetectors. In some embodiments, the analyte processing area is above one or more light modifying substrates. In some embodiments, the analyte processing area is located at a bottom surface of one or more flow channels.

Figure 22:
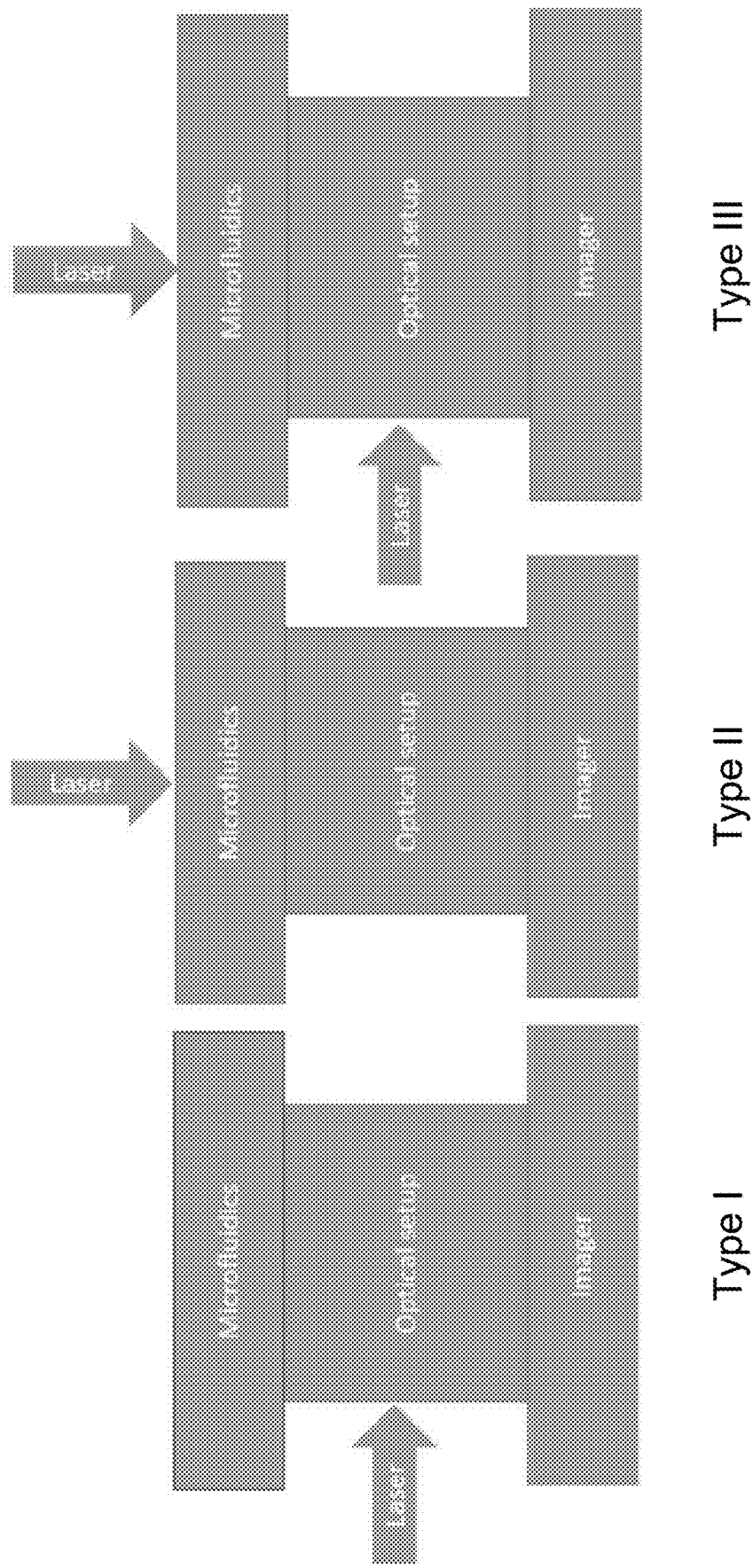
FIG. 22 shows three optical arrangements of devices described herein.
Figure 23:
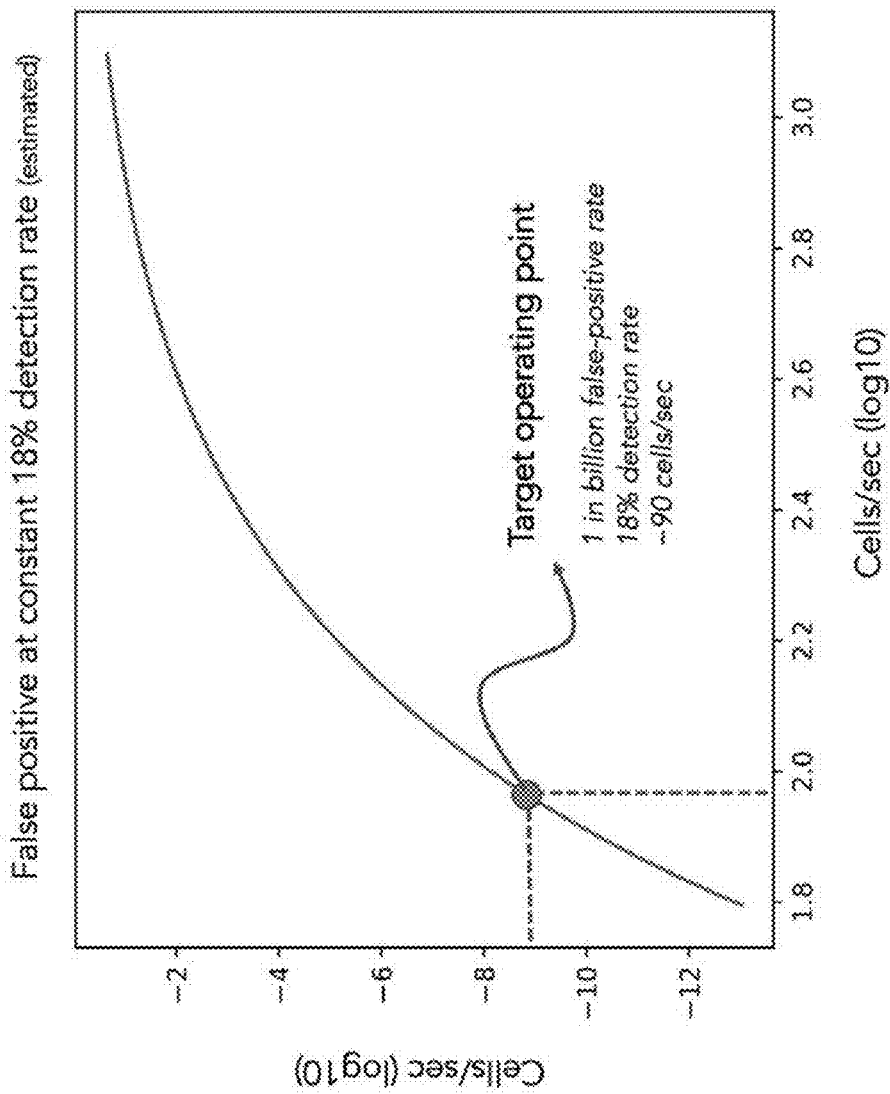
FIG. 23 shows an example of operating capability of devices described herein.

In some embodiments, the microfluidic channel is arranged as shown in FIG. 22. In some embodiments, the microfluidic channel is arranged as shown in Type I of FIG. 22. In some embodiments, the microfluidic channel is arranged as shown in Type II of FIG. 22. In some embodiments, the microfluidic channel is arranged as shown in Type III of FIG. 22. In some embodiments, the analyte processing area comprises a photomultiplier tube.

Analytes

In some embodiments, the analyte comprises multiple analytes comprising at least one of: small molecules, polymers, cellular structures, or surface markers. In some embodiments, the multiple analytes comprise materials from biological systems. In some embodiments, the materials from biological systems comprise cells or internal cell organelles. In some embodiments, the multiple analytes comprise free floating or secreted proteins. In some embodiments, the multiple analytes comprise a nucleotide. In some embodiments, the multiple analytes comprise or are contained within exosomes. In some embodiments, the multiple analytes comprise or are contained within neutrophils. In some embodiments, the multiple analytes comprise nucleotides. In some embodiments, the multiple analytes are extravesicular. In some embodiments, the three-dimensional structures of each of the multiple analytes is analyzed individually. In some embodiments, the three-dimensional structure of each of the multiple analytes may produce a new three-dimensional structure of an additional, larger analyte. In some embodiments, structural integrity of the multiple analytes is preserved after displacement in the one or more flow channels. In some embodiments, the surface markers comprise cell surface markers. Many analytes of interest may be characterized by the analyte processing device. In some embodiments, the analyte is singular. In some embodiments, the analyte comprises a population. In some embodiments, the analyte is an inorganic chemical. In some embodiments, the analyte is an organic chemical. In some embodiments, the analyte is a peptide, small molecule, drug molecule, drug-conjugate molecule, dye molecule, dye-conjugate molecule, fluorescent molecule, or any other organic chemicals of interest.

In some embodiments, the analyte can comprise a biological sample. In some embodiments, the analyte comprises at least one cell. In some embodiments, the analyte is a population of cells. In some embodiments, the at least one cell may be a mammalian cell, a eukaryotic cell, a yeast cell, a bacterial cell, a primary cell, an immortalized cell, a cancer cell, a hybrid cell, or a derivative or an engineered form thereof. In some embodiments, the analyte is blood. In some embodiments, the analyte is plasma. In some embodiments, the analyte is cerebrospinal fluid. In some embodiments, the analyte is lymph tissue. In some embodiments, the analyte is a specific type of cell from a subject. In some embodiments, the specific type of cell is from the brain, liver, heart, intestine, colon, muscle, kidney, pancreas, or other organ. In some embodiments, the analyte comprises skin cells, heart cells, immune system cells such as B-cells, lymphocytes, T-cells, kidney cells, liver cells, muscle cells, nervous system cells such as astral cells, glial cells, neuronal cells, bacterial cells, or peripheral blood mononuclear cells.

In some embodiments, the analyte is in the liquid phase. In some embodiments, the analyte is in the gas phase. In some embodiments, the analyte is an aqueous solution. In some embodiments, the analyte is solvated in an organic solution (e.g., acetone, methanol, acetonitrile, tetrahydrofuran, or other organic solvent). In some embodiments, the analyte is at least partially aerosolized. In some embodiments, the analyte is an aerosol. In some embodiments, the motion of the analyte is laminar. In some embodiments, the analyte motion is turbulent. In some embodiments, the analyte comprises one or more additional solutes. In some embodiments, the solvent is phosphate buffered saline (PBS). In some embodiments, the analyte motion is laminar. In some embodiments, the analyte motion is turbulent. In some embodiments, the analyte is not in motion. In some embodiments, the analyte is an aerosol. In some embodiments, the analyte is in the gas phase. In some embodiments, the analyte is in the liquid phase. In some embodiments, the analyte is an aqueous solution. In some embodiments, the analyte comprises one or more cells. In some embodiments, the analyte comprises blood. In some embodiments, the analyte comprises lymph. In some embodiments, the analyte comprises a cell line. In some embodiments, the analyte comprises a cell culture. In some embodiments, the analyte comprises a human cell. In some embodiments, the analyte comprises a bacterial cell. In some embodiments, the analyte comprises urine. In some embodiments, the analyte comprises bodily fluids. In some embodiments, the analyte comprises feces. In some embodiments, the analyte comprises peritoneal cavity fluid. In some embodiments, the analyte comprises bone marrow fluid. In some embodiments, the analyte comprises cerebrospinal fluid. In some embodiments, the analyte comprises cells purified from a subject's blood sample. In some embodiments, the analyte comprises blood serum or plasma.

In some embodiments, the analyte is processed prior to analysis. In some embodiments, the analyte is reacted with a fluorophore, dye, labeling agent, or other similar chemical reagent. In some embodiments, the analyte is centrifuged prior to analysis. In some embodiments, the analyte is heated prior to analysis. In some embodiments, the analyte is cooled prior to analysis. In some embodiments, the analyte is frozen, or flash frozen, prior to analysis. In some embodiments, the analyte is a suspension. In some embodiments, the analyte is homogenous. In some embodiments, the analyte is heterogenous. In some embodiments, the analyte may be labelled with a fluorophore, a fluorescent molecule, a dye, or other similar moiety. In some embodiments, at least one cell may be labelled with a fluorophore or expresses a fluorescent molecule. In some embodiments, at least once cell may express a molecule including, but not limited, to a fluorescent molecule, a phosphorescent molecule, a chemiluminescent molecule, or a bioluminescent molecule. In some embodiments, fluorophores can be used as labels for specific target analytes, in applications where the targets can be chemically modified to incorporate a TGF fluorophore. Examples includes, but are not limited to, Northern blots, Southern blots, DNA microarrays, quantitative Polymerase Chain Reaction (PCR), digital PCR, and diagnostic assays.

Optical Paths

Acquisition of optical signals is possible by optical communication within the analyte processing device described herein. Optical communication may be partially characterized by the optical path between an analyte of interest and one or more photodetectors. In some embodiments, optical communication comprises an optical path between an analyte of interest, one or more excitation sources, and one or more photodetectors. In some embodiments, optical communication comprises an optical path between one or more analytes of interest, one or more excitation sources, and one or more photodetectors. In some embodiments, the optical path is configured to yield an evanescent light beam from the one or more excitation sources.

In some embodiments, the analyte processing device comprises an optical path. In some embodiments, the optical path is formed between one or more excitation sources and an analyte. In some embodiments, the optical path is formed between one or more photodetectors and the analyte processing area. In some embodiments, the optical path is formed between one or more photodetectors, one or more excitation sources, and an analyte. In some embodiments, the optical path is formed between one or more photodetectors and the analyte processing area. In some embodiments, the optical path comprises a light scattering control element. In some embodiments, the light scattering control element comprises a layer of material. In some embodiments, the material comprises one or more of the following: $SiO_2$, TiN, Ti, $Si_3N_4$, silicon oxynitride (SiOxNy), TaO, HfO, Si, glass, or other similar material or oxide.

In some embodiments, the optical path between the photodetector and the analyte processing area comprises a light scattering control element. In some embodiments, the optical path comprises a lens, concentrator, dielectric, dichroic, reflector, or mirror. In some embodiments, the optical path comprises elements configured to redirect scattered light distal from a photodetector. In some embodiments, the optical path comprises elements configured to redirect scattered light distal from one or more photodetectors. In some embodiments, the optical path comprises more than one element configured to redirect scattered light distal from a photodetector. In some embodiments, the optical path comprises a dichroic optical component configured to redirect scattered light distal from one or more photodetectors. In some embodiments, the optical path comprises more than one membrane. In some embodiments, the optical path comprises a light modifying membrane. In some embodiments, the optical path comprises an angle relative to an analyte. In some embodiments, the optical path comprises an angle relative to the light modifying element. In some embodiments, the optical path comprises an angle relative to the light modifying substrate. In some embodiments, the optical path comprises an angle relative to the light modifying layer. In some embodiments, the light scattering control element comprises one or more layers of the following: $SiO_2$, TiN, Ti, $Si_3N_4$, silicon oxynitride (SiOxNy), TaO, HfO, Si, glass, or other similar material or oxide. In some embodiments, the light modifying substrate comprises one or more layers of the following: $SiO_2$, TiN, Ti, $Si_3N_4$, silicon oxynitride (SiOxNy), TaO, HfO, Si, glass, or other similar material or oxide. In some embodiments, the optical path forms an angle of at least 10, at least 20, at least 30, at least 40, at least 50, at least 60, at least 70, at least 80, or at least 90 degrees with the one or more light scattering control elements.

Light Scattering Control System

In order to diversify approaches to imaging analytes, the analyte processing device may comprise a particular light scattering control system. In some embodiments, the light scattering control system comprises an optical membrane comprising a polarizer, waveplate, absorber, filter, blocker, concentrator, reflector, or mirror. In some embodiments, the one or more photodetectors comprise a shutter configured to reduce overexposure of light. In some embodiments, the light scattering control system is configured to optimize signal to noise ratio of an analyte. In some embodiments, the light scattering control system is configured to optimize light propagation. In some embodiments, the light scattering control system is configured to optimize evanescent light propagation. In some embodiments, the light scattering control system is configured to propagate evanescent light. In some embodiments, the light scattering control system is configured to shutter excess light excitation within the analyte processing device. In some embodiments, the light scattering control system is configured to reduce excess light propagation. In some embodiments, the light scattering control system is configured to optimize angular light propagation. In some embodiments, the light scattering control system comprises a light modifying element. In some embodiments, the light scattering control system comprises one or more light modifying elements.

The light scattering control systems are capable of increasing the sensitivity of imaging. In some embodiments, the measurement sensitivity achieved through the light scatter control system is at least a factor of two. In some embodiments, the sensitivity increase is at least a factor of 10, at least a factor of 100, at least a factor of 1,000, at least a factor of 10,000, or at least a factor 100,000. In some embodiments, the light scattering control systems increase the signal to noise ratio by at least a factor of two, a factor of five, a factor of 10, a factor of 100, a factor of 1,000, or a factor of 10,000. In some embodiments, the signal to noise ratio is improved by reducing excess electrons. In some embodiments, the signal to noise ratio is improved by signal correlation between more than two or more photodetectors. In some embodiments, signal to noise ratio is improved by an evanescent light field. In some embodiments, signal to noise ratio is improved by imaging modality. In some embodiments, the noise is reduced from light scattering within a waveguide. In some embodiments, the noise is reduced from light scattering due to photonics structure. In some embodiments, the noise is reduced from light scattering due to an integrated circuit. In some embodiments, the noise is reduced from light scattering due to an application specific integrated circuit. In some embodiments, the noise is reduced from light scattering due to light scattering from one or more analytes. In some embodiments, the noise is reduced from light scattering due to flow channel structure. In some embodiments, the noise is reduced from light scattering due to microfluidic channel walls. In some embodiments, the noise is reduced from light scattering due to photodetector structure. In some embodiments, the light scattering control system comprises a dichroic optical component configured to redirect scattered light distal from the one or more photodetectors. In some embodiments, the light scattering control system is configured to improve signal to noise ratio by at least a factor of five. In some embodiments, the filter is comprised of at least one layer of dielectric material configured to absorb unwanted light wavelengths and improve signal to noise ratio by a factor of at least five. In some embodiments, the filter is comprised of at least one layer of semiconductor material configured to absorb unwanted light wavelengths and improve signal to noise ratio by a factor of at least five. In some embodiments, the filter is comprised of at least one layer of metallic material configured to absorb unwanted light wavelengths and improve signal to noise ratio by a factor of at least five. In some embodiments, the filter is comprised of at least two layers of dielectric, semiconductor, or metallic material configured to absorb unwanted light wavelengths and improve signal to noise ratio by a factor of at least 5. In some embodiments, the blocker comprises a layer of absorptive material configured to transmit specific wavelengths. In some embodiments, the blocker is tuned to absorb specific photonic wavelength ranges. In some embodiments, the filter is comprised of at least two layers of dielectric, semiconductor, or metallic material configured to absorb unwanted light wavelengths and improve signal to noise ratio. In some embodiments, the filter is comprised of a polarizing light filter. In some embodiments, the blocker comprises a layer of absorptive material configured to transmit specific wavelengths of light. In some embodiments, the blocker is tuned to absorb specific photonic wavelength ranges. In some embodiments, the concentrator is a microlens concentrator. In some embodiments, the concentrator comprises a flat lens concentrator. In some embodiments, the concentrator comprises a diffractive lens. In some embodiments, the concentrator comprises an absorptive lens. In some embodiments, the concentrator comprises a non-absorptive lens. In some embodiments, the concentrator comprises a polarization sensitive lens. In some embodiments, the concentrator comprises a dielectric. In some embodiments, the concentrator comprises a dielectric block. In some embodiments, the concentrator comprises a dielectric block at least 100 nanometers thick. In some embodiments, the concentrator comprises a dielectric block at least one micrometer thick. In some embodiments, the one or more excitation sources comprise an optical circuit comprising one or more light entry sections, one or more optical dividers, and a light delivery section. In some embodiments, the light delivery section further comprises one or more dichroic optical components configured to redirect scattered light away from the light delivery section. In some embodiments, the light entry section comprises vertical couplers. In some embodiments, the light entry section comprises optical grating. In some embodiments, the light entry section further comprises a lateral coupler. In some embodiments, the light entry section is a pinhole. In some embodiments, the reflector is configured to improve the coupling efficiency of the vertical couplers. In some embodiments, the mirror is configured to improve the coupling efficiency of vertical couplers.

Light Scattering Control Elements

Light scattering control elements can individually and synergistically yield a favorable effect on physical characterization of analytes in a flow channel. In some embodiments, the analyte processing device comprises a light scattering control element, which may form part of a broader light scattering control system. In some embodiments, the analyte processing device comprises one or more light scattering control systems. In some embodiments, the analyte processing device comprises one or more light scattering control elements. In some embodiments, the optical path comprises a light scattering control element. In some embodiments, the optical path comprises one or more light scattering control elements. In some embodiments, the light scattering control element comprises a lens, a concentrator, mirror, reflector, optical grating, blocker, coupler, or absorptive material. In some embodiments, the light scattering control element comprises a micro-interferogram element (MIE). In some embodiments, the one or more light scatter control elements reduces the signal to noise ratio of one or more optical signals emitted from the chip by at least a factor of 10.

In some embodiments, the one or more light scattering control elements comprise a light entry section. In some embodiments, the light entry section is a pinhole. In some embodiments, the light entry section comprises vertical couplers. In some embodiments, the light entry section comprises lateral couplers. In some embodiments, the light entry section comprises optical grating. In some embodiments, the light entry section comprises one or more dichroic optical components. In some embodiments, the filter is a dielectric material. In some embodiments, the filter is a metallic material. In some embodiments, the filter is a semiconductor material. In some embodiments, the filter is a combination of a dielectric, metallic, or semiconductor material, or combination thereof. In some embodiments, the filter comprises more than layer of filters. In some embodiments, the blocker comprises a layer of absorptive material configured to absorb specific light wavelengths. In some embodiments, the blocker comprises a layer of material configured to transmit specific wavelengths of light. In some embodiments, the blocker comprises a layer of material configured to transmit specific ranges of wavelengths of light. In some embodiments, the blocker comprises a layer of material configured to absorb specific ranges of wavelengths of light. In some embodiments, a blocker increases the signal to noise ratio by a factor of two. In some embodiments, a blocker increases the signal to noise ratio by a factor of at least two, at least 10, at least 100, at least 1,000, or at least 10,000. In some embodiments, the concentrator comprises a lens. In some embodiments, the lens is a microlens, a flat lens, a diffractive lens, an absorptive lens, or a non-absorptive lens. In some embodiments, the concentrator is a dielectric block. In some embodiments, the dielectric block is at least 100 nanometers thick. In some embodiments, dielectric block is at least 1 micrometer thick. In some embodiments, the mirror is configured to improve the coupling efficiency of vertical couplers. In some embodiments, the reflector is configured to improve the coupling efficiency of vertical couplers. In some embodiments, the mirror is configured to improve the coupling efficiency of lateral couplers. In some embodiments, the reflector is configured to improve the coupling efficiency of lateral couplers. In some embodiments, the light scattering control elements are integrated with the analyte processing device. In some embodiments, the light scattering control elements are adjacent to one or more photodetectors. In some embodiments, the light scattering control elements are on a surface on one or more flow channels. In some embodiments, the light scattering control elements comprise a diffractive optic layer. In some embodiments, the light scattering control elements are between one or more photodetectors and one or more flow channels. In some embodiments, the one or more flow channels is above the one or more light scattering control elements. In some embodiments, the light scattering control elements are configured to send and receive one or more photons to and from the one or more flow channels. In some embodiments, the diffractive optic layer is configured to send and receive one or more photons to and from the one or more flow channels. In some embodiments, one or more photodetectors is configured to receive one or more photons from the diffractive optic layer. In some embodiments, the one or more photodetectors is configured to receive one or more photons from the light scattering control elements. In some embodiments, the flow channels are configured to receive one or more photons from the light scattering control elements. In some embodiments, the light modifying substrate is displaced between the one or more photodetectors and the one or more flow channels. In some embodiments, the light modifying substrate comprises a diffractive optic layer. In some embodiments, the light modifying substrate is displaced between the one or more photodetectors and the one or more flow channels. In some embodiments, a diffractive optic layer is displaced between the one or more photodetectors and the one or more flow channels. In some embodiments, the one or more flow channels are displaced on or above the diffractive optic layer. In some embodiments, the light modifying substrate is configured to send and receive one or more photons to and from the one or more flow channels. In some embodiments, the diffractive optic layer is configured to send and receive one or more photons to and from the one or more flow channels. In some embodiments, the one or more photodetectors is configured to receive one or more photons from the light modifying substrate. In some embodiments, the one or more photodetectors is configured to receive one or more photons from the diffractive optic layer.

Chips

In some embodiments, disclosed herein are chips, which may be separate structures from the analyte imaging device or analyte processing device. In some embodiments, the chip forms a layer of an analyte imaging device or analyte processing device. In some embodiments, provided herein is a chip comprising one or more flow channels, wherein the one or more flow channels comprise one or more light scatter control elements adjacent to one or more analyte processing areas. In some embodiments, the one or more flow channels are configured to rotate a cell on an axis. In some embodiments, the one or light scatter control elements comprise one or more diffractive optic layers. In some embodiments, the one or light scatter control elements comprise one or more light scattering control elements. In some embodiments, the one or light scatter control elements are integrated with the chip. In some embodiments, the flow channel comprises one or more features configured to displace the cell. In some embodiments, the flow channel comprises one or more chemical functionalizations. In some embodiments, the one or more chemical functionalizations are configured to interact with one or more analytes. In some embodiments, the one or more flow channels is configured to receive an acoustic wave, wherein the acoustic wave is configured to rotate the cell on an axis. In some embodiments, the flow channel comprises one or more features configured to rotate the cell on an axis. In some embodiments, the one or more flow channels are configured to contact a light scattering control system. In some embodiments, the one or more flow channels have a width configured to pass one cell at a time. In some embodiments, the width of the one or more flow channels is 100 nanometers. In some embodiments, the chip comprises at least 20 flow channels. In some embodiments, the chip comprises at least 100 flow channels. In some embodiments, the chip is integrated with a circuit. In some embodiments, the chip is integrated with a microfluidic circuit. In some embodiments, the chip is integrated with an electrical circuit. In some embodiments, the chip is integrated with a photonic circuit. In some embodiments, the chip is configured to connect to an analyte processing device disclosed herein.

Methods of Analysis

The analyte processing device of the disclosure herein can be used to conduct biological and chemical analysis useful for many types of scientific experiments. In some embodiments, the analyte processing device is used to determine important biochemical and physiological details of a sample or analyte. In some embodiments, provided herein is a method for analyzing an analyte, comprising: providing a device comprising (i) a flow channel and (ii) one or more photodetectors in optical communication with the flow channel, wherein the one or more photodetectors comprises a light scattering control element; using the one or more photodetectors to acquire an optical signal from the analyte flowing through the flow channel; and processing the optical signal to identify a presence of the cell in the fluid flowing through the flow channel.

In some embodiments, provided herein is a method for analyzing an analyte, comprising: providing a device comprising (i) a flow channel comprising the analyte, and (ii) one or more photodetectors in optical communication with the flow channel; using the one or more photodetectors to acquire a first optical signal from the flow channel at a first position within the flow channel at a first time point; using the one or more photodetectors to acquire a second optical signal from the flow channel at a second position within the flow channel at a second time point subsequent to the first time point, wherein the second position is downstream of the first position; and processing the first optical signal and the second optical signal to identify the analyte flowing through the flow channel. In some embodiments, the method further comprises using the one or more photodetectors to acquire a third optical signal at a third position within the flow channel. In some embodiments, the third position is downstream from the second position. In some embodiments, the first position, the second position, and the third position are equidistant from one another. In some embodiments, the difference between the second time point and the first time point is substantially equal to a difference between the third time point and the second time point.

In some embodiments, the method of analysis disclosed herein may vary with detection technology. Detection technology may be suited to the analytic procedure of the analyte processing device. In some embodiments, the detection technology comprises uncorrelated time lapse microscopy. In some embodiments, the detection technology comprises time of flight imaging. In some embodiments, the detection time of flight camera. In some embodiments, the detection technology comprises time of flight methods. In some embodiments, the detection technology comprises time correlated single photon counting (TCSCP). In some embodiments, the detection technology comprises uncorrelated time lapse microscopy (UTLM). In some embodiments, the detection technology comprises uncorrelated time lapse imaging (UTLI). In some embodiments, the method of analysis may comprise one or more detection technologies. In some embodiments, the method of analysis may comprise one or more detection algorithms. In some embodiments, the method of analysis comprises signal processing. In some embodiments, the method of analysis comprises data processing. In some embodiments, the method of analysis comprises a classification algorithm.

In some aspects, the methods of analyzing an analyte comprise providing a device comprising a flow channel and one or more photodetectors in optical communication with said flow channel, wherein said one or more photodetectors comprises one or more light scattering control elements, using said one or more photodetectors to acquire an optical signal from said analyte flowing through said flow channel, computer processing said optical signal to identify a presence of said cell in said fluid flowing through said flow channel. In some embodiments, the method of analysis comprises acquiring a light scattering spectra. In some embodiments, the method of analysis comprises acquiring an angular light scattering pattern. In some embodiments, the method of analysis comprises repeatedly detecting one or more beams of light.

In some aspects, the disclosure herein includes methods of analyzing an analyte comprising imaging an analyte. In some embodiments, the method of analysis comprises more than one optical signal. In some embodiments, the method of analysis comprises more than two, more than three, more than four, more than five, or more than ten optical signals. In some embodiments, the method of analysis comprises acquiring more than 10, more than 100, more than 1,000, or more than 10,000 optical signals. In some embodiments, the method of analysis comprises acquiring an optical signal at one time point. In some embodiments, the method of analysis comprises more than one, more than two, more than three, more than four, or more than five time points. In some embodiments, the method of analysis comprises acquiring optical signals at more than 10, more than 100, more than 1,000, or more than 10,000 time points. In some embodiments, the method of analysis comprises circulating an analyte within the one or more flow channels N times. In some embodiments, the method of analysis comprises imaging an analyte at least M times across a section of the one or more flow channels. In some embodiments, the method of analyzing comprises generating an N×M time of flight data for an analyte, wherein M is a number greater than one. In some embodiments, the method of analyzing comprises generating an N×M time of flight data for an analyte, wherein M is a number greater than one.

In some embodiments, the method of analysis comprises acquiring optical signals at equal time intervals. In some embodiments, the method of analysis comprises acquiring optical signals at unique time intervals. In some embodiments, the method of analysis comprises acquiring optical signals at equal spatial intervals. In some embodiments, the method of analysis comprises acquiring optical signals at unique time intervals. In some embodiments, the method of analysis comprises acquiring optical signals at a downstream position with respect to an initial optical signal. In some embodiments, the method of analysis comprises acquiring optical signals at equidistant spatial intervals. In some embodiments, the method of analysis comprises acquiring optical signals at unique spatial intervals.

In some embodiments, the method of analysis comprises acquiring one or more optical signals using a single photodetector. In some embodiments, the method of analysis comprises acquiring at least two, at least three, at least five, at least 10, at least 100, at least 1,000 or at least 1,000 optical signals using a single photodetector. In some embodiments, the method of analysis comprises acquiring one or more optical signals using more than one photodetector. In some embodiments, the method of analysis comprises acquiring at least two, at least three, at least five, at least 10, at least 100, at least 1,000 or at least 1,000 optical signals using more than one photodetector.

In some embodiments, the method of analysis comprises using a second photodetector or sensor that is configured to detect two or more optical signals (e.g., images) for each of a plurality of one or more analytes. In some embodiments, the two or more optical signals (e.g., images) detected by the second photodetector comprise the second signal from the second point of detection. In some embodiments, the two or more images for each of the plurality of target droplets may comprise a signal generated by a modulated or pulsed light source configured to provide repetitive short illumination of light energy. In some embodiments, the modulated or pulsed light source may optionally comprise one or more lasers or laser-like sources configured to provide stroboscopic illumination. In some embodiments, the first photodetector or sensor may comprise a fast-response optical detector. The fast-response optical detector may comprise a photomultiplier tube (PMT), a photodiode, an avalanche photodiode detector (APD), or a hybrid detector (HyD). In some embodiments, a photodetector may comprise a camera or camera-like detector with a square, rectangular, or linear array of pixels. In some embodiments, the photodetector may be spatially arranged in a specific manner. In some embodiments, the one or more excitation sources comprises at least one continuous wave laser. In some embodiments, the one or more excitation sources comprises at least one pulsed laser. In some embodiments, the one or more excitation sources comprises at least one tunable laser. In some embodiments, the one or more excitation sources comprises a laser tuned to near IR to visible wavelengths. In some embodiments, the one or more excitation sources comprises a single laser. In some embodiments, the one or more excitation sources comprises multiple lasers. In some embodiments, the one or more excitation sources comprises bonded lasers. In some embodiments, the one or more excitation sources comprises external lasers. In some embodiments, the one or more photodetectors comprise a single pixel photodetector. In some embodiments, the flow channel is on a substrate. In some embodiments, the photodetectors are on the substrate. In some embodiments, the flow channel and the one or more photodetectors are on layers on the substrate.

In some embodiments, the method of analysis comprises providing an analyte processing device that comprises a substrate, element, or membrane to manipulate the scattering of light. In some embodiments, the method of analysis comprises an analyte processing device that comprises one or more substrates, elements, or membranes to manipulate the propagation of light.

In some embodiments, the method of analysis comprises providing an analyte processing device that measures an analyte's size, texture, surface area, or other physical property. Using methods of cellular analysis, the analyte processing device may be used to determine organelle size, cell membrane size, mitochondrial count, organelle count, or other physical parameters of biological systems. In some embodiments, the analyte processing device comprises one or more of the following: $SiO_2$, TiN, Ti, $Si_3N_4$, silicon oxynitride (SiOxNy), TaO, HfO, Si, glass, or other similar material or oxide. In some embodiments, an analyte processing device comprises a series of layers. In some embodiments, the analyte processing device comprises one or more light scattering control elements. In some embodiments, the method of analysis comprises providing an analyte processing device that comprises one or more light scattering control elements forming one or more layers. In some embodiments, the analyte processing device comprises an acoustophoretic layer. In some embodiments, the analyte processing device comprises a flow channel layer. In some embodiments, the analyte processing device comprises a microfluidic channel layer. In some embodiments, the analyte processing device comprises a photonics circuit layer comprising one or more excitation sources or one or more optical circuits. In some embodiments, the analyte processing device comprises an analyte processing area. In some embodiments, the method of analysis comprises providing an analyte processing device that comprises one or more analyte processing areas.

In some embodiments, the method of analysis comprises providing an analyte processing device comprises a chip. In some embodiments, the analyte processing device comprises a cartridge. In some embodiments, the analyte processing device comprises a replaceable cartridge. In some embodiments, the method of analysis comprises an analyte processing device comprises a replaceable or consumable element. In some embodiments, the method of analysis comprises a chip that is integrated with one or more photodetectors, one or more excitation sources, one or more flow channels, one or more light scattering control elements, or any combination thereof. In some embodiments, the method of analysis comprises an analyte processing device that comprises a semiconductor chip. In some embodiments, the method of analysis comprises an analyte processing device that comprises a photonics chip. In some embodiments, the method of analysis comprises a chip is integrated with one or more light modifying elements. In some embodiments, the method of analysis comprises a chip that is integrated with one or more light scattering control systems. In some embodiments, the method of analysis comprises providing an analyte processing device that comprises one or more stacked layers. In some embodiments, the method of analysis comprises an analyte processing device comprising one or more layers of material that are integrated with a chip. In some embodiments, the method of analysis comprises providing an analyte processing device that comprises one or more stacked layers integrated with a chip. In some embodiments, the method of analysis comprises a chip that comprises several layers including but not limited to: an acoustophoresis layer, a microfluidic chamber layer, a microfluidic channel layer, a flow channel layer, a light modifying membrane layer, a photodetector layer, an excitation source layer, an optical circuit layer, a photonics circuit layer, or a light modifying substrate layer. In some embodiments, the method of analysis comprises an analyte processing device that comprises an optical circuit that comprises one or more light entry sections, one or more optical dividers, a light delivery section, or any combination thereof. In some embodiments, the method of analysis comprises an analyte processing device that comprises an energy source. In some embodiments, the method of analysis comprises an analyte processing device that comprises a battery. In some embodiments, the method of analysis comprises an analyte processing device that comprises an energy source is integrated with the analyte processing device.

In some embodiments, the method of analysis comprises a chip that comprises an application specific integrated circuit. In some embodiments, the method of analysis comprises a chip that comprises an integrated circuit. In some embodiments, the method of analysis comprises a chip that is integrated with one or more other aspects of the analyte processing device, including but not limited to: one or more flow channels, one or more light scattering control elements, a power source, one or more photodetectors, one or more excitation sources, or one or more phoresis elements, one or more circuits, or one or more chips. In some embodiments, the method of analysis comprises a chip that comprises an optical circuit. In some embodiments, the method of analysis comprises an analyte processing device wherein a readout circuitry may be operatively coupled to the analyte processing device, wherein the readout circuitry is configured to transmit the data from the analyte processing device to memory.

In some embodiments, the method of analysis comprises an analyte processing device that comprises more than one flow channel. In some embodiments, the method of analysis comprises an analyte processing device that comprises more than two, more than four, more than eight, or more than 16 flow channels. In some embodiments, the method of analysis comprises an analyte processing device that comprises more than two, more than 64, more than 128, or more than 256 flow channels. In some embodiments, the method of analysis comprises providing a flow channel that comprises at least one outlet, at least two outlets, at least three outlets, or at least four outlets. In some embodiments, the method of analysis comprises providing a flow channel that comprises at least 16 outlets, at least 64 outlets, at least 128 outlets, at least 256 outlets, at least 1028 outlets. In some embodiments, the method of analysis comprises providing a flow channel that comprises at least one inlet, at least two inlets, at least three inlets, or at least four inlets. In some embodiments, the method of analysis comprises providing a flow channel that comprises at least 16 inlets, at least 64 inlets, at least 128 inlets, at least 256 inlets, at least 1028 inlets. In some embodiments, the method of analysis comprises providing a flow channel that is rectangular. In some embodiments, the method of analysis comprises providing a flow channel that is curved, indented, or similarly modified. In some embodiments, the method of analysis comprises providing a flow channel that is integrated with the analyte processing device. In some embodiments, the method of analysis comprises providing a flow channel that is configured to generate electrophoresis such as acoustophoresis, electrophoresis, or magnetophoresis. In some embodiments, the method of analysis comprises providing a flow channel that is configured to displace analytes within the flow channel. In some embodiments, the method of analysis comprises providing a flow channel that comprises one or more pumps. In some embodiments, the method of analysis comprises providing a flow channel comprises one or more double-sided indents. In some embodiments, the method of analysis comprises providing a flow channel that comprises one or more single sided indents. In some embodiments, the method of analysis comprises providing a flow channel that comprises one or more single sided pinches. In some embodiments, the method of analysis comprises providing a flow channel that comprises one or more double sided pinches. In some embodiments, the method of analysis comprises providing a flow channel that comprises one or more curves. In some embodiments, the method of analysis comprises providing a flow channel that comprises one or more posts. In some embodiments, the method of analysis comprises providing a flow channel that comprises one or more bisections. In some embodiments, the method of analysis comprises providing a flow channel that comprises one or more intersections. In some embodiments, the method of analysis comprises providing a flow channel that comprises one or more convergence sections.

In some embodiments, the method of analysis comprises providing a flow channel that comprises a gate. In some embodiments, the method of analysis comprises providing a flow channel that comprises one or more gates. In some embodiments, the method of analysis comprises providing a flow channel that comprises a sorting junction. In some embodiments, the method of analysis comprises providing a flow channel that comprises one or more sorting junction. In some embodiments, the method of analysis comprises providing a flow channel that comprises a series of sorting junctions. In some embodiments, the method of analysis comprises providing a flow channel that comprises one or more chambers. In some embodiments, the method of analysis comprises providing a flow channel that comprises more than five, more than 10, more than 50, or more than 100 chambers. In some embodiments, the method of analysis comprises providing a flow channel that comprises a fluid reservoir. In some embodiments, the method of analysis comprises providing a flow channel that comprises more than one fluid reservoir.

In some embodiments, the method of analysis comprises providing a flow channel that comprises a feedback loop. In some embodiments, the method of analysis comprises providing a flow channel that comprises an inline pump. In some embodiments, the method of analysis comprises providing a flow channel that comprises a pump. In some embodiments, the method of analysis comprises providing a flow channel that comprises a cell injector. In some embodiments, the method of analysis comprises providing a flow channel that comprises a cell cartridge. In some embodiments, the method of analysis comprises providing a flow channel that comprises a cell collector. In some embodiments, the method of analysis comprises providing a flow channel that comprises a buffer reservoir. In some embodiments, the method of analysis comprises providing a flow channel that may branch in an 1×N pattern, where N is an integer greater than one. In some embodiments, the method of analysis comprises providing a flow channel that may branch in a series of 1×N patterns, where N is an integer greater than one. In some embodiments, the method of analysis comprises providing a flow channel that comprises one or more pneumatically driven valves. In some embodiments, the method of analysis comprises providing a flow channel that comprises one or more fluid reservoirs. In some embodiments, the method of analysis comprises providing a flow channel that comprises one or more peristaltic pumps.

In some embodiments, the method of analysis comprises providing an analyte processing device that comprises a substrate, element, or membrane to manipulate the scattering of light. In some embodiments, the method of analysis comprises providing an analyte processing device that comprises a light scattering control system. In some embodiments, the method of analysis comprises providing a flow channel that comprises a light modifying system. In some embodiments, the method of analysis comprises providing a flow channel that comprises a light modifying substrate. In some embodiments, the method of analysis comprises providing a flow channel that comprises a light modifying element. In some embodiments, the light scattering control system comprises a light modifying element that may be a dichroic optical component, a mirror, a membrane, a concentrator, a lens, a blocker, optical grating, a reflector, vertical couplers, lateral couplers, a filter, or a light entry section. In some embodiments, the method of analysis comprises providing an analyte processing device that comprises a light entry section. In some embodiments, the light scattering control system comprises a light entry section that is a pinhole. In some embodiments, the light scattering control system comprises a light entry section that comprises vertical couplers. In some embodiments, the light scattering control system comprises a light entry section that comprises lateral couplers. In some embodiments, the method of analysis comprises a light entry section that comprises optical grating. In some embodiments, the light scattering control system comprises a light entry section that comprises one or more dichroic optical components. In some embodiments, the method of analysis comprises a filter that is a dielectric material. In some embodiments, the light scattering control system comprises a filter that is a metallic material. In some embodiments, the light scattering control system comprises a filter is a semiconductor material. In some embodiments, the filter is a combination of a dielectric, metallic, or semiconductor material, or combination thereof. In some embodiments, the filter comprises more than layer of filters. In some embodiments, the light scattering control system comprises a blocker that comprises a layer of absorptive material configured to absorb specific light wavelengths. In some embodiments, the blocker comprises a layer of material configured to transmit specific wavelengths of light. In some embodiments, the blocker comprises a layer of material configured to transmit specific ranges of wavelengths of light. In some embodiments, the blocker comprises a layer of material configured to absorb specific ranges of wavelengths of light. In some embodiments, the blocker increases the signal to noise ratio by a factor of two. In some embodiments, the blocker increases the signal to noise ratio by a factor of at least two, at least 10, at least 100, at least 1,000, or at least 10,000. In some embodiments, the light scattering control system comprises a concentrator that that comprises a lens. In some embodiments, the light scattering control system comprises a lens that is a microlens, a flat lens, a diffractive lens, an absorptive lens, a non-absorptive lens, or any combination thereof. In some embodiments, the light scattering control system comprises a concentrator that that is a dielectric block. In some embodiments, the dielectric block is at least 100 nanometers thick. In some embodiments, the dielectric block that is at least 1 micrometer thick. In some embodiments, the light scattering control system comprises a mirror that is configured to improve the coupling efficiency of vertical couplers. In some embodiments, the light scattering control system comprises a reflector that is configured to improve the coupling efficiency of vertical couplers. In some embodiments, the light scattering control system comprises a mirror that is configured to improve the coupling efficiency of lateral couplers. In some embodiments, the light scattering control system comprises a reflector that is configured to improve the coupling efficiency of lateral couplers.

In some embodiments, the method of analysis comprises providing a device that comprises one excitation source. In some embodiments, the device comprises more than one, more than two, more than three, more than four, or more than five excitation sources. In some embodiments, the device comprises at least 10, at least 20, at least 30, or at least 40 excitation sources. In some embodiments, the device comprises one or more excitation sources integrated with the device. In some embodiments, the device comprises one or more excitation sources integrated with a chip. In some embodiments, the device comprises one or more excitation sources that comprises a photon array. In some embodiments, the device comprises one or more excitation sources that comprises one or more photon arrays. In some embodiments, the device comprises one or more excitation sources that comprises a waveguide. In some embodiments, the device comprises one or more excitation sources that are configured to yield specific wavelengths of lights. In some embodiments, the device comprises one or more excitation sources that comprises an interposer. In some embodiments, the device comprises one or more excitation sources that comprises a transducer. In some embodiments, the device comprises one or more excitation sources that comprises a laser. In some embodiments, the device comprises one or more excitation sources that comprises an integrated circuit. In some embodiments, the device comprises one or more excitation sources that comprise an interposer. In some embodiments, the device comprises an excitation source that comprises a transducer. In some embodiments, the device comprises an excitation source comprises an interposer. In some embodiments, the device comprises an excitation source that comprises more than one interposer. In some embodiments, the device comprises an excitation source comprises a transducer. In some embodiments, the device comprises an excitation source that comprises one or more transducers. In some embodiments, the device comprises an excitation source that comprises a laser. In some embodiments, the device comprises an excitation source that comprises more than one laser, more than 10 lasers, more than 100 lasers, or more than 1,000 lasers. In some embodiments, the device comprises a laser that is a bonded laser. In some embodiments, the device comprises a laser that is an external laser. In some embodiments, the device comprises a laser is a continuous laser. In some embodiments, the device comprises a laser that is a pulsed laser. In some embodiments, the device comprises one or more lasers that are tunable lasers. In some embodiments, the device comprises one or more excitation sources that is configured to generate a light wavelength between 300 nm and 1,200 nm. In some embodiments, the device comprises one or more excitation sources that is configured to generate a light with a height between at least 80 nm and at most 200 nm. In some embodiments, the device comprises one or more excitation sources that is configured to generate light intensity of at least 1 $\mu W/\mu m^2$. In some embodiments, the device comprises one or more excitation sources that generates a light intensity of less than 10 1 $\mu W/\mu m^2$. In some embodiments, the device comprises one or more lasers are integrated with a chip. In some embodiments, the one or more lasers comprises an excitation source that is integrated with a chip. In some embodiments, the device comprises a chip that is integrated with one flow channel. In some embodiments, the device comprises a chip that is integrated with more than one flow channel. In some embodiments, the device comprises a chip that is integrated with a phoresis mechanism. In some embodiments, the device comprises a chip that is integrated with one or more excitation sources.

In some embodiments, the device comprises a chip that is integrated with one or more microfluidic channels. In some embodiments, the device comprises a chip that is integrated with one or more micro-optics components. In some embodiments, the device comprises a chip that is integrated with one or more photonic circuits. In some embodiments, the device comprises a chip that is integrated with one or more CMOS photodetectors. In some embodiments, the device comprises a chip that is integrated with one or more photodetectors. In some embodiments, the device comprises a chip that is integrated with one or more light scattering control elements. In some embodiments, the device comprises a semiconductor chip that comprises a power source, one or more controllers, one or more readouts, and one or more photodetector pixels. In some embodiments, the device comprises an excitation source that comprises a waveguide. In some embodiments, the device comprises an excitation source that comprises an optical waveguide. In some embodiments, the device comprises an optical waveguide may branch in an 1×N pattern, where N is an integer greater than one. In some embodiments, the device comprises an optical waveguide comprises more than one branching point. In some embodiments, the device comprises an optical waveguide may comprise one or more 1×2 branching points. In some embodiments, the device comprises an excitation source that is configured to excite light at specific wavelengths. In some embodiments, the device comprises an excitation source that is configured to excite light at specific ranges of light wavelengths. In some embodiments, the device comprises an excitation source that is configured to excite light in the ultraviolet range. In some embodiments, the device comprises an excitation source that is configured to excite light in the microwave range. In some embodiments, the device comprises an excitation source that is configured to excite light in the IR to visible light range. In some embodiments, the device comprises an excitation source that comprises a pinhole for light entry. In some embodiments, the device comprises an excitation source that comprises an optical circuit. In some embodiments, the device comprises an optical circuit comprises one or more light entry sections. In some embodiments, the device comprises an excitation source that is programmed to generate an evanescent light field. In some embodiments, the device comprises an excitation source that is programmed to generate a superposition of light fields. In some embodiments, the device comprises an excitation source that's programmed to synchronize with other elements of the analyte processing device sources. In some embodiments, the device comprises one or more excitation sources are programmed to synchronize with other excitation sources. In some embodiments, the device comprises an analyte processing area that is configured to enable photodetectors to yield high resolution images of an analyte. In some embodiments, the device comprises an analyte processing device that comprises one photodetector. In some embodiments, the device comprises an analyte processing device that comprises more than one photodetector, more than two photodetectors, more than four photodetectors, more than eight photodetectors, or more than 16 photodetectors. In some cases, the analyte processing device comprises more than 32 photodetector, more than 64 photodetectors, more than 128 photodetectors, more than 256 photodetectors, or more than 512 photodetectors. In some embodiments, the device comprises a photodetector that comprises a semiconductor imager. In some embodiments, the device comprises a photodetector that comprises one or more semiconductor imagers. In some embodiments, the device comprises a photodetector that comprises a pixel. In some embodiments, the device comprises a photodetector that comprises more than one pixel. In some embodiments, the device comprises a photodetector that comprises more than 10, more than 100, more than 1,000 or more than 10,000 pixels. In some embodiments, the device comprises a photodetector that's positioned 10 microns apart from each other. In some embodiments, the device comprises a photodetector that's positioned 15 microns apart from each other. In some embodiments, the device comprises a photodetector that's positioned 20 microns apart from each other. In some embodiments, the device comprises a photodetector that's positioned at least 5 microns apart from each other. In some embodiments, the device comprises a photodetector that's positioned at least 10 microns apart from each other. In some embodiments, the device comprises a photodetector that's positioned at least 20 microns apart from each other. In some embodiments, the device comprises a photodetector that comprises one or more pixels. In some embodiments, the device comprises a photodetector that pixel size is 10 microns by 10 microns. In some embodiments, the device comprises a photodetector that pixel size is 20 microns by 10 microns. In some embodiments, the device comprises a photodetector that pixel size is 20 microns by 20 microns. In some embodiments, the device comprises a, a photodetector may comprise a camera or camera-like detector with a square, rectangular, or linear array of pixels. In some embodiments, the device comprises a photodetector that may be spatially arranged in a specific manner. In some embodiments, the device comprises providing an analyte processing device that comprises one photodetector station. In some embodiments, the device comprises providing an analyte processing device that comprises at least 2, at least 4, at least 8, at least 16, or at least 64 photodetector stations. In some embodiments, the device comprises providing an analyte processing device that comprises at least 128, at least 512, or at least 1028 photodetector stations. In some cases, one or more photodetectors are located on the bottom of the flow channel. In some cases, one or more photodetectors are located on the side of the flow channel. In some cases, the device comprises one or more photodetectors that are located on the top of the flow channel. In some embodiments, the device comprises one or more photodetectors covers a section of the flow channel surface. In some embodiments, the device comprises a photodetector that comprises a complementary metal oxide sensor (CMOS) imager. In some embodiments, the device comprises a photodetector that comprises one or more complementary metal oxide sensor (CMOS) imagers. In some embodiments, the device comprises a photodetector that comprises a CMOS imager configured to flush electrons generated with scattered light upon excitation. In some embodiments, the device comprises a photodetector that comprises a spectral CMOS imager. In some embodiments, the device comprises a photodetector that comprises a CMOS imager configured for photon wavelength. In some embodiments, the device comprises a photodetector that comprises a CMOS imager configured for photon intensity. In some embodiments, the device comprises a photodetector that comprises a pinned photodiode CMOS imager. In some embodiments, the device comprises a photodetector that comprises a single-photon avalanche diode CMOS imager. In some embodiments, the device comprises one or more photodetectors that form an optical path with the analyte processing area. In some embodiments, the device comprises one or more photodetectors forms an optical path with one or more analyte processing areas. In some embodiments, the device comprises one or more photodetectors forms one or more optical paths with the analyte processing area. In some embodiments, the device comprises an optical path that comprises light modifying substrates, layers, or elements. In some embodiments, the device comprises an optical path that comprises a light entry section, an optical circuit, optical grating, a reflector, vertical couplers, lateral couplers, a filter, a blocker, a concentrator, a mirror, or an optical membrane. In some embodiments, the device comprises an optical path comprises one or more light modifying substrates, layers, or elements. In some embodiments, the methods comprise an analyte processing area that comprises multiple individual sections or elements to optimize imaging under specific circumstances. In some embodiments, the device comprises an analyte processing device that comprises one or more analyte processing areas. In some embodiments, the device comprises an analyte processing area that forms an optical path with the one or more excitation sources. In some embodiments, the device comprises an analyte processing area that forms an optical path with the one or more photodetectors. In some embodiments, the device comprises an analyte processing area that may be between a sorting junction and a gate. In some embodiments, the device comprises an analyte processing area that is be between more than one sorting junction or more than one gate. In some embodiments, the device comprises an analyte processing area that comprises a light scattering control system. In some embodiments, the device comprises an analyte processing area that comprises a light scattering control element. In some embodiments, the device comprises an analyte processing area that comprises one or more light scattering control elements. In some embodiments, the device comprises an analyte processing area that comprises an optical membrane. In some embodiments, the device comprises an analyte processing area that comprises a light modifying substrate or light modifying element. In some embodiments, the device comprises an analyte processing area that comprises an optical membrane. In some embodiments, the device comprises an analyte processing area that comprises a layer of light modifying substrates. In some embodiments, the method of analysis comprises providing a flow channel that comprises an analyte processing area. In some embodiments, the method of analysis comprises providing a flow channel that comprises one or more analyte processing areas. In some embodiments, the device comprises an analyte processing area that is at the bottom surface. In some embodiments, the device comprises an analyte processing area that is at the top surface. In some embodiments, the device comprises an analyte processing area that is on the side of the surface.

In some embodiments, the method of analysis comprises an analyzing an analyte that is singular. In some embodiments, the analyte comprises a population. In some embodiments, the analyte is an inorganic chemical. In some embodiments, the analyte is an organic chemical. In some embodiments, the analyte is a peptide, small molecule, drug molecule, drug-conjugate molecule, dye molecule, dye-conjugate molecule, fluorescent molecule, or any other organic chemicals of interest.

In some embodiments, the method of analysis comprises analyzing an analyte that comprises a biological sample. In some embodiments, the method of analysis comprises an analyte that comprises at least one cell. In some embodiments, the method of analysis comprises an analyte that is a population of cells. In some embodiments, the analyte comprises at least one cell that may be a mammalian cell, a eukaryotic cell, a yeast cell, a bacterial cell, a primary cell, an immortalized cell, a cancer cell, a hybrid cell, or a derivative or an engineered form thereof. In some embodiments, the analyte is blood. In some embodiments, the analyte is plasma. In some embodiments, the analyte is cerebrospinal fluid. In some embodiments, the analyte is lymph tissue. In some embodiments, the analyte is a specific type of cell from a subject. In some embodiments, the analyte is a specific type of cell that is from the brain, liver, heart, intestine, colon, muscle, kidney, pancreas, or other organ. In some embodiments, the analyte comprises skin cells, heart cells, immune system cells such as B-cells, lymphocytes, T-cells, kidney cells, liver cells, muscle cells, nervous system cells such as astral cells, glial cells, neuronal cells, bacterial cells, or peripheral blood mononuclear cells.

In some embodiments, the method of analysis comprises analyzing an analyte that is in the liquid phase. In some embodiments, the method of analysis comprises analyzing an analyte that is in the gas phase. In some embodiments, the an analyte is an aqueous solution. In some embodiments, the analyte is solvated in an organic solution (e.g., acetone, methanol, acetonitrile, tetrahydrofuran, or other organic solvent). In some embodiments, the analyte is at least partially aerosolized. In some embodiments, the analyte is an aerosol. In some embodiments, the analyte motion is a laminar motion. In some embodiments, the analyte motion is turbulent. In some embodiments, the analyte comprises one or more additional solutes. In some embodiments, the analyte comprises a solvent that is phosphate buffered saline (PBS).

In some embodiments, the method of analysis comprises analyzing an analyte that is processed prior to analysis. In some embodiments, the method of analysis comprises an analyte that is reacted with a fluorophore, dye, labeling agent, or other similar chemical reagent. In some embodiments, the method of analysis comprises an analyte that is centrifuged prior to analysis. In some embodiments, the method of analysis comprises an analyte is heated prior to analysis. In some embodiments, the method of analysis comprises an analyte that is cooled prior to analysis. In some embodiments, the method of analysis comprises an analyte that is frozen, or flash frozen, prior to analysis. In some embodiments, the method of analysis comprises an analyte that is a suspension. In some embodiments, the method of analysis comprises an analyte that is homogenous. In some embodiments, the method of analysis comprises an analyte is heterogenous. In some embodiments, the method of analysis comprises an analyte that may be labelled with a fluorophore, a fluorescent molecule, a dye, or other similar moiety. In some embodiments, the method of analysis comprises an analyte that is at least one cell that may be labelled with a fluorophore or expresses a fluorescent molecule. In some embodiments, the method of analysis comprises at least once cell that may express a molecule including, but not limited, to a fluorescent molecule, a phosphorescent molecule, a chemiluminescent molecule, or a bioluminescent molecule. In some embodiments, the method of analysis comprises fluorophores that can be used as labels for specific target analytes, in applications where the targets can be chemically modified to incorporate a TGF fluorophore. Examples include, but are not limited to, Northern blots, Southern blots, DNA microarrays, quantitative Polymerase Chain Reaction (PCR), digital PCR, and diagnostic assays.

In some embodiments, the method of analysis comprises optical communication that comprises an optical path between an analyte of interest, one or more excitation sources, and one or more photodetectors. In some embodiments, the method of analysis comprises optical communication that comprises an optical path between one or more analytes of interest, one or more excitation sources, and one or more photodetectors.

In some embodiments, the method of analysis comprises an analyte processing device that comprises an optical path. In some embodiments, the method of analysis comprises an optical path is formed between one or more excitation sources and an analyte. In some embodiments, the method of analysis comprises an optical path that is formed between one or more photodetectors and the analyte processing area. In some embodiments, the method of analysis comprises an optical path that is formed between one or more photodetectors, one or more excitation sources, and an analyte. In some embodiments, the method of analysis comprises an optical path that is formed between one or more photodetectors and the analyte processing area. In some embodiments, the method of analysis comprises an optical path that comprises a light scattering control element. In some embodiments, the method of analysis comprises a light scattering control element that comprises a layer of material. In some embodiments, the method of analysis comprises a light scattering control element that comprises a material that comprises one or more of the following: $SiO_2$, TiN, Ti, $Si_3N_4$, silicon oxynitride (SiOxNy), TaO, HfO, Si, glass, or other similar material or oxide. In some embodiments, the method of analysis comprises an optical path that forms an angle of at least 10, at least 20, at least 30, at least 40, at least 50, at least 60, at least 70, at least 80, or at least 90 degrees with the one or more light scattering control elements.

In some embodiments, the method of analysis comprises providing a device comprising an optical path between the photodetector and the analyte processing area that comprises a light scattering control element. In some embodiments, the method of analysis comprises an optical path that comprises a lens, concentrator, dielectric, dichroic, reflector, or mirror. In some embodiments, the method of analysis comprises an optical path that comprises elements configured to redirect scattered light distal from a photodetector. In some embodiments, the method of analysis comprises an optical path that comprises elements configured to redirect scattered light distal from one or more photodetectors. In some embodiments, the method of analysis comprises an optical path that comprises more than one element configured to redirect scattered light distal from a photodetector. In some embodiments, the method of analysis comprises an optical path that comprises a dichroic optical component configured to redirect scattered light distal from one or more photodetectors. In some embodiments, the method of analysis comprises an optical path that comprises more than one membrane. In some embodiments, the method of analysis comprises an optical path comprises a light modifying membrane. In some embodiments, the method of analysis comprises an optical path that comprises an angle relative to an analyte. In some embodiments, the method of analysis comprises an optical path that comprises an angle relative to the light modifying element. In some embodiments, the method of analysis comprises an optical path that comprises an angle relative to the light modifying substrate. In some embodiments, the method of analysis comprises an optical path that comprises an angle relative to the light modifying layer.

In some embodiments, the method of analysis comprises providing a device that comprises a light scattering control system that is configured to optimize signal to noise ratio of an analyte. In some embodiments, the method of analysis comprises a light scattering control system that is configured to optimize light propagation. In some embodiments, the method of analysis comprises a light scattering control system that is configured to optimize evanescent light propagation. In some embodiments, the method of analysis comprises a light scattering control system that is configured to propagate evanescent light. In some embodiments, the method of analysis comprises a light scattering control system that is configured to shutter excess light excitation within the analyte processing device. In some embodiments, the method of analysis comprises a light scattering control system that is configured to reduce excess light propagation. In some embodiments, the method of analysis comprises a light scattering control system that is configured to optimize angular light propagation. In some embodiments, the method of analysis comprises a light scattering control system that comprises a light modifying element. In some embodiments, the method of analysis comprises a light scattering control system that comprises one or more light modifying elements.

In some embodiments, the method of analysis comprises a measurement sensitivity achieved through the light scatter control system that is at least a factor of two. In some embodiments, the method of analysis comprises a sensitivity increase is at least a factor of 10, at least a factor of 100, at least a factor of 1,000, at least a factor of 10,000, or at least a factor 100,000. In some embodiments, the method of analysis comprises a light scattering control system that increases the signal to noise ratio by at least a factor of two, a factor of five, a factor of 10, a factor of 100, a factor of 1,000, or a factor of 10,000. In some embodiments, the method of analysis comprises a signal to noise ratio that is improved by reducing excess electrons. In some embodiments, the method of analysis comprises a signal to noise ratio that is improved by signal correlation between more than two or more photodetectors. In some embodiments, the method of analysis comprises a signal to noise ratio that is improved by an evanescent light field. In some embodiments, the method of analysis comprises a signal to noise ratio that is improved by an imaging modality. In some embodiments, the method of analysis comprises reducing noise from light scattering within a waveguide. In some embodiments, the method of analysis comprises reducing noise from light scattering due to photonics structure. In some embodiments, the method of analysis comprises reducing noise from light scattering due to an integrated circuit. In some embodiments, the method of analysis comprises reducing noise from light scattering due to an application specific integrated circuit. In some embodiments, the method of analysis comprises a noise is reduced from light scattering due to light scattering from one or more analytes. In some embodiments, the method of analysis comprises reducing noise from light scattering due to flow channel structure. In some embodiments, the method of analysis comprises reducing noise from light scattering due to microfluidic channel walls. In some embodiments, the method of analysis comprises reducing noise from light scattering due to photodetector structure.

In some embodiments, the method of analysis comprises providing an analyte processing device that comprises a light scattering control element, which may form a broader light scattering control system. In some embodiments, the analyte processing device comprises one or more light scattering control systems. In some embodiments, the analyte processing device comprises one or more light scattering control elements. In some embodiments, the analyte processing device comprises an optical path that comprises a light scattering control element. In some embodiments, the analyte processing device comprises an optical path that comprises one or more light scattering control elements. In some embodiments, the analyte processing device comprises a light scattering control element that comprises a lens, a concentrator, mirror, reflector, optical grating, blocker, coupler, or absorptive material. In some embodiments, the method of analysis comprises a light scattering control element that comprises a micro-interferogram element (MIE). In some embodiments, the analyte processing device comprises one or more light scattering control elements comprise a light entry section. In some embodiments, the analyte processing device comprises a light entry section that is a pinhole. In some embodiments, the analyte processing device comprises a light entry section that comprises vertical couplers. In some embodiments, the analyte processing device comprises a light entry section that comprises lateral couplers. In some embodiments, the analyte processing device comprises a light entry section comprises optical grating. In some embodiments, the analyte processing device comprises a light entry section comprises one or more dichroic optical components. In some embodiments, the analyte processing device comprises a filter that is a dielectric material. In some embodiments, the analyte processing device comprises a filter that is a metallic material. In some embodiments, the analyte processing device comprises a filter that is a semiconductor material. In some embodiments, the analyte processing device comprises a filter that is a combination of a dielectric, metallic, or semiconductor material, or combination thereof. In some embodiments, the analyte processing device comprises a filter that comprises more than layer of filters. In some embodiments, the analyte processing device comprises a blocker that comprises a layer of absorptive material configured to absorb specific light wavelengths. In some embodiments, the analyte processing device comprises a blocker that comprises a layer of material configured to transmit specific wavelengths of light. In some embodiments, the analyte processing device comprises a blocker that comprises a layer of material configured to transmit specific ranges of wavelengths of light. In some embodiments, the analyte processing device comprises a blocker that comprises a layer of material configured to absorb specific ranges of wavelengths of light. In some embodiments, the analyte processing device comprises a, a blocker increases the signal to noise ratio by a factor of two. In some embodiments, the analyte processing device comprises a blocker that increases the signal to noise ratio by a factor of at least two, at least 10, at least 100, at least 1,000, or at least 10,000. In some embodiments, the analyte processing device comprises a concentrator that comprises a lens. In some embodiments, the analyte processing device comprises a lens that is a microlens, a flat lens, a diffractive lens, an absorptive lens, or a non-absorptive lens. In some embodiments, the analyte processing device comprises a concentrator that is a dielectric block. In some embodiments, the analyte processing device comprises a dielectric block that is at least 100 nanometers thick. In some embodiments, the analyte processing device comprises a dielectric block that is at least 1 micrometer thick. In some embodiments, the analyte processing device comprises a mirror that is configured to improve the coupling efficiency of vertical couplers. In some embodiments, the analyte processing device comprises a reflector that is configured to improve the coupling efficiency of vertical couplers. In some embodiments, the analyte processing device comprises a mirror that is configured to improve the coupling efficiency of lateral couplers.

In some embodiments, the analyte processing device comprises a reflector that is configured to improve the coupling efficiency of lateral couplers. In some embodiments, the analyte processing device comprises light scattering control elements that are integrated with the analyte processing device.

In some embodiments, provided herein is a method of imaging an analyte in motion, comprising: providing a flow channel adjacent to one or more photodetectors, wherein the flow channel comprises an analyte processing area configured for one or more photodetection events; providing conditions sufficient for the analyte to travel along a path in the flow channel; using the one or more photodetectors to probe the analyte in motion N times within the analyte processing area, wherein N is a number greater than one; repeating the first through third operation (i-iii) M times to generate an N×M time of flight (TOF) data for the analyte in motion, wherein M is a number greater than one; and using the N×M TOF data to classify the analyte in motion at an accuracy greater than 80%.

In some embodiments, using the N×M TOF data classifies the analyte in motion at an accuracy greater than 90%. In some embodiments, using the N×M TOF data classifies the analyte in motion at an accuracy greater than 95%. In some embodiments, using the N×M TOF data classifies the analyte in motion at an accuracy greater than 98%. In some embodiments, using the N×M TOF data classifies the analyte in motion at an accuracy greater than 99%. In some embodiments, the analyte in motion is probed at spatially separate locations along the analyte processing area. In some embodiments, the flow channel further comprises one or more pneumatically driven valves. In some embodiments, the flow channel further comprises one or more fluid reservoirs. In some embodiments, the flow channel further comprises one or more peristaltic pump valves. In some embodiments, the flow channel further comprises one or more peristaltic pump valves. In some embodiments, the classification confirms a biotherapeutic analytical characterization. In some embodiments, the classification comprises classifying a cellular phenotype. In some embodiments, the classification comprises using a machine learning algorithm. In some embodiments, the machine learning algorithm is a convolutional neural network. In some embodiments, the machine learning algorithm is a generational neural network. In some embodiments, the convolutional neural network is a 1D neural network trained using a training data set comprising at least 100 data sets. In some embodiments, the machine learning algorithm classifies cells as cancerous or non-cancerous. In some embodiments, the machine learning algorithm classifies at least 100,000 cells per second. In some embodiments, the machine learning algorithm classifies with a false negative rate of less than one in one billion. In some embodiments, the machine learning algorithm classifies with a false positive rate of less than one in one billion. In some embodiments, the machine learning algorithm classifies with a true positive rate of at least 99.9 percent.

In some embodiments, provided herein is a method of determining a dimension of an analyte or a cell, the method comprising subjecting the analyte or the cell to flow along a flow channel; and repeatedly detecting one or more beams of light, wherein the one or more beams of light are scattered by the analyte or the cell, and wherein the one or more beams of light comprise an angular light scattering pattern, wherein the angular light scattering pattern identifies the dimension of the analyte or the cell. In some embodiments, provided herein is a method of determining a dimension of an analyte or a cell, the method comprising subjecting the analyte or the cell to flow along a flow channel; and repeatedly detecting one or more beams of light, wherein the one or more beams of light are scattered by the particle or the cell, and wherein the one or more beams of light comprise a light scattering spectral pattern, wherein the light scattering spectral pattern identifies the dimension of the analyte or the cell. In some embodiments, provided herein is a method for processing or analyzing a cell, comprising (a) subjecting the cell to flow along a flow channel and (b) detecting a signal from the cell to identify the cellular size at an accuracy of at least $10^{-9}$ m in a time period of at most 10 minutes. In some embodiments, provided herein is a method for processing or analyzing a cell, comprising (a) subjecting the cell to flow along a flow channel and (b) detecting a signal from the cell to identify the cellular organelle size at an accuracy of at least $10^{-9}$ m in a time period of at most 10 minutes. In some embodiments, provided herein is a method for processing or analyzing a cell, comprising (a) subjecting the cell to flow along a flow channel and (b) detecting a signal from the cell to identify a number of cellular mitochondria at an accuracy of at least 95 percent in a time period of at most 10 minutes. In some embodiments, provided herein is a method for processing or analyzing a cell, comprising (a) subjecting the cell to flow along a flow channel and (b) detecting a signal from the cell to identify a population of at least 1,000 cells in a time period of at most 10 minutes. In some embodiments, provided herein is a method of imaging a surface of a cell, the method comprising: providing a fluidic microchannel configured to receive the cell, wherein the fluidic microchannel comprises at least two detection zones along a length of the fluidic microchannel, wherein each of the at least two detection zones comprise an imager, and wherein the microfluidic channel comprises a feature adjacent to the at least two detection zones, wherein the feature is configured to induce a rotation along an axis of the cell upon contact with the cell; disposing the cell in the fluidic microchannel; providing a force adjacent to the fluidic microchannel, thereby traversing the cell across the length of the fluidic microchannel, wherein the feature does not terminate the traversing of the cell across the length of the fluidic microchannel; and capturing at least two, two dimensional images of the cell.

In some embodiments, the at least two, two dimensional images of the cell are at least super-resolution. In some embodiments, the method further comprises generating a three-dimensional structure of the cell derived from the at least two, two dimensional images of the cell. In some embodiments, provided herein is a method of imaging a surface of a cell in three dimensions, the method comprising: a. providing a flow channel configured to receive the cell, wherein the flow channel comprises at least a first detection zone and a second detection zone along a length of the flow channel, wherein the first detection zone, the second detection zone, or both, comprises an imager, and wherein the microfluidic channel comprises a feature adjacent to the first detection zone or the second detection zone, wherein the feature is configured to induce a rotation along an axis of the cell upon contact with the cell; (b) disposing the cell in the flow channel; (c) subjecting the cell to flow through the flow channel; (d) capturing one or more images of the cell as the cell passes the first detection zone and the second detection zone; and (e) generating a three-dimensional structure of the cell derived from the one or more images of the cell. In some embodiments, the feature does not terminate the flow of the cell through the fluidic microchannel. In some embodiments, the three-dimensional structure comprises an atlas of the cell. In some embodiments, the three-dimensional structure of the cell is at least super-resolution. In some embodiments, the three-dimensional structure comprises a classification of one or more membrane bound structures of the cell. In some embodiments, the three-dimensional structure comprises a morphometric classification of the cell. In some embodiments, the three-dimensional structure comprises a topography map of one or more membrane bound structures of the cell. In some embodiments, the three-dimensional structure comprises a map comprising a location of the one or more membrane bound structures on the surface of the cell. In some embodiments, the three-dimensional structure further comprises a motion dynamic characterization of the cell. In some embodiments, the detection comprises a spatial density map of one or more analytes. In some embodiments, the three-dimensional structure comprises one or more dynamic topographical data of the cell. In some embodiments, the cell is a single cell of a population of cells, and wherein the method further comprises repeating (b)-(e) for a second cell of the population of cells. In some embodiments, the steps (b)-(e) for the second cell of the population of cells occurs simultaneously to the first cell. In some embodiments, the repeating (b)-(e) for the second cell of the population of cells occurs subsequent to the first cell. In some embodiments, the first cell is a single cell of a population of cells, and wherein the method further comprises repeating (b)-(e) for a hundredth cell of the population of cells. In some embodiments, the repeating (b)-(e) for the hundredth cell of the population of cells occurs simultaneously to the first cell. In some embodiments, the repeating (b)-(e) for the hundredth cell of the population of cells occurs subsequent to the first cell. In some embodiments, provided herein is a method of analyzing a subject's blood comprising connecting a subject's blood flow to a device or analyte processing device disclosed herein. In some embodiments, the analysis comprises cancer cell detection. In some embodiments, the analysis comprises preparation of a subject's blood prior to analysis. In some embodiments, the analysis further comprises removal of cancer cells. In some embodiments, the analysis comprises intermittent sampling of the subject's blood. In some embodiments, provided herein is a method of spatially identifying one or more markers on an analyte surface, comprising: subjecting the analyte to flow through a flow channel; subjecting the analyte to one or more excitation sources, wherein the one or more excitation sources generates a light scattering pattern of the analyte surface; processing the light scattering pattern algorithmically to generate a topographic map of the analyte surface. In some embodiments, the topographic map comprises a location map of one or more markers. In some embodiments, the topographic map comprises an intensity map of one or more markers. In some embodiments, the topographic map comprises a density map of one or more markers.

In some embodiments, provided herein is a method for analyzing an analyte, comprising: providing a device comprising (i) a flow channel comprising the analyte, and (ii) one or more photodetectors in optical communication with the one or more flow channels; using the one or more photodetectors to acquire a first optical signal from the one or more flow channels at a first time point; using the one or more photodetectors to acquire a second optical signal from the one or more flow channels at a second time point subsequent to the first time point; and processing the first optical signal and the second optical signal to identify the analyte flowing through the one or more flow channels, collecting one or more two-dimensional images of the analyte, wherein the one or more two-dimensional images are combined and optimized algorithmically to produce a three-dimensional structure of the analyte, wherein the analyte in fluid motion is imaged as if it were static.

In some embodiments, the method further comprises using the one or more photodetectors to acquire a third optical signal at a third time point within the one or more flow channels. In some embodiments, the device further comprises one or more excitation sources in optical communication with the analyte processing area. In some embodiments, the method further comprises processing the three-dimensional structures to improve analyte analysis. In some embodiments, the method further comprises using the three-dimensional structure to determine analyte characteristics for a chemical or biological test. In some embodiments, the analyte characteristics reduce the number of false positives. In some embodiments, the analyte characteristics of multiple analytes is used to determine analyte characteristic distribution of a population of analytes. In some embodiments, the reduced number of false positives results in a change in a treatment protocol. In some embodiments, the method further comprises using the three-dimensional structure to separate false positive cancer tests from true cancer positives, wherein the results are used to create an individualized cancer treatment plan. In some embodiments, the analyte characteristic distribution of a population of analytes indicates the severity of multiple myeloma for a subject. In some embodiments, the characterization of the population of analytes can be used to extrapolate a causal factor of multiple myeloma present in the subject.

In some embodiments, provided herein is a method of spatially identifying one or more characteristics on an analyte surface, comprising: subjecting the analyte to flow through a flow channel; photodetecting by a single-photon avalanche diode (SPAD) array light emission from the analyte during the flow through the flow channel, wherein the analyte is in motion; and processing the light emission to generate a topographic map of the analyte surface.

In some embodiments, provided herein is a method of spatially identifying one or more characteristics on an analyte surface, comprising: subjecting the analyte to flow through a flow channel; subjecting the analyte to light from one or more excitation sources, wherein the light is polarized by a light scattering control system; photodetecting by a single-photon avalanche diode (SPAD) array light emission from the analyte; and processing the light emission to generate a topographic map of the analyte surface.

In some embodiments, provided herein is a method of spatially identifying one or more characteristics on an analyte surface, comprising: subjecting the analyte to flow through a flow channel; photodetecting by a single-photon avalanche diode (SPAD) array light emission from the analyte due to light from one or more excitation sources, wherein the light is polarized by a light scattering control system; and algorithmically processing the light emission to generate a topographic map of the analyte surface.

In some embodiments, provided herein is a method of spatially identifying one or more characteristics on an analyte surface, comprising: subjecting the analyte to flow through a flow channel, wherein the analyte; photodetecting by a single-photon avalanche diode (SPAD) array light emission from the analyte the analyte to one or more excitation sources, wherein the one or more excitation sources generates a polarized light scattering pattern of the analyte surface; processing the polarized light scattering pattern algorithmically to generate a topographic map of the analyte surface. In some embodiments, the light scattering control system is adjacent to one or more photodetectors. In some embodiments, the light scattering control system is adjacent to the flow channel. In some embodiments, the light scattering control system is adjacent to the light scattering control system. In some embodiments, the topographic map comprises an atlas of cellular expression In some embodiments, provided herein is a method for processing or analyzing a cell, comprising (a) subjecting the cell to flow along a flow channel and (b) detecting one or more two-dimensional images from the cell to generate a two-dimensional structure of the cell, wherein the two-dimensional structure comprises a topographic map.

In some embodiments, provided herein is a method for processing or analyzing a cell, comprising (a) subjecting the cell to flow along a flow channel and (b) detecting one or more two-dimensional images from the cell to generate a three-dimensional structure of the cell, wherein the three-dimensional structure comprises a topographic map.

In some embodiments, provided herein is a method for processing or analyzing a population of cells, comprising (a) subjecting the population of cells to flow along a flow channel and (b) detecting one or more two-dimensional images from the population of cells to generate one or more three-dimensional structures of the population of cells, wherein the population of cells is at least 1,000 cells, wherein the three-dimensional structures comprise a topographic map.

In some embodiments, provided herein is a method for processing or analyzing a cell, comprising (a) subjecting the cell to flow along a flow channel and (b) detecting one or more two-dimensional images from the cell to generate a three-dimensional structure of the cell in a time period of at most 10 minutes, wherein the three-dimensional structure comprises a topographic map.

In some embodiments, the cell is amongst a population of at least 1,000 cells.

In some embodiments, provided herein is a system for spatially identifying one or more markers on an analyte surface, the system comprising: subjecting the analyte to flow through a flow channel; subjecting the analyte to one or more excitation sources, wherein the one or more excitation sources generates a light scattering pattern of the analyte surface; and processing the light scattering pattern algorithmically to generate a topographic map of the analyte surface.

In some embodiments, provided herein is a method of spatially identifying one or more markers on an analyte surface, comprising: subjecting the analyte to flow through a flow channel; subjecting the analyte to one or more excitation sources, wherein the one or more excitation sources generates a light scattering pattern of the analyte surface; using the light scattering pattern of the analyte surface to generate a topographic map of the analyte surface.

In some embodiments, provided herein is a system for spatially identifying one or more markers on an analyte surface, comprising: subjecting the analyte to flow through a flow channel; subjecting the analyte to one or more excitation sources, wherein the one or more excitation sources generates a light scattering pattern of the analyte surface; and using the light scattering pattern of a surface of an analyte to generate a topographic map of the analyte surface.

In some embodiments, provided herein is a method for processing or analyzing a cell, comprising (a) subjecting the cell to flow along a flow channel and (b) detecting one or more two-dimensional images from the cell to generate a three-dimensional structure of the cell, wherein the three-dimensional structure comprises a topographic map.

In some embodiments, provided herein is a method for processing or analyzing a population of cells, comprising (a) subjecting the population of cells to flow along a flow channel and (b) detecting one or more two-dimensional images from the population of cells to generate one or more three-dimensional structures of the population of cells, wherein the population of cells is at least 1,000 cells, wherein the three-dimensional structure comprises a topographic map.

In some embodiments, provided herein is a method for processing or analyzing a cell, comprising (a) subjecting the cell to flow along a flow channel and (b) detecting one or more two-dimensional images from the cell to generate a three-dimensional structure of the cell in a time period of at most 10 minutes, wherein the three-dimensional structure comprises a topographic map. In some embodiments, the cell is amongst a population of at least 1,000 cells.

In some embodiments, provided herein is a system for spatially identifying one or more markers on an analyte surface, the system comprising: subjecting the analyte to flow through a flow channel; subjecting the analyte to one or more excitation sources, wherein the one or more excitation sources generates a light scattering pattern of the analyte surface; and processing the light scattering pattern algorithmically to generate a topographic map of the analyte surface.

In some embodiments, provided herein is a method of spatially identifying one or more markers on an analyte surface, comprising: subjecting the analyte to flow through a flow channel; subjecting the analyte to one or more excitation sources, wherein the one or more excitation sources generates a light scattering pattern of the analyte surface; using the light scattering pattern of a surface of an analyte to generate a topographic map of the analyte surface.

In some embodiments, provided herein is a system for spatially identifying one or more markers on an analyte surface, comprising: subjecting the analyte to flow through a flow channel; subjecting the analyte to one or more excitation sources, wherein the one or more excitation sources generates a light scattering pattern of the analyte surface; and using the light scattering pattern of a surface of an analyte to generate a topographic map of the analyte surface.

In some embodiments, the method of imaging further comprises generating a three-dimensional structural map of cellular expression. In some embodiments, the method of imaging further comprises generating a three-dimensional topographical map. In some embodiments, the method of imaging further comprises generating a three-dimensional map of cellular expression. In some embodiments, the method of imaging further comprises generating a three-dimensional functional map of an analyte or cell. In some embodiments, the method of imaging further comprises generating three-dimensional cell cartography.

Computer Processing

Computer processing may assist in delivering important data during use of the device described herein. Computer processing, which may also be referred to as "processing", helps yield electronically useful information during excitation and photodetection. In some embodiments, the method of analysis comprises time correlated microscopy. In some embodiments, the computer processing comprises time correlated single photon counting microscopy (TCSCP). In some embodiments, the computer processing comprises uncorrelated time lapse microscopy (UTLM). In some embodiments, the method of analysis comprises computer processing through additional algorithms. In some embodiments, the processing comprises Time-correlated Single Photon Counting (TCSPC). In some embodiments, the processing comprises Uncorrelated Time-lapse Microscopy (UTLM). In some embodiments, the method further comprises an analyte sorting operation.

Figure 16:
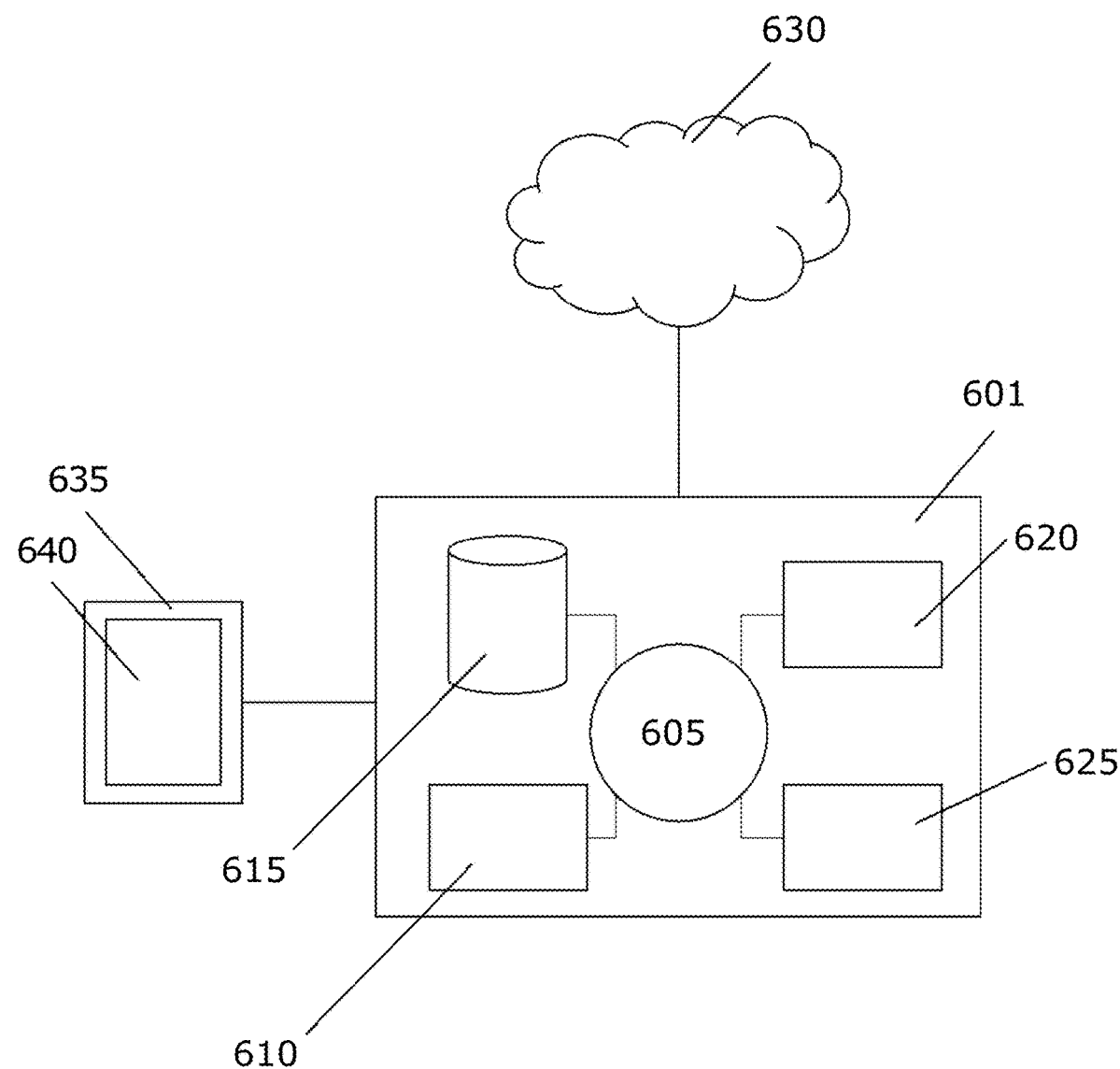
FIG. 16 illustrates a computer system utilizing the methods and systems described herein.

The present disclosure provides computer systems that are programmed to implement methods of the disclosure. FIG. 16 shows a computer system 601 that is programmed or otherwise configured to detect or analyze analytes. The computer system 601 can regulate various aspects of the analyte processing device of the present disclosure, such as, for example, excitation wavelengths of excitation sources. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user (e.g., an administrator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, experimental data of light scattering of a population of cells. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, load cell samples in series for analysis.

Optical Signals

In some embodiments, the optical signal may comprise an optical signal, an electrical signal, or an optical signal and an electrical signal. Optical signals can be manipulated and analyzed to yield valuable information about biological systems. In some embodiments, an optical signal comprises a light beam. In some embodiments, an optical signal comprises an angular light scattering pattern. In some embodiments, an optical signal comprises a light scattering spectra. In some embodiments, an optical signal comprises one or more light beams. In some embodiments, the method of analysis comprises acquiring the frequency distribution of an optical signal. In some embodiments, the method of analysis comprises acquiring the intensity distribution of an optical signal. In some embodiments, the method of analysis comprises acquiring the time distribution of an optical signal. In some embodiments, the method of analysis comprises acquiring the spectrum of an optical signal. In some embodiments, the method of analysis comprises acquiring one or more features of an optical signal, including but not limited to: frequency, intensity, time, spectrum, or other properties of light.

In some embodiments, the optical signal is at least partially generated via an excitation source. In some embodiments, the optical signal is at least partially generated via one or more excitation sources. In some embodiments, the optical signal is at least partially generated via an interaction between one more excitation sources and an analyte. In some embodiments, the optical signal is at least partially modified via a light scattering control element. In some embodiments, the optical signal is at least partially modified via one or more light scattering control elements. In some embodiments, the method of analysis comprises acquiring an optical signal that is generated by a fluorophore. In some embodiments, the method of analysis comprises acquiring an optical signal that is generated by a dye. In some embodiments, the method of analysis comprises acquiring an optical signal that is generated by an excitation source. In some embodiments, the method of analysis comprises acquiring an optical signal that is generated by one or more excitation sources. In some embodiments, the method of analysis comprises acquiring an optical signal that is manipulated or modified by a light scattering control element. In some embodiments, the method of analysis comprises acquiring an optical signal that is passed through a light scattering control element. In some embodiments, the method of analysis comprises acquiring an optical signal that is manipulated or modified by one or more light scattering control element. In some embodiments, the method of analysis comprises acquiring an optical signal that is scattered by a light scattering control element. In some embodiments, the method of analysis comprises acquiring an optical signal that is acquired by a photodetector comprising a light scattering control element. In some embodiments, the method of analysis comprises acquiring an optical signal that is acquired by one or more photodetectors comprising one or more light scattering control elements.

In some embodiments, optical signals are configured to synchronize the first point of detection and the second point of detection with a passage of time. In some embodiments, optical signals are configured to synchronize first point of detection and the second point of detection with the movement of an analyte. In some embodiments, optical signals are configured to synchronize first point of detection and the third point of detection with the movement of an analyte.

In some embodiments, the method of analysis comprises an analyte sorting operation. In some embodiments, the sorting operation comprises sorting analytes via a gate. In some embodiments, the sorting operation occurs from within a bulk analyte. In some embodiments, the sorting operation occurs between two flow channels. In some embodiments, the sorting operation occurs between a 1×N sorting junction, where N is an integer greater than 1. In some embodiments, the sorting operation sequesters the analyte in a separate container.

In some embodiments, the time period between the second optical signal and the first optical signal is greater the duration of the time period between the third optical signal and the second optical signal. In some embodiments, the time period between the second optical signal and the first optical signal is smaller than the time period between the third optical signal and the second optical signal.

In some embodiments, the spatial distance between the second optical signal and the first optical signal is greater the spatial distance between the third optical signal and the second optical signal. In some embodiments, the spatial distance between the second optical signal and the first optical signal is smaller than the spatial distance between the third optical signal and the second optical signal.

In some cases, the one or more optical signals are indicative of the presence or absence of the analyte. In some cases, the one or more optical signals are indicative of the size of an object such as a cellular organelle, mitochondria, golgi body, nuclear membrane, a cellular membrane, or combination thereof. In some embodiments, the one or more optical signals are indicative of the cell cycle state, immune state, or metabolic state of a cell. In some embodiments, the one or more optical signals are indicative of a number of cellular organelles or cellular structures, including but not limited to: mitochondria, lysosomes, nuclei, endoplasmic recticula, golgi apparati, vesicles, or any other cellular organelles, or any other combination thereof.

In some embodiments, the method of analysis comprises determining a dimension of a particle or a cell, the method comprising subjecting said particle or said cell to flow along a flow channel; and repeatedly detecting one or more beams of light, wherein said one or more beams of light are scattered by said particle or said cell, and wherein said one or more beams of light comprise an angular light scattering pattern, wherein said angular light scattering pattern identifies said dimension of said particle or said cell. In some embodiments, the method of analysis comprises determining a dimension of a particle or a cell, the method comprising subjecting said particle or said cell to flow along a flow channel; and repeatedly detecting one or more beams of light, wherein said one or more beams of light are scattered by said particle or said cell, and wherein said one or more beams of light comprise a light scattering spectra, wherein said light scattering spectra identifies said dimension of said particle or said cell.

In some embodiments, the method of analysis comprises processing or analyzing a cell, comprising subjecting said cell to flow along a flow channel and detecting a signal from said cell to identify the cellular size at an accuracy of at least $10^{-5}$ m in a time period of at most 10 minutes. In some embodiments, the method of analysis comprises processing or analyzing a cell, comprising subjecting said cell to flow along a flow channel and detecting a signal from said cell to identify the cellular size at an accuracy of at least $10^{-5}$ m in a time period of at most about 1 minute to about 30 minutes. In some embodiments, the method of analysis comprises processing or analyzing a cell, comprising subjecting said cell to flow along a flow channel and detecting a signal from said cell to identify the cellular size at an accuracy of at least $10^{-5}$ m in a time period of at most about 1 minute to about 2 minutes, about 1 minute to about 3 minutes, about 1 minute to about 4 minutes, about 1 minute to about 5 minutes, about 1 minute to about 10 minutes, about 1 minute to about 15 minutes, about 1 minute to about 20 minutes, about 1 minute to about 25 minutes, about 1 minute to about 30 minutes, about 2 minutes to about 3 minutes, about 2 minutes to about 4 minutes, about 2 minutes to about 5 minutes, about 2 minutes to about 10 minutes, about 2 minutes to about 15 minutes, about 2 minutes to about 20 minutes, about 2 minutes to about 25 minutes, about 2 minutes to about 30 minutes, about 3 minutes to about 4 minutes, about 3 minutes to about 5 minutes, about 3 minutes to about 10 minutes, about 3 minutes to about 15 minutes, about 3 minutes to about 20 minutes, about 3 minutes to about 25 minutes, about 3 minutes to about 30 minutes, about 4 minutes to about 5 minutes, about 4 minutes to about 10 minutes, about 4 minutes to about 15 minutes, about 4 minutes to about 20 minutes, about 4 minutes to about 25 minutes, about 4 minutes to about 30 minutes, about 5 minutes to about 10 minutes, about 5 minutes to about 15 minutes, about 5 minutes to about 20 minutes, about 5 minutes to about 25 minutes, about 5 minutes to about 30 minutes, about 10 minutes to about 15 minutes, about 10 minutes to about 20 minutes, about 10 minutes to about 25 minutes, about 10 minutes to about 30 minutes, about 15 minutes to about 20 minutes, about 15 minutes to about 25 minutes, about 15 minutes to about 30 minutes, about 20 minutes to about 25 minutes, about 20 minutes to about 30 minutes, or about 25 minutes to about 30 minutes. In some embodiments, the method of analysis comprises processing or analyzing a cell, comprising subjecting said cell to flow along a flow channel and detecting a signal from said cell to identify the cellular size at an accuracy of at least $10^{-5}$ m in a time period of at most about 1 minute, about 2 minutes, about 3 minutes, about 4 minutes, about 5 minutes, about 10 minutes, about 15 minutes, about 20 minutes, about 25 minutes, or about 30 minutes. In some embodiments, the method of analysis comprises processing or analyzing a cell, comprising subjecting said cell to flow along a flow channel and detecting a signal from said cell to identify the cellular size at an accuracy of at least $10^{-5}$ m in a time period of at most at least about 1 minute, about 2 minutes, about 3 minutes, about 4 minutes, about 5 minutes, about 10 minutes, about 15 minutes, about 20 minutes, or about 25 minutes. In some embodiments, the method of analysis comprises processing or analyzing a cell, comprising subjecting said cell to flow along a flow channel and detecting a signal from said cell to identify the cellular size at an accuracy of at least $10^{-5}$ m in a time period of at most at most about 2 minutes, about 3 minutes, about 4 minutes, about 5 minutes, about 10 minutes, about 15 minutes, about 20 minutes, about 25 minutes, or about 30 minutes.

In some embodiments, the method of analysis comprises processing or analyzing a cell, comprising subjecting said cell to flow along a flow channel and detecting a signal from said cell to identify the cellular organelle size at an accuracy of at least $10^{-5}$ m in a time period of at most 10 minutes. In some embodiments, the method of analysis comprises processing or analyzing a cell, comprising subjecting said cell to flow along a flow channel and detecting a signal from said cell to identify the cellular organelle size at an accuracy of at least $10^{-5}$ m in a time period of at most about 1 minute to about 30 minutes. In some embodiments, the method of analysis comprises processing or analyzing a cell, comprising subjecting said cell to flow along a flow channel and detecting a signal from said cell to identify the cellular organelle size at an accuracy of at least $10^{-5}$ m in a time period of at most about 1 minute to about 2 minutes, about 1 minute to about 3 minutes, about 1 minute to about 4 minutes, about 1 minute to about 5 minutes, about 1 minute to about 10 minutes, about 1 minute to about 15 minutes, about 1 minute to about 20 minutes, about 1 minute to about 25 minutes, about 1 minute to about 30 minutes, about 2 minutes to about 3 minutes, about 2 minutes to about 4 minutes, about 2 minutes to about 5 minutes, about 2 minutes to about 10 minutes, about 2 minutes to about 15 minutes, about 2 minutes to about 20 minutes, about 2 minutes to about 25 minutes, about 2 minutes to about 30 minutes, about 3 minutes to about 4 minutes, about 3 minutes to about 5 minutes, about 3 minutes to about 10 minutes, about 3 minutes to about 15 minutes, about 3 minutes to about 20 minutes, about 3 minutes to about 25 minutes, about 3 minutes to about 30 minutes, about 4 minutes to about 5 minutes, about 4 minutes to about 10 minutes, about 4 minutes to about 15 minutes, about 4 minutes to about 20 minutes, about 4 minutes to about 25 minutes, about 4 minutes to about 30 minutes, about 5 minutes to about 10 minutes, about 5 minutes to about 15 minutes, about 5 minutes to about 20 minutes, about 5 minutes to about 25 minutes, about 5 minutes to about 30 minutes, about 10 minutes to about 15 minutes, about 10 minutes to about 20 minutes, about 10 minutes to about 25 minutes, about 10 minutes to about 30 minutes, about 15 minutes to about 20 minutes, about 15 minutes to about 25 minutes, about 15 minutes to about 30 minutes, about 20 minutes to about 25 minutes, about 20 minutes to about 30 minutes, or about 25 minutes to about 30 minutes. In some embodiments, the method of analysis comprises processing or analyzing a cell, comprising subjecting said cell to flow along a flow channel and detecting a signal from said cell to identify the cellular organelle size at an accuracy of at least $10^{-5}$ m in a time period of at most about 1 minute, about 2 minutes, about 3 minutes, about 4 minutes, about 5 minutes, about 10 minutes, about 15 minutes, about 20 minutes, about 25 minutes, or about 30 minutes. In some embodiments, the method of analysis comprises processing or analyzing a cell, comprising subjecting said cell to flow along a flow channel and detecting a signal from said cell to identify the cellular organelle size at an accuracy of at least $10^{-5}$ m in a time period of at most at least about 1 minute, about 2 minutes, about 3 minutes, about 4 minutes, about 5 minutes, about 10 minutes, about 15 minutes, about 20 minutes, or about 25 minutes. In some embodiments, the method of analysis comprises processing or analyzing a cell, comprising subjecting said cell to flow along a flow channel and detecting a signal from said cell to identify the cellular organelle size at an accuracy of at least $10^{-5}$ m in a time period of at most at most about 2 minutes, about 3 minutes, about 4 minutes, about 5 minutes, about 10 minutes, about 15 minutes, about 20 minutes, about 25 minutes, or about 30 minutes.

In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most 10 minutes. In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most about 1 minute to about 30 minutes. In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most about 1 minute to about 2 minutes, about 1 minute to about 3 minutes, about 1 minute to about 4 minutes, about 1 minute to about 5 minutes, about 1 minute to about 10 minutes, about 1 minute to about 15 minutes, about 1 minute to about 20 minutes, about 1 minute to about 25 minutes, about 1 minute to about 30 minutes, about 2 minutes to about 3 minutes, about 2 minutes to about 4 minutes, about 2 minutes to about 5 minutes, about 2 minutes to about 10 minutes, about 2 minutes to about 15 minutes, about 2 minutes to about 20 minutes, about 2 minutes to about 25 minutes, about 2 minutes to about 30 minutes, about 3 minutes to about 4 minutes, about 3 minutes to about 5 minutes, about 3 minutes to about 10 minutes, about 3 minutes to about 15 minutes, about 3 minutes to about 20 minutes, about 3 minutes to about 25 minutes, about 3 minutes to about 30 minutes, about 4 minutes to about 5 minutes, about 4 minutes to about 10 minutes, about 4 minutes to about 15 minutes, about 4 minutes to about 20 minutes, about 4 minutes to about 25 minutes, about 4 minutes to about 30 minutes, about 5 minutes to about 10 minutes, about 5 minutes to about 15 minutes, about 5 minutes to about 20 minutes, about 5 minutes to about 25 minutes, about 5 minutes to about 30 minutes, about 10 minutes to about 15 minutes, about 10 minutes to about 20 minutes, about 10 minutes to about 25 minutes, about 10 minutes to about 30 minutes, about 15 minutes to about 20 minutes, about 15 minutes to about 25 minutes, about 15 minutes to about 30 minutes, about 20 minutes to about 25 minutes, about 20 minutes to about 30 minutes, or about 25 minutes to about 30 minutes. In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most about 1 minute, about 2 minutes, about 3 minutes, about 4 minutes, about 5 minutes, about 10 minutes, about 15 minutes, about 20 minutes, about 25 minutes, or about 30 minutes. In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most at least about 1 minute, about 2 minutes, about 3 minutes, about 4 minutes, about 5 minutes, about 10 minutes, about 15 minutes, about 20 minutes, or about 25 minutes. In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most at most about 2 minutes, about 3 minutes, about 4 minutes, about 5 minutes, about 10 minutes, about 15 minutes, about 20 minutes, about 25 minutes, or about 30 minutes.

In some embodiments, the method of analysis comprises a method for processing or analyzing a cell, comprising subjecting said cell to flow along a flow channel and detecting a signal from said cell to identify a population of at least 1,000 cells in a time period of at most 10 minutes. In some embodiments, the method of analysis comprises a method for processing or analyzing a cell, comprising subjecting said cell to flow along a flow channel and detecting a signal from said cell to identify a population of at least 1,000 cells in a time period of at most about 1 minute to about 30 minutes. In some embodiments, the method of analysis comprises a method for processing or analyzing a cell, comprising subjecting said cell to flow along a flow channel and detecting a signal from said cell to identify a population of at least 1,000 cells in a time period of at most about 1 minute to about 2 minutes, about 1 minute to about 3 minutes, about 1 minute to about 4 minutes, about 1 minute to about 5 minutes, about 1 minute to about 10 minutes, about 1 minute to about 15 minutes, about 1 minute to about 20 minutes, about 1 minute to about 25 minutes, about 1 minute to about 30 minutes, about 2 minutes to about 3 minutes, about 2 minutes to about 4 minutes, about 2 minutes to about 5 minutes, about 2 minutes to about 10 minutes, about 2 minutes to about 15 minutes, about 2 minutes to about 20 minutes, about 2 minutes to about 25 minutes, about 2 minutes to about 30 minutes, about 3 minutes to about 4 minutes, about 3 minutes to about 5 minutes, about 3 minutes to about 10 minutes, about 3 minutes to about 15 minutes, about 3 minutes to about 20 minutes, about 3 minutes to about 25 minutes, about 3 minutes to about 30 minutes, about 4 minutes to about 5 minutes, about 4 minutes to about 10 minutes, about 4 minutes to about 15 minutes, about 4 minutes to about 20 minutes, about 4 minutes to about 25 minutes, about 4 minutes to about 30 minutes, about 5 minutes to about 10 minutes, about 5 minutes to about 15 minutes, about 5 minutes to about 20 minutes, about 5 minutes to about 25 minutes, about 5 minutes to about 30 minutes, about 10 minutes to about 15 minutes, about 10 minutes to about 20 minutes, about 10 minutes to about 25 minutes, about 10 minutes to about 30 minutes, about 15 minutes to about 20 minutes, about 15 minutes to about 25 minutes, about 15 minutes to about 30 minutes, about 20 minutes to about 25 minutes, about 20 minutes to about 30 minutes, or about 25 minutes to about 30 minutes. In some embodiments, the method of analysis comprises a method for processing or analyzing a cell, comprising subjecting said cell to flow along a flow channel and detecting a signal from said cell to identify a population of at least 1,000 cells in a time period of at most about 1 minute, about 2 minutes, about 3 minutes, about 4 minutes, about 5 minutes, about 10 minutes, about 15 minutes, about 20 minutes, about 25 minutes, or about 30 minutes. In some embodiments, the method of analysis comprises a method for processing or analyzing a cell, comprising subjecting said cell to flow along a flow channel and detecting a signal from said cell to identify a population of at least 1,000 cells in a time period of at most at least about 1 minute, about 2 minutes, about 3 minutes, about 4 minutes, about 5 minutes, about 10 minutes, about 15 minutes, about 20 minutes, or about 25 minutes. In some embodiments, the method of analysis comprises a method for processing or analyzing a cell, comprising subjecting said cell to flow along a flow channel and detecting a signal from said cell to identify a population of at least 1,000 cells in a time period of at most at most about 2 minutes, about 3 minutes, about 4 minutes, about 5 minutes, about 10 minutes, about 15 minutes, about 20 minutes, about 25 minutes, or about 30 minutes.

In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most 10 minutes. In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most about 1 minute to about 30 minutes. In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most about 1 minute to about 2 minutes, about 1 minute to about 3 minutes, about 1 minute to about 4 minutes, about 1 minute to about 5 minutes, about 1 minute to about 10 minutes, about 1 minute to about 15 minutes, about 1 minute to about 20 minutes, about 1 minute to about 25 minutes, about 1 minute to about 30 minutes, about 2 minutes to about 3 minutes, about 2 minutes to about 4 minutes, about 2 minutes to about 5 minutes, about 2 minutes to about 10 minutes, about 2 minutes to about 15 minutes, about 2 minutes to about 20 minutes, about 2 minutes to about 25 minutes, about 2 minutes to about 30 minutes, about 3 minutes to about 4 minutes, about 3 minutes to about 5 minutes, about 3 minutes to about 10 minutes, about 3 minutes to about 15 minutes, about 3 minutes to about 20 minutes, about 3 minutes to about 25 minutes, about 3 minutes to about 30 minutes, about 4 minutes to about 5 minutes, about 4 minutes to about 10 minutes, about 4 minutes to about 15 minutes, about 4 minutes to about 20 minutes, about 4 minutes to about 25 minutes, about 4 minutes to about 30 minutes, about 5 minutes to about 10 minutes, about 5 minutes to about 15 minutes, about 5 minutes to about 20 minutes, about 5 minutes to about 25 minutes, about 5 minutes to about 30 minutes, about 10 minutes to about 15 minutes, about 10 minutes to about 20 minutes, about 10 minutes to about 25 minutes, about 10 minutes to about 30 minutes, about 15 minutes to about 20 minutes, about 15 minutes to about 25 minutes, about 15 minutes to about 30 minutes, about 20 minutes to about 25 minutes, about 20 minutes to about 30 minutes, or about 25 minutes to about 30 minutes. In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most about 1 minute, about 2 minutes, about 3 minutes, about 4 minutes, about 5 minutes, about 10 minutes, about 15 minutes, about 20 minutes, about 25 minutes, or about 30 minutes. In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most at least about 1 minute, about 2 minutes, about 3 minutes, about 4 minutes, about 5 minutes, about 10 minutes, about 15 minutes, about 20 minutes, or about 25 minutes. In some embodiments, the method of analysis comprises processing or analyzing a cell, comprising subjecting said cell to flow along a flow channel and detecting a signal from said cell to identify the number of cellular mitochondria at an accuracy of at least 95 percent in a time period of at most at most about 2 minutes, about 3 minutes, about 4 minutes, about 5 minutes, about 10 minutes, about 15 minutes, about 20 minutes, about 25 minutes, or about 30 minutes.

Light Scattering Spectral Pattern

In some embodiments, a light scattering pattern may result from one or more beams of light interacting with an analyte and thereafter being detected by one or more photodetectors. In some embodiments, a light scattering pattern may result from one or more beams of light interacting with an object in motion such as a cell. In some embodiments, a light scattering pattern may result from one or more beams of light emanating from a fluorescent dye. In some embodiments, a light scattering pattern may result from one or more beams of lights passing through a light modifying substrate. In some embodiments, a light scattering pattern may result from one or more beams of lights passing through a light scattering control system. In some embodiments, a light scattering pattern may result from one or more beams of lights refracting through a light scattering control system. In some embodiments, a light scattering pattern may result from one or more beams of lights bending through a light scattering control system. In some embodiments, a light scattering pattern may result from one or more beams of lights interacting with an analyte and refracting through a light scattering control system to one or more photodetectors. In some embodiments, a light scattering pattern may result from one or more beams of lights interacting with an analyte and passing through a light scattering control system to one or more photodetectors. In some embodiments, a light scattering pattern may result from one or more beams of lights interacting with an analyte and refracting through a light scattering control system to one or more photodetectors In some embodiments, a light scattering pattern may result from one or more beams of light interacting with one or more beams of light. In some embodiments, a light scattering spectral pattern may be detected by one or more photodetectors upon photoexcitation of an analyte.

Light scattering spectral patterns may vary from analyte to analyte and can help enable classification and identification of analytes. A light scattering spectral pattern may emerge upon photonic displacement from an analyte towards one or more photodetectors. In some embodiments, a light scattering spectral pattern is adjusted based on passage through a light modifying substrate, a light scattering control system, or a light modifying layer. In some embodiments, the light scattering pattern is a spectral pattern. In some embodiments, the light scattering pattern is angular. In some embodiments, the light scattering pattern comprises a spectral pattern. In some embodiments, the light scattering pattern comprises a spectral pattern. In some embodiments, the light scattering pattern comprises an angular light scattering pattern. In some embodiments, the angular light scattering pattern identifies an analyte or cell. In some embodiments, the light scattering spectral pattern identifies an analyte or cell. In some embodiments, a dimension of an analyte or cell may be determined from a light scattering pattern such as an angular light scattering pattern or a light scattering spectral pattern.

Figure 21:
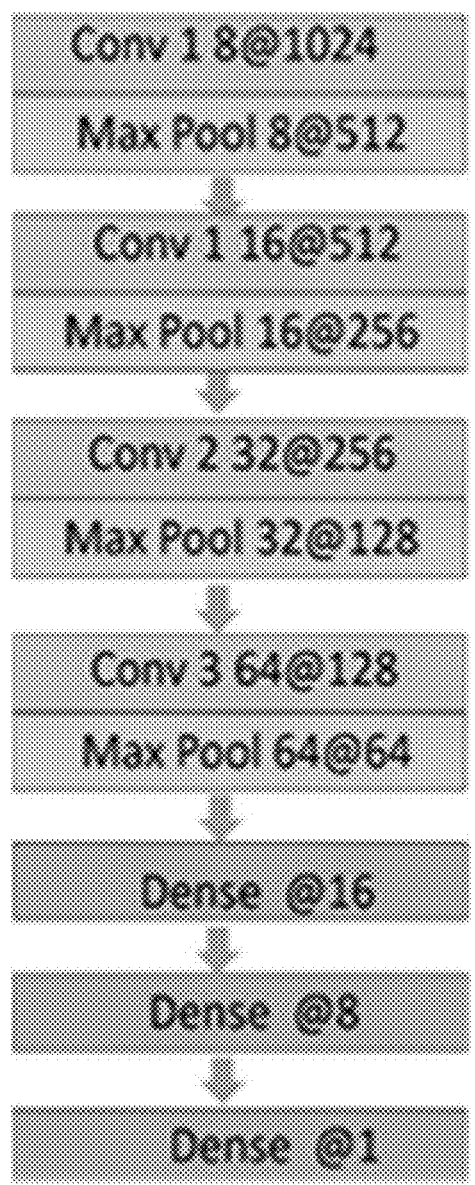
FIG. 21 shows an example of deep-learning network architecture.

In some embodiments, machine learning algorithms may be used to help classify analytes or cells. In some embodiments, the classification confirms a biotherapeutic analytical characterization such as T cell modulation. In some embodiments, the classification comprises classifying a cellular phenotype. In some embodiments, the classification comprises classifying gene expression. In some embodiments, the classification comprises using a machine learning algorithm. In some embodiments, the machine learning algorithm is a convolutional neural network. In some embodiments, the machine learning algorithm operations are shown in FIG. 21.

Blood Sorting

In some embodiments, the device disclosed herein can be used to separate healthy cells from diseased or undesirable cells. In some embodiments, provided herein is a method of analyzing a subject's blood comprising connecting a subject's blood flow to a device or analyte processing device disclosed herein. In some embodiments, the analysis comprises cancer cell detection. In some embodiments, the analysis comprises preparation of a subject's blood prior to analysis. In some embodiments, the analysis further comprises removal of cancer cells. In some embodiments, the analysis comprises intermittent sampling of the subject's blood. In some embodiments, provided herein is a method of spatially identifying one or more markers on an analyte surface, comprising: subjecting the analyte to flow through a flow channel; subjecting the analyte to one or more excitation sources, wherein the one or more excitation sources generates a light scattering pattern of the analyte surface; processing the light scattering pattern algorithmically to generate a topographic map of the analyte surface. In some embodiments, the topographic map comprises a location map of one or more markers. In some embodiments, the topographic map comprises an intensity map of one or more markers. In some embodiments, the topographic map comprises a density map of one or more markers.

Definitions

The term "analyte" or "target" as used herein refers to a molecular species to be detected. Examples include small molecules such as organic compounds, drugs, hormones, lipids, steroids, or metabolites; polynucleotides such as deoxyribonucleic acid (DNA) molecules, ribonucleic acid (RNA) molecules, and peptide nucleic acid (PNA); polypeptides such as proteins, peptides, antibodies, antigens, enzymes, and receptors; as well as tissues, organelles, and other receptor probes.

The term "about" or "nearly" as used herein generally refers to within +/−15%, 10%, 9%, 8%, 7%, 6%, 5%, 4%, 3%, 2%, or 1% of the designated amount.

The term "label" as used herein refers to a molecular structure that can be attached to a molecule (e.g., a target, a probe, or a combination thereof), to make the molecule detectable, distinguishable, traceable, or a combination thereof by providing a characteristic which may not be intrinsic to the target molecule. Examples of labels may include are luminescent molecules (e.g., fluorophores), reduction-oxidation (redox) species, or enzymes. In some cases, labels may comprise fluorophores with long lifetimes, such as, for example, lanthanide chelates and transition metal chelates, which are luminescent or phosphorescent.

As used herein, the terms "polynucleotide", "oligonucleotide", "nucleotide", "nucleic acid" and "nucleic acid molecule" generally refer to a polymeric form of nucleotides (polynucleotides) of various lengths, either ribonucleotides (RNA) or deoxyribonucleotides (DNA). Examples of nucleotide sequences are sequences corresponding to natural or synthetic RNA or DNA including genomic DNA and messenger RNA. The length of the sequence can be any length that can be amplified into nucleic acid amplification products, or amplicons, for example, up to about 20, 50, 100, 200, 300, 400, 500, 600, 700, 800, 1,000, 1,200, 1,500, 2,000, 5,000, 10,000 or more than 10,000 nucleotides in length, or at least about 20, 50, 100, 200, 300, 400, 500, 600, 700, 800, 1,000, 1,200, 1,500, 2,000, 5,000, 10,000 or 10,000 nucleotides in length.

As used herein, the terms "peptide," "polypeptide," and "protein" are used interchangeably, and generally refer to a compound comprised of amino acid residues covalently linked by peptide bonds. Polypeptides may include any peptide or protein comprising two or more amino acids joined to each other by peptide bonds. Examples of polypeptides may include, for example, biologically active fragments, substantially homologous polypeptides, oligopeptides, homodimers, heterodimers, polypeptides and variants thereof, modified polypeptides, derivatives, analogs, fusion proteins, or combinations thereof. A polypeptide may be a natural peptide, a recombinant peptide, or a combination thereof.

In the following detailed description, reference is made to the accompanying figures, which form a part hereof. The drawings illustrate embodiments of the present disclosure and, together with the detailed description, serve to explain the principles of the present disclosure. The drawings may not necessarily be in scale so as to better present certain features of the illustrated subject matter. In the figures, similar symbols identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments, uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, devices, methods, or combinations thereof described herein may be embodied as integrated components or as separate components.

As used herein, the singular forms "a", "an", and "the" include plural references unless the context clearly dictates otherwise.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements, operations, or steps but not the exclusion of any other elements or steps.

The term "Optical setup" as used herein may be used interchangeably with "light scattering control system." The terms "light modifying element" and "light modifying substrate" as used herein may be used interchangeably.

The term "computer processing" as used herein may be used interchangeably with "processing."

The term "analyte processing device" as used herein may be used interchangeably with "device".

The term "scattering" as used herein can refer to scattering as either excitation light scattered from an analyte or the excitation light absorbed by whole or part of an analyte and/or excitation light re-emitted (directly or indirectly) at a different wavelength from the excitation light.

The term "topographic map" as used herein can refer to a data set comprising information on one or more characteristics, the one or more characteristics comprising the location on the analyte surface of the one or more analyte surface characteristics, the intensity of one or more signals emitted from the one or more analyte, and/or the density of the one or more characteristics on the analyte surface at the spatial location. In some cases, a topographic map may further comprise a cell cartography map.

In some cases, a topographic map comprises a data set comprising information on one or more cell surface markers, the information comprising the location on the cell surface of the one or more cell surface markers, the intensity of one or more signals emitted from the one or more cell surface markers, and/or the density of the markers on the cell surface at the spatial location.

Topographic mapping can be performed for analytes to describe many characteristics including presence of dyes, presence of antibodies, presence of lipids, presence of nucleotides, cell type, cell disease state, presence of other analytes, velocity of a region, acceleration of a region, density of an analyte, momentum of a region, luminescence of a region, brightness of a region, light scattering pattern of a region, light wavelength, light polarization, light pattern of a region, scattered light of a region, or light scattered.

As used herein, "chemical functionalization" may refer to a chemical group linked ionically or covalently to one or more surfaces of a chip or analyte processing device.

As used herein, "three-dimensional structure" can refer to the chemical and mechanical features of an object or analyte encoded in a three-dimensional plane, as well as any other associated characteristics.

As used herein, "characteristics" may refer to information related to mechanical features of an object or analyte. Characteristics include presence of dyes, presence of antibodies, presence of lipids, presence of nucleotides, cell type, cell disease state, presence of other analytes, velocity of a region, acceleration of a region, density of an analyte, momentum of a region, luminescence of a region, brightness of a region, light scattering pattern of a region, light wavelength, light polarization, light pattern of a region, scattered light of a region, or scattered light.

As used herein, "cellular analysis" can refer to cellular function study, cellular disease diagnostics, monitoring of cellular response to molecular therapeutics, cellular structure discovery, cellular toxicity analysis, regenerative cell analysis, forensic study, field study, cellular heterogeneity.

The term "QCNN" refers to quantized convolutional neural network. The term "CMM" refers to Contextual Multi-Scale Multi-Level Network. The term "CMP" refers to chemical mechanical polishing.

EXAMPLES

The following examples are intended to illustrate but not limit the disclosed embodiments.

Example 1

Figure 17:
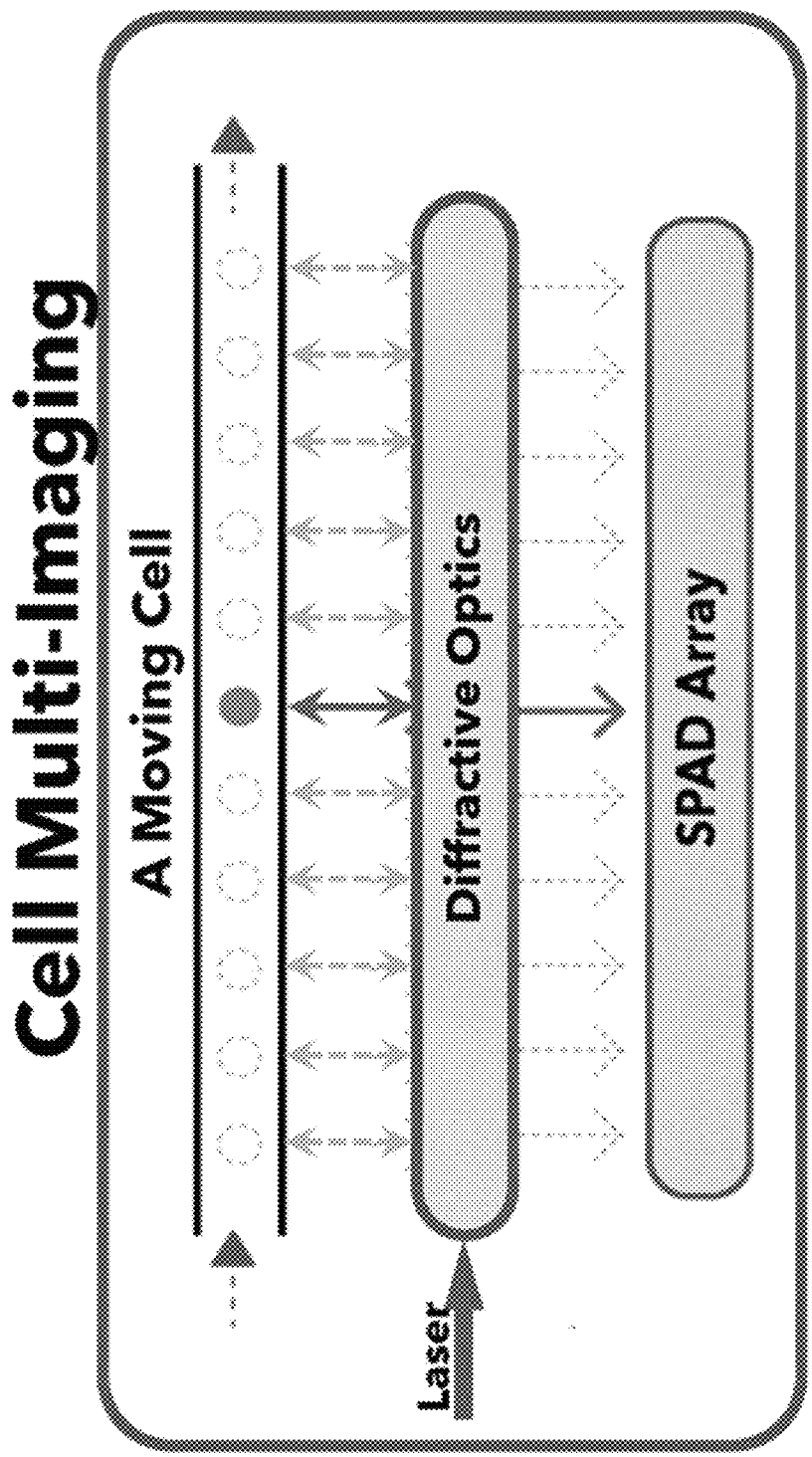
FIG. 17 shows a schematic of cell-analysis solution with diffractive optics to probe dynamic cells at multiple locations in a microfluidic channel.

Simulation and Modelling of Time Independent Correlation Spectroscopy Via a SPAD Array The limitations of existing devices can be overcome by integrating novel diffractive optics, microfluidics, and SPAD imaging into a compact bench-top system to achieve unprecedented throughput and accuracy in a cell imaging device. This device flows cells in a microfluidic channel, probes them repeatedly using a proprietary mechanism that diffracts a single laser light to probe cells at spatially separate locations along the microfluidic channel, and collects the excitation photons using a CMOS SPAD array chip (FIG. 17). Rather than excitation by a single pulsed laser, the cells can be probed at many locations throughout the channel. This design allows for the ability to have many parallel microfluidic channels on the same setup. The initial designs are for 32 excitation stations and 32 parallel microfluidic channels, with a 512×512-pixel SPAD array, assigning 16×16 SPAD pixels to each probing station. The system is substantially faster, and more accurate, in detecting rare-targets than state-of-the-art flow cytometers.

Another aspect of the process is to use an array of single-photon-avalanche-diodes or SPADs to create the data points required for classification. The idea is roughly as follows: a cell, distinguishable by a fluorescent dye, is targeted by a pulsed laser synchronized with the timing of pixels of SPAD arrays. The emitted photon from the fluorescent dye is captured and detected by an SPAD and the Time of Flight (ToF) of the photon (time between the laser excitation of the dye and photon detection by the SPAD) is recorded by the photodiode circuit. This process is repeated many times and the array of TOF data for a given cell is generated. The collective distribution of the TOF data is then analyzed to classify the cell. Since each TOF data point is in theory independent of the other ones, the overall distribution of the TOF data has vastly more power for discrimination and classification of the cell types, compared to any other known method. Cell Calling (CC) is the process of analyzing data for each individual cell to give it an exact classification. Unlike many existing systems, the CC can not only characterize the overall statistics of the population of the cells, but rather, is able to classify (or call) every individual cell. The input to the classifier is the array of TOF data measured at each station where the cell is excited many times with single photons and the array of TOF data is recorded.

Figure 18A:
FIG. 18A shows examples of distributions of TOF photons.
Figure 18B:
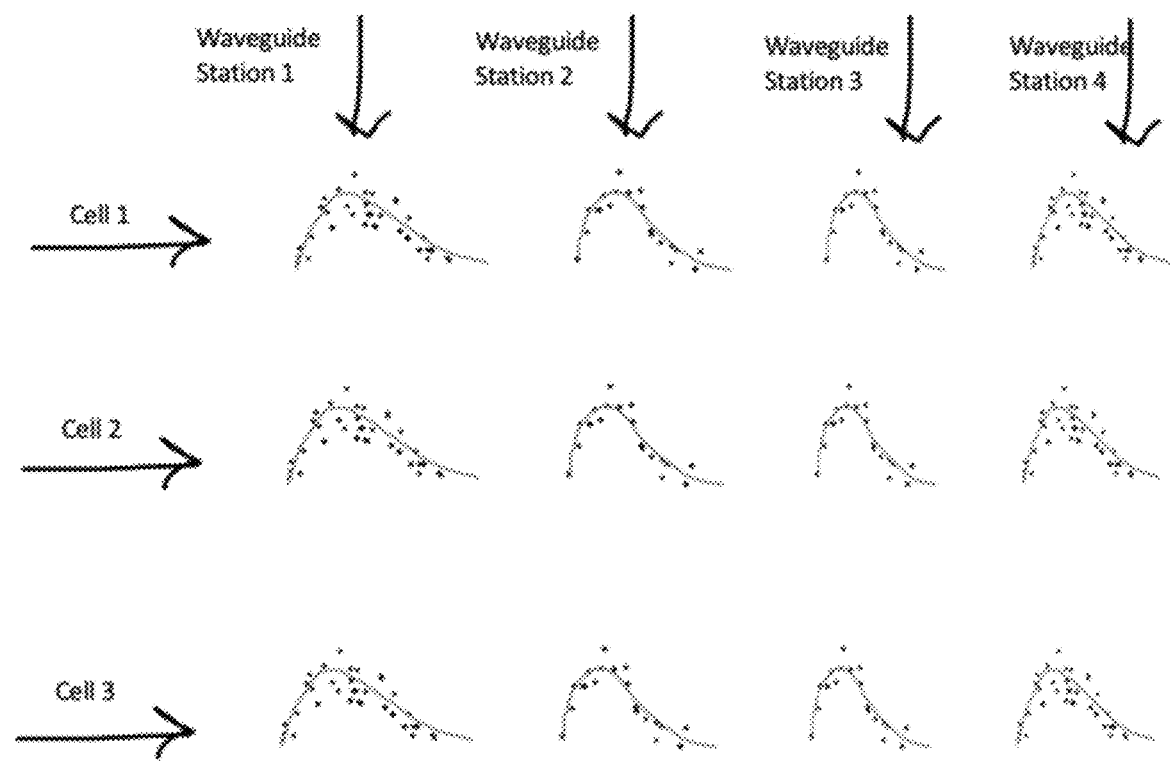
FIG. 18B shows examples of distributions of TOF photons, one for a cell in a given waveguide.

FIG. 18A and FIG. 18B show the TOF data points for a single cell in 4 excitation stations. In each station, the cell is zapped N times by single photon emissions. Each photon then creates an avalanche effect. TOF then measures the time between the emission of the photon and the current triggered by the avalanche effect. The cell then moves to the next station when it is again zapped by N new photons. This process is repeated M times. As such, there are a total of N×M data points, each corresponding to TOF of a photon in a given station as shown in FIG. 18A.

Another aspect of the invention is that the multitude of the TOF data points can be analyzed to classify a cell much more accurately than other methods that rely on single (or few) value excitations. In particular: at each station, instead of computing a single number (e.g., the average) of TOF data, one can now have access to all individual data points. This allows for classification of the characteristics of the TOF data beyond simple statistical measure (e.g., the mean and/or variance) and using the full distribution of the TOF data. As cells "roll" into new stations, the process is repeated. The fixed or systemic process noise at a new station is independent of the fixed or systemic process noise in another station, so increasing the number of stations can be used to further increase the overall system signal-to-noise ratio (SNR). Furthermore, by capturing raw data points for all cells in all stations, further statistical analysis can exploit the potential correlations between the measurements of different cells and possible systemic noise in different channels and stations.

Figure 19:
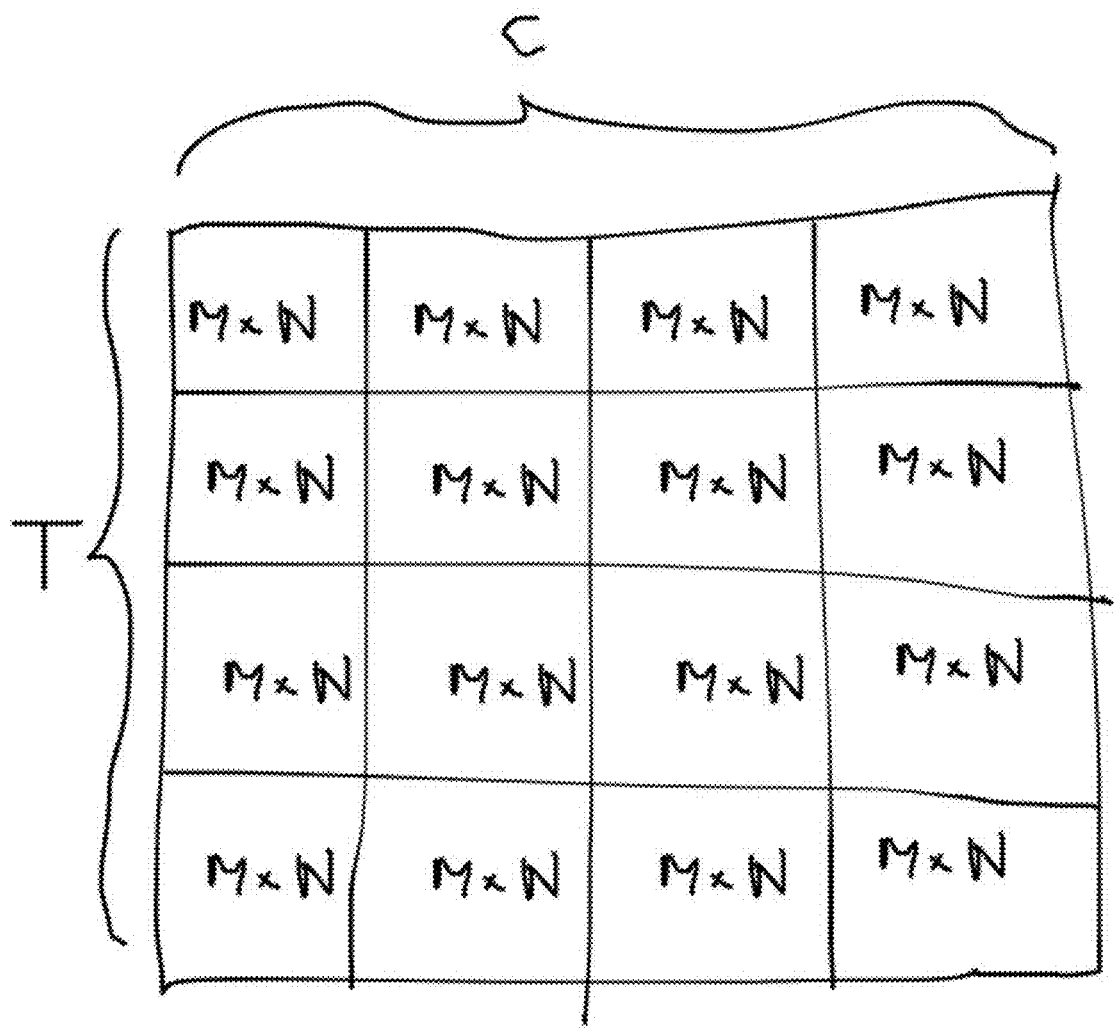
FIG. 19 shows examples of a M by N array of TOF data.

If an equal number of cells, C, passes through each of the channels and the total number of channels is T, then all the captured data can be presented in a composite matrix, with C×T sub-matrices, each of size N by M as in FIG. 19. This device continuously circulates the cell samples through the sensing channel, where a stationary laser probes each cell N-times. Therefore, instead of a cell being probed by lasers at separate locations, each cell is probed by the same laser N-times.

The TOF data in the above matrix can be analyzed to "call" the cells. Calling a cell is the process of making a decision about whether the cell is tagged by a particular dye in the staining process. This characteristic of the distribution of the TOF data is a strong indicator of the existence of the tag on the cell. In this embodiment, both local and global signal processing and machine learning algorithms to call cells. A local algorithm runs on each of the M×N blocks of data for a given cell. Negative cases are screened via a quick calculation that is run by on the chip itself, increasing the efficiency of the device.

More elaborate algorithms may run on either the local hardware or may also run in the cloud. A global algorithm analyzes not only single M by N cell data, but also the cell data in a whole row of cells that pass through the same channel, or even all cell data from all channels as a whole to compensate for global systemic noises and correlations. The algorithms used may include simple mean/variance tests, maximum-likelihood fitting of the distribution of the TOF data, or more elaborate machine learning algorithms, such as deep-learning neural networks. As shown in the figures, the potential for scale and accuracy are greater with the benefits of Time Independent correlation spectroscopy via a SPAD array.

Example 2

Closed Loop Microfluidic Imaging Channel

Figure 20:
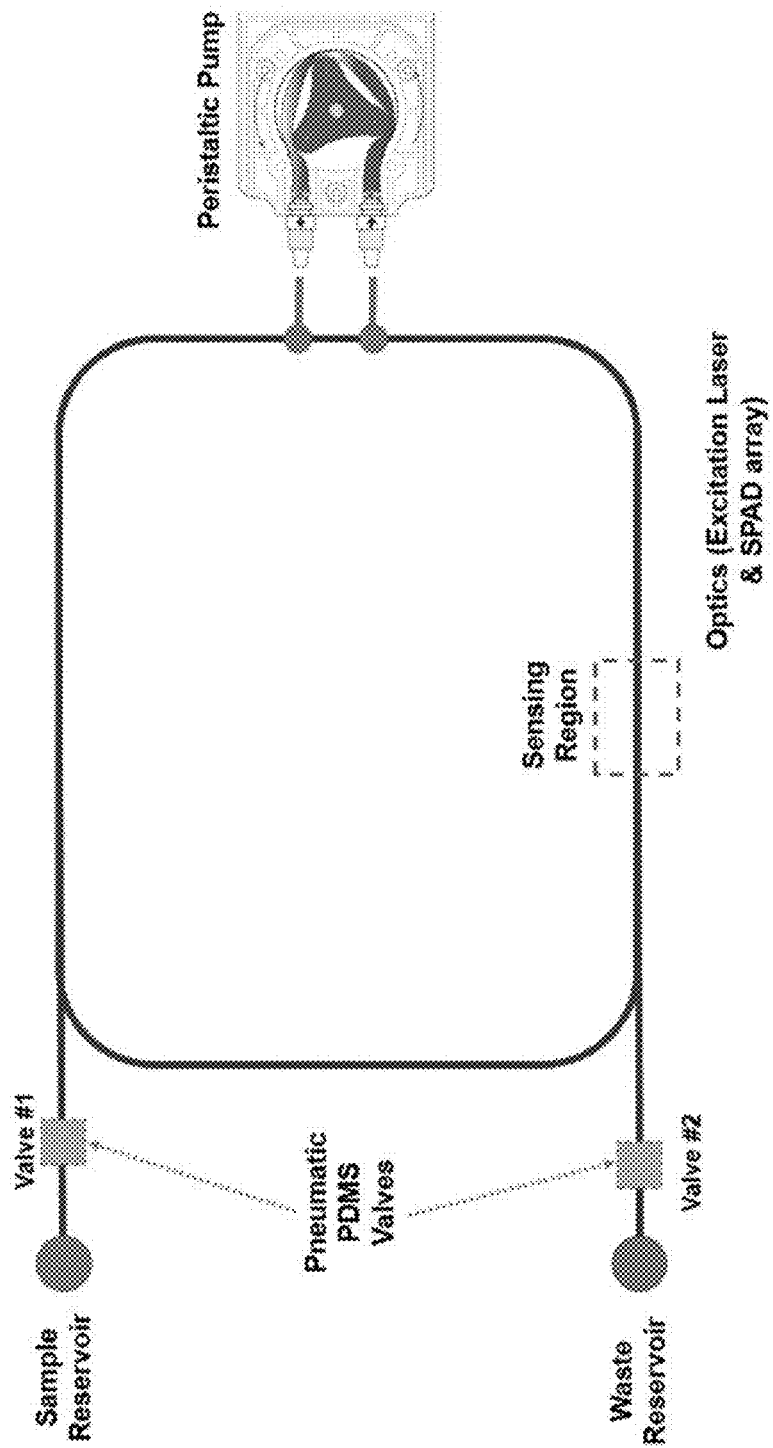
FIG. 20 Schematics of an example of a closed loop microfluidic circuit.

A closed-loop microfluidic based TCSPC system can probe individual targets multiple times, using a single stationary laser. The system comprises a microfluidic chip connected to a controllable microfluidic-compatible peristaltic pump that initiates flow and can circulate the sample. To emulate the process of probing individual cells at different locations in the integrated microfluidic chip, one can circulate the cell sample for N=100 iterations in the microfluidic channel while utilizing a single laser focal point, enabling each individual cell to be probed at N different positions, with the assumption that the cell changes its orientation during each recirculation. A closed loop microfluidic based TCSPC system (FIG. 20) further comprises a sample reservoir, a waste reservoir, two pneumatically driven valves (one for each reservoir) able to control sample flow, an inlet/outlet for the peristaltic pump, and a microfluidic channel with a single sensing region for probing via laser. This device continuously circulates the cell samples through the sensing channel, where a stationary laser probes each cell N-times. Therefore, instead of a cell being probed by lasers at separate locations, each cell is probed by the same laser N-times.

Device operation comprises 3 modes of operation: (1) sample introduction; (2) sample circulation; and (3) sample removal. The peristaltic pump operates at a constant flow rate, with either (1) only valve #1 open; (2) both valves closed; or (3) only valve #2 open. Beginning with "sample introduction", valve #1 is opened at the sample reservoir, allowing the peristaltic pump to introduce the sample to the microfluidic channel, and then closed once the targeted volume is achieved, initiating mode 2. "Sample removal" begins after N-circulations have been completed by opening valve #2, effectively removing the sample from the microfluidic channel. These steps are repeated until the whole volume in the sample reservoir is evaluated. The valves are actuated via a syringe pump that causes a flexible polydimethylsiloxane (PDMS) membrane to open and seal each valve.

Figure 11:
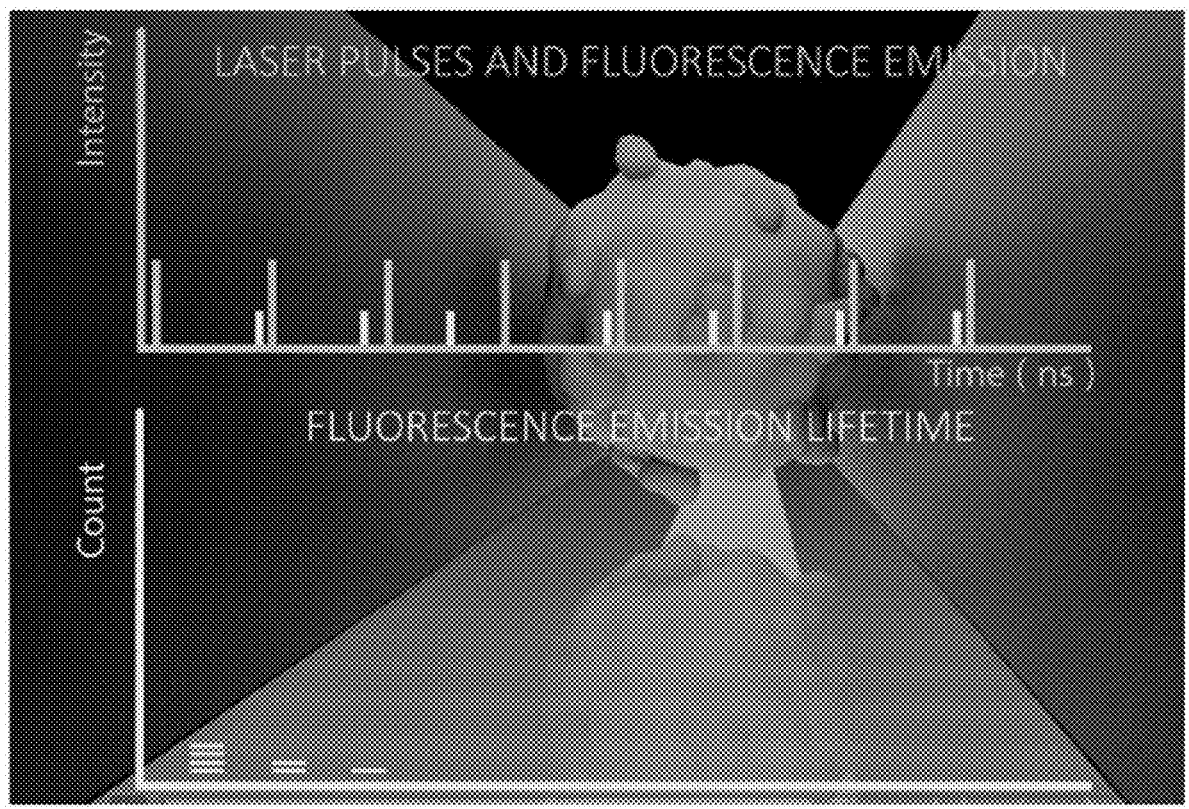
FIG. 11 shows an example of a distribution of the time-of-flight intervals computed for each cell. Each pulse excitement (green bar on top chart) produces an avalanche that leads to a current that follows it (the yellow bar on top chart). A time-of-flight is the time interval between these two events. The distribution of these TOF events are accumulated (the bottom chart).
Figure 12:
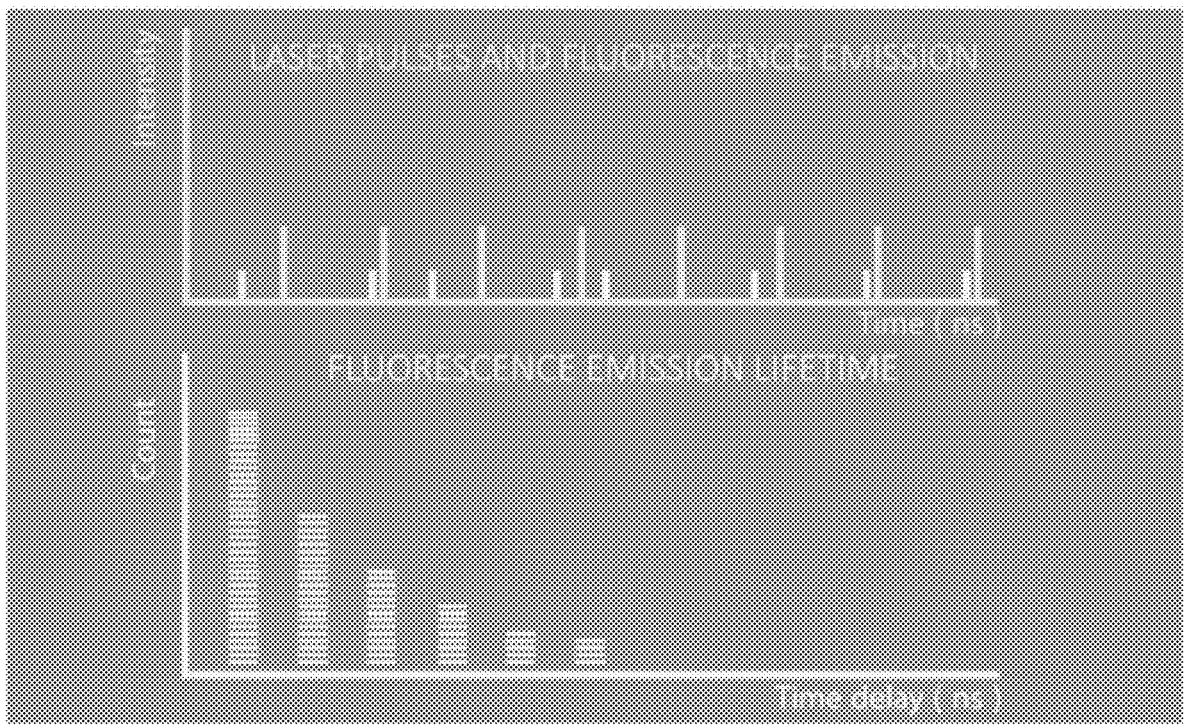
FIG. 12 shows an example of a distribution of the time-of-flight intervals are computed for each cell. Each pulse excitement (green bar on top chart) produces an avalanche that leads to a current that follows it (the yellow bar on top chart). A time-of-flight is the time interval between these two events. The distribution of these TOF events are accumulated (the bottom chart).
Figure 13:
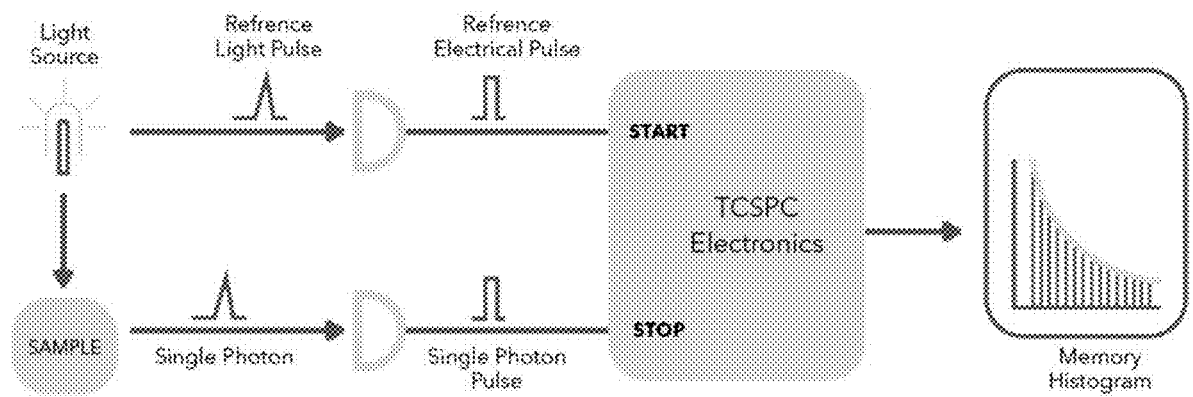
FIG. 13. shows the fate of light sources within time correlated single photon counting (TCSPC).

The microfluidic channel and pneumatic valves are constructed as a single multilayer (PDMS) device, consisting of overlapped fluidic and control channels (that reside in different layers) that are separated by a thin flexible PDMS membrane. Increased pressure in the control channel results in the deformation of the PDMS membrane and closing of the fluidic channel. The microfluidic chips is manufactured through standard PDMS soft-lithography techniques using an SU-8 mold. PDMS channels obtained through replica molding are bonded onto glass slides via plasma-activated bonding to create each device. The controllable peristaltic microfluidic pump can be obtained either commercially, or 3D printed via open-source methods, and allows for cells to flow in either direction through the channel at a controlled flow rate. A monochromatic pulsed laser probes the passing cells at a rate of 80 MHz. The SPAD based TCSPC system collects photons over 1 ms frames, creating a histogram of arrival times for each frame. The total number of photons and quantized arrival times are recorded. A synchronized confocal camera with zoom factor of 60× captures a single image for each 1 millisecond frame. Characteristics of the resulting fluorescence emission intensity and fluorescence intensity count are embodied in FIG. 11 and FIG. 12. The photon input into the TCSPC memory histogram is shown in FIG. 13.

The device is calibrated using 5-15 µm polystyrene beads in a controlled environment, where 100 µl PBS-based bead suspension solution containing roughly $10^5$ polystyrene beads are prepared with approximately $10^2$ fluorescent polystyrene beads added at a $10^{-3}$ ratio. The final solution is then added to the sample reservoir. The beads are circulated 100 times at a speed of ~100 µL/min. Each circulation takes roughly 1 minute, creating ~$10^5$ image data points per circulation. The number of images is approximately equal to the total number of beads and the sample is circulated 100 times to create a total of ~$10^7$ image data points. Validation is then performed using a similar sample where the polystyrene beads are replaced with fluorescently tagged and untagged cells from a cell line.

Results

Figure 10A:
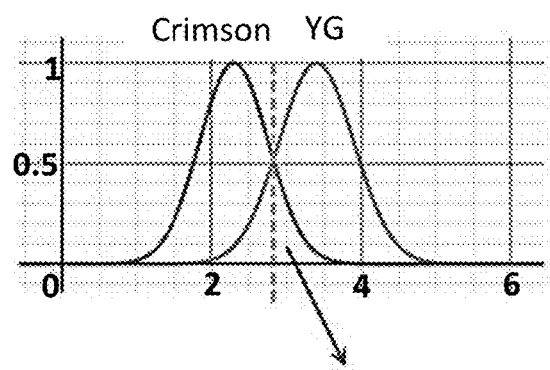
FIG. 10A shows a comparison of measurement sensitivity of optical signals from dyed microspheres between time correlated single photon counting imaging and uncorrelated time lapse imaging.
Figure 10A:
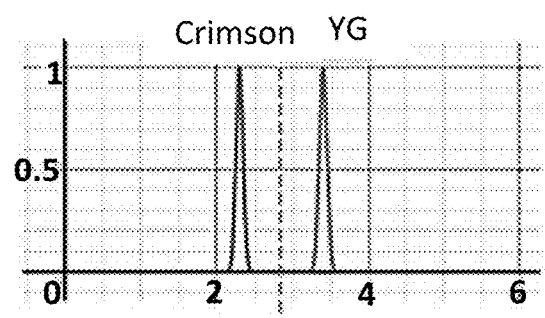
Figure 10B:
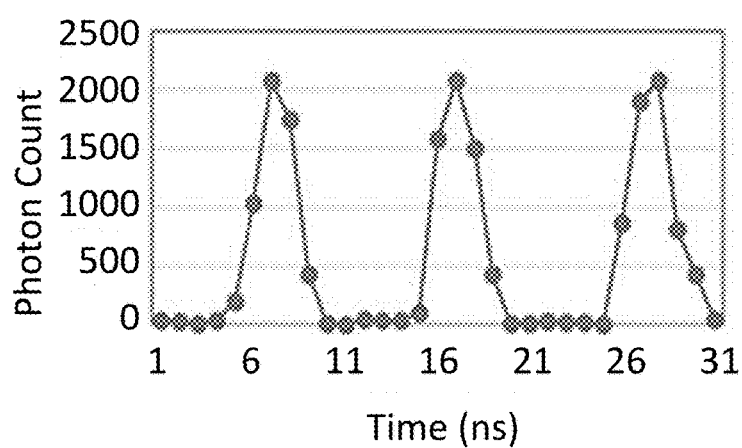
FIG. 10B shows the error rate as a function of photon count, for various separation between average lifetimes.

Photon counts register as a function of time resembling FIG. 10B. As the concentration of tagged beans is chosen to be low, the photon count over time demonstrates cleanly separated spikes with arrival times that are Poisson distributed with mean of 1 sec and p-value <5%. This allows for creation of training data for a deep-learning classifiers.

Example 3

Cellular Detection within a Mouse Tumor Model

One way to demonstrate the validity of the device is through detecting cancer cells in syngeneic mouse models. A MC38 syngeneic mouse tumor model is used, where tumor cells are mixed with, or infiltrated by, other immune cells, proteins, and biological artifacts to further demonstrate the robustness of cellular detection.

Methods

A 300 mg standard sample is digested into a single cell 100 ul solution, prepared, and successively diluted. Starting at 5% concentration (95% water) ten independent samples are run through a MaxQUANT Analyzer-10 to get a count of the number of detected targets. Ten separate samples are simultaneously analyzed through the microfluidic device described herein with circulation counts of N=100. The standard sample solution is then diluted 5× (by diluting 1 part of the current solution with 4 parts water), and the same experiment is repeated 10 times. A three-tag classifier for CD45+CD11b+Csf1R+ is trained using Rhodamine B (RB), Alexa Fluor 633 (AF633) and ATTO 655 (AT655) fluorophores. These dyes are chosen to have the same solvent, have well separated average lifetimes (1.68 ns, 1.0 ns and 3.6 ns respectively), and have maximum excitation wavelengths close to a 638 nm laser. Individual training data is collected for each of the dyes using the method in Example 1. Next, training of 7 separate classifiers for each of the 7 possible combinations where at least one dye is present: RB+AF633+AT655+, RB+AF633+AT655−, RB+AF633−AT655+, RB−AF633+AT655+, RB+AF633−AT655−, RB−AF633+AT655−, RB−AF633−AT655+. To create training data for each case, sampling is done from positive frames for each individual dye that is supposed to be present, and then added to the (non-normalized) histograms of lifetimes together. Once a sample is selected for a set, it is removed to avoid contamination of training and test data. For example: to create training data for RB+AF633+AT655− a random positive frame for RB and a random frame from AF633 data are chosen and the two histograms are added together to form a positive frame. A classifier is then built using a 1-out method: that is, data for a case is taken to be positive, vs data for all the other cases as negative. These markers are present in 80%+ of tumor cells in MC38. Prior to analysis, the solution is diluted with mouse PBMCs (C57BL/6). This enables testing of the robustness of the detection and identification capabilities of the microfluidic device with higher density of cells within injection samples.

Results

The microfluidic device and system detects tumor cells with probability of >50% at concentrations of 1 in $10^5$ cells. These results demonstrate that oversampling cells in the TCSPC microfluidic system can outperform commercial flow-cytometers in detecting rare cell populations of human cells.

Example 4

Detecting Rare Cancer Cells from In Vivo Tissue Samples

To verify that the proposed system can analyze actual human cancer cell samples and detect cancer cells in extremely low concentrations in vivo, syngeic cancer cell samples are used for testing the devices provided herein.

Methods

A 300 mg cellular sample of a Syngeic mouse model annotated by a vendor's lab is digested into a single cell 100 μl solution, prepared, and successively diluted. Starting at 5% concentration (95% water) ten independent samples are run through a MaxQUANT Analyzer-10 to get a count of the number of detected targets. Ten separate samples are simultaneously analyzed through the microfluidic device described herein with circulation counts of N=100. The standard sample solution is then diluted 5× (by diluting 1 part of the current solution with 4 parts water), and the same experiment is repeated 10 times. A three-tag classifier for EpCam+CD166+CD44+ is trained using Rhodamine B (RB), Alexa Fluor 633 (AF633) and ATTO 655 (AT655) fluorophores. Individual training data is collected for each of the markers using the method in Example 1. Next, training of 7 separate classifiers for each of the 7 possible combinations where at least one marker is present: To create training data for each case, sampling is done from positive frames for each individual dye that is supposed to be present, and then added to the (non-normalized) histograms of lifetimes together. Once a sample is selected for a set, it is removed to avoid contamination of training and test data. For example: to create training data for RB+AF633+ AT655− a random positive frame for RB and a random frame from AF633 data are chosen and the two histograms are added together to form a positive frame. A classifier is then built using a 1-out method: that is, data for a case is taken to be positive, vs data for all the other cases as negative. These markers are present in non-small cell lung cancer cells. Prior to analysis, the solution is diluted with human PBMCs. This enables testing of the robustness of the detection and identification capabilities of the microfluidic device with higher density of cells within injection samples.

Results

The microfluidic device and system detects tumor cells with probability of >50% at concentration of 1 cell in $10^5$ cells. This demonstrates a distinct advantage of imaging with TCSPC microfluidic devices.

Example 5

Machine Learning Classifiers for Fluorescence Detection from Lifetime Histograms Once the microfluidic device is calibrated and clear excitation regions are visible, machine learning classifiers for individual fluorescence tags in two steps are implemented.

Methods

Collection of Training Data with Real and Simulated Signals

To collect training data, a simple aggregator filter is used to detect individual events. Since the concentration of the beads as well as their total number is roughly known, we can verify and calibrate the detection algorithm. The aggregator filter acts as a low specificity classifier to identify potential groups of frames corresponding to a target detection. For each frame that triggers a detection, the microscope image taken in the vicinity is manually examined (capturing one camera image per frame). One or more frames where the beads are visually verified to exist are then selected as "positive" data samples. Random frames where beads do not exist are also collected as negative data point. Both negative and positive data points are then split into 80% training, 10% validation and 10% test. Alexa Fluor 633 (AF633) and Alexa Fluor 647 (AF647) fluorophores are used, which have lifetimes of 3.2 ns and 1.0 ns respectively and have excitation wavelengths close to a 638 nm red laser, allowing easy augmentation of the training data with simulated lifetime data. Background noise is estimated from negative frames and incorporated into the simulated data. The optimal percentage of simulated data to be added to the training set is determined through standard k-fold validation. Several architectures can be used to train the Deep-learning Classifier. A simple 1D convolutional network variant inspired by those as shown in FIG. 21 is used.

Results

The beads can be detected with false-negative rate <0.5 and false-positive rate <$10^{-5}$ as verified through k-fold cross-validation. This represents a greater efficiency and precision in fluorescence detection for cellular applications.

Example 6

Fabrication of Microfluid Channel

Figure 14:
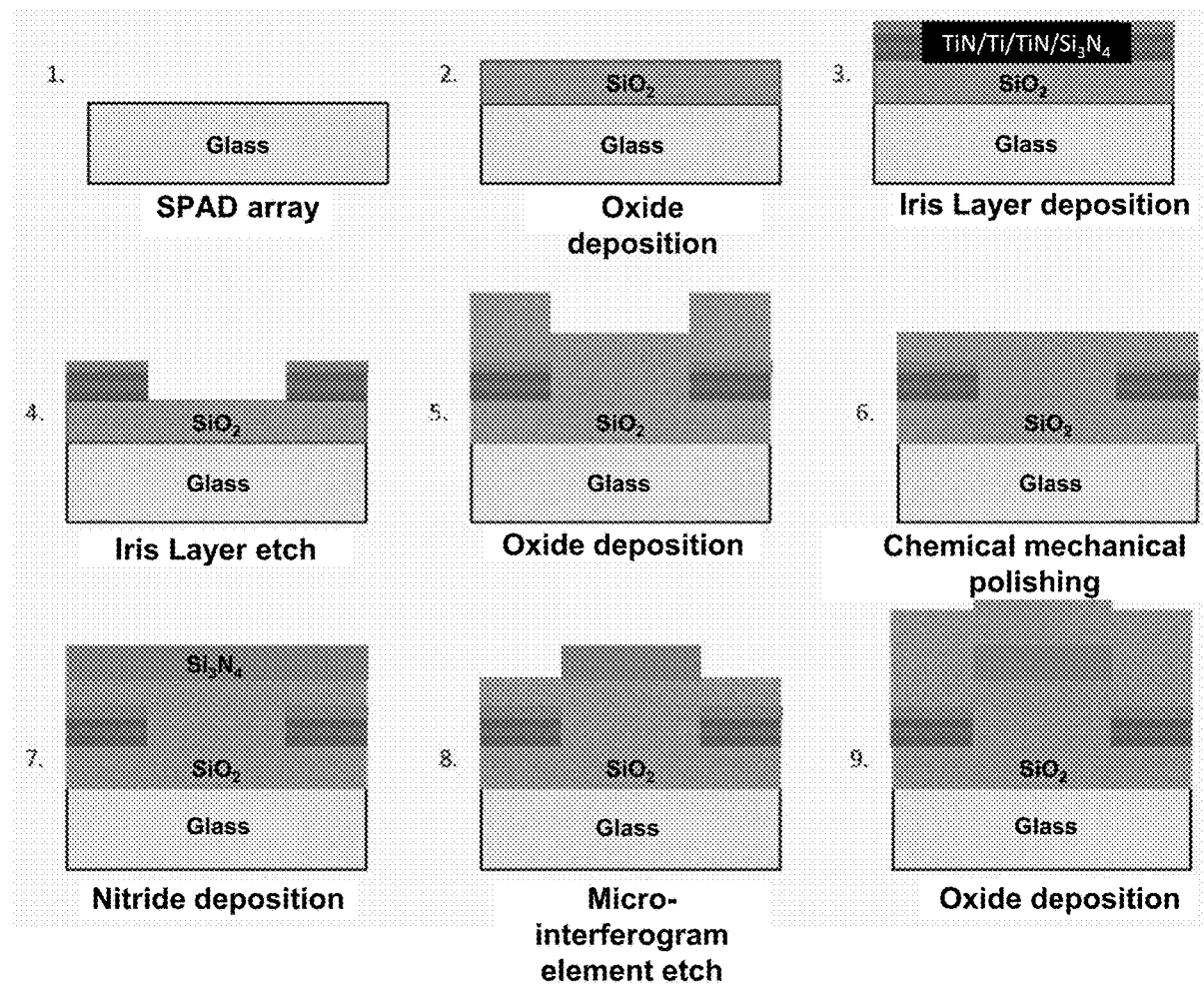
FIG. 14 illustrates operations 1-9 in fabrication of a microfluidic channel for imaging via uncorrelated time lapse microscopy.
Figure 15:
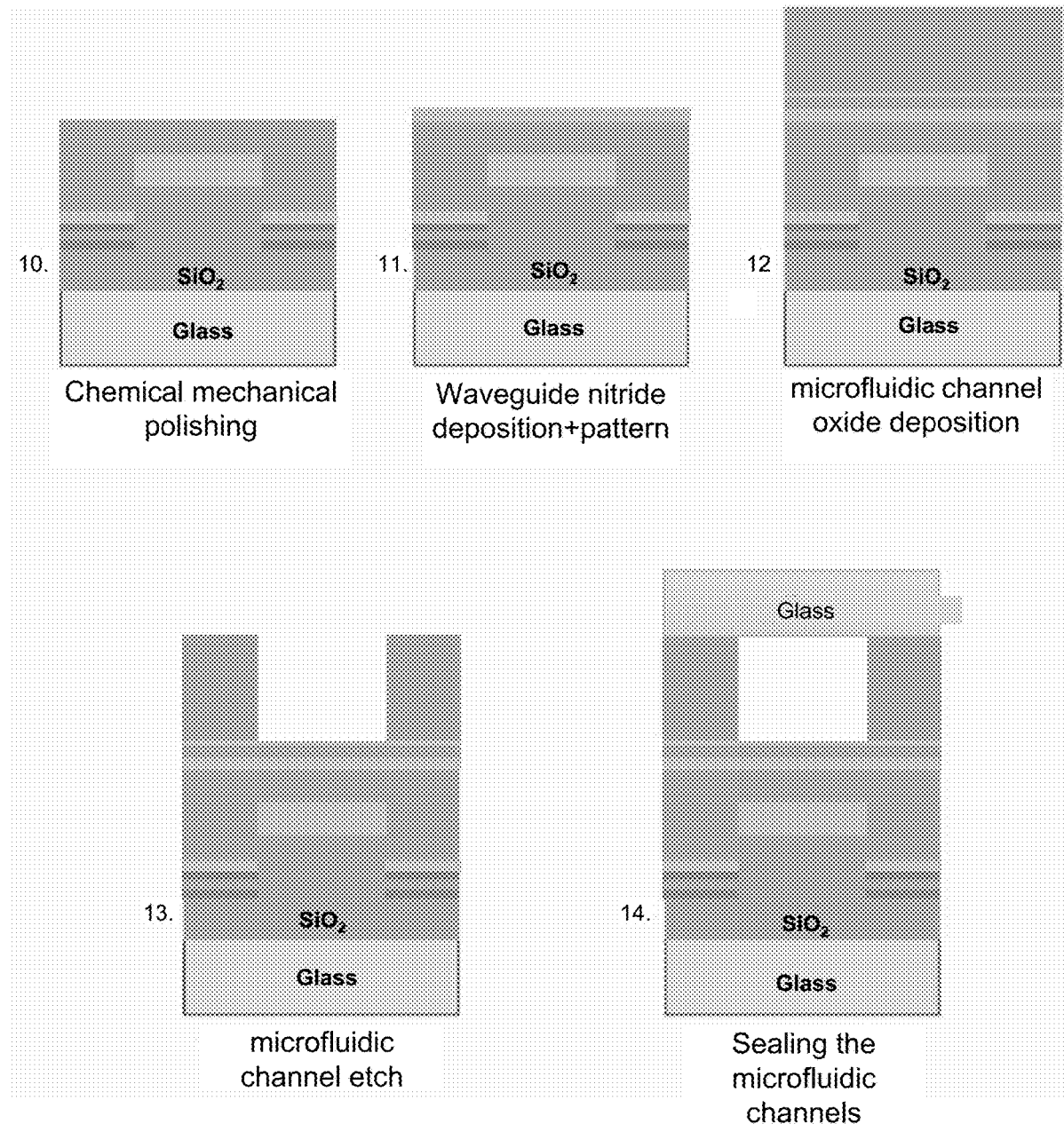
FIG. 15 illustrates operations 10-15 in fabrication of a microfluidic channel of the device described herein.

Microfluid channel is first prepared by placing a SPAD array attached to a glass layer as shown in FIG. 14. Thereafter, above the SPAD array and glass $SiO_2$ is deposited, forming a second layer above the glass and SPAD array. Third, an iris layer comprising individual layers of TiN, Ti, TiN, and $Si_3N_4$ is deposited above the oxide layer. The iris layer is then etched to yield two sides of iris layers as shown in step 3. $SiO_2$ is filled in between the etched region as shown in step 5 and is etched into a new layer of $SiO_2$ in step 6. Another layer of $Si_3N_4$ is deposited above the $SiO_2$, and then etched into a micro-interferogram element shown in step 8. More $SiO_2$ is then added above the $Si_3N_4$ subsection as shown in step 9 layer and leveled via chemical mechanical polishing (CMP). As shown in step 11 of FIG. 15, a thinner layer of $Si_3N_4$ is deposited as a waveguide, followed by a microfluidic channel oxide deposition in step 12. In step 13, the microfluidic channel is etched, and the microfluidic channel is ready for use following step 14 comprising sealing the microfluidic channel with glass. The microfluidic channel is thus prepared for uncorrelated time lapse microscopy of analytes described herein.

Example 7

Size Measurement of a Population of Microspheres Moving Through Analyte Processing Device The analyte processing device signal quality is compared with time correlated single photon counting via crimson fluorophore or YG fluorophore labeled microspheres. The calculated lifetimes of the measured decays are compared using CMM and QCNN methods. The fluorophores for imaging are crimson fluorescent microspheres (F8831, Fluo-Sphere Polystyrene Microspheres, Thermo Fisher, UK), and yellow-green (YG) fluorescent microspheres (F8836, FluoSpheres Polystyrene Microspheres, Thermo Fisher, UK). Microsphere sizes are synthesized to a 10 μm radius on average. Microspheres are dissolved in an aqueous solution with a concentration of $3.6 \times 10^5$ beads/ml. Before pumping into the flow channel, the two steady sample solutions' fluorescence lifetimes are measured using a commercial PMT system (FluoroCube Extreme, Horiba Scientific, UK) as a reference. The two samples show a multiexponential decay feature, and their lifetimes are calculated by commercial software for multiexponential decay fitting (DAS6, Horiba Scientific, UK).

Figure 9A:
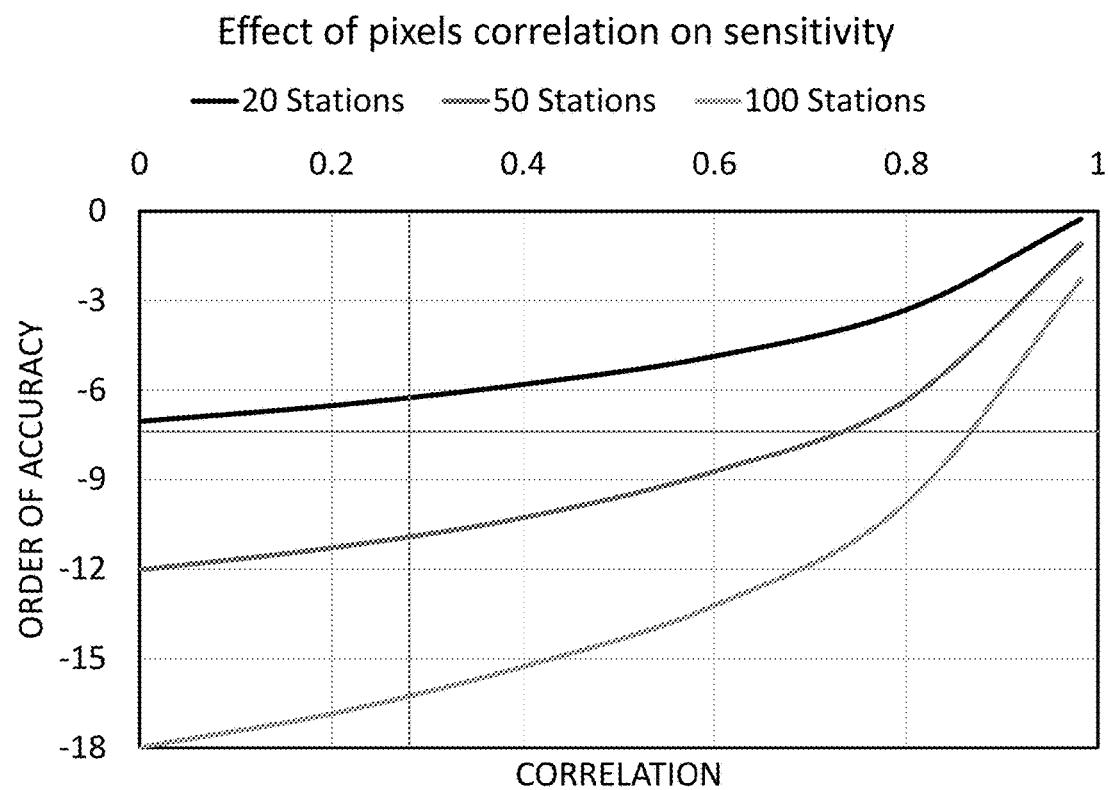
FIG. 9A shows the impact of the correlation between an optical signal collected by two adjacent pixels and sensitivity across 20, 50, and 100 stations, illustrating the effect of independent imaging counts on sensitivity.
Figure 9B:
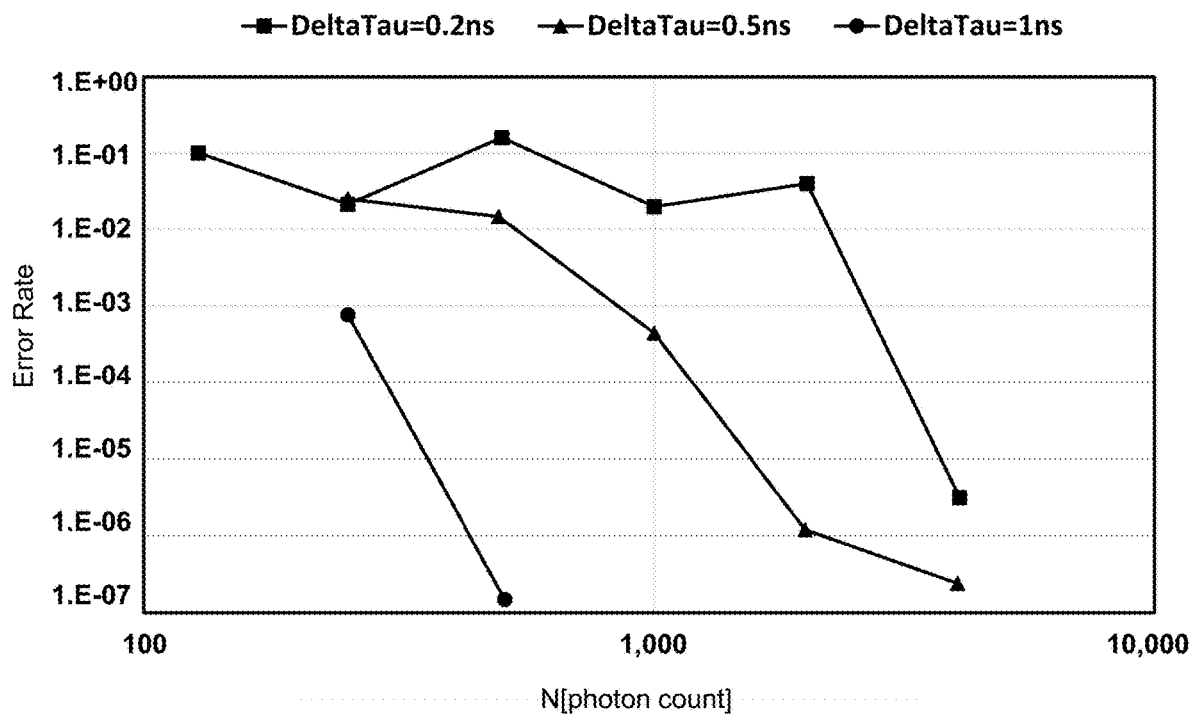
FIG. 9B shows error rate as a function of photon count, for various separation between average lifetimes.

The two solutions of microspheres are separately pumped into a flow channel fabricated with a microfluidic channel and 2-D SPAD array for imaging. For crimson microspheres, the laser source is tuned to a 640 nm peak wavelength, 10 MHz repetition rate and 300 mW peak power (DD-635L, Horiba Scientific, UK). For yellow-green microspheres, the laser is tuned to a 503 nm peak wavelength, 10 MHz repetition rate and 100 mW peak power (DD-510L, Horiba Scientific, UK). A SPAD array is used as the imager and decay is analyzed by time correlated single photon counting via a SPAD array is used to image the decay of the microsphere samples. The sample is inserted via a cell sample cartridge into the microfluidic channel of the analyte processing device. A graph comparing pixel correlation and sensitivity of measurement is shown in FIG. 9A. 20 stations of pixels demonstrate a range of precision at least down to $10^{-6}$ m as shown in FIG. 9A, with a corresponding increase in sensitivity when greater numbers of photodetector pixel stations are correlated. FIG. 10A further demonstrates the signal quality achieved and reduced false positive rate with UTLM.

Example 8

Sorting of a Blood Sample with Device

In order to analyze and sort a population of cells based on size estimation, a sample of dilute whole blood is combined with an equal volume of room temperature PBS. The sample is centrifuged at 400-500×g for 30-40 min at room temperature and is thereafter aspirated to remove granulocytes from peripheral blood mononuclear cells (PBMC). The PBMC sample is re-suspended in PBS and is further centrifuged at 300-400×g for 10 min at room temperature. The cells are then fluorescently tagged with fluoroscein upon resuspension in 1 L PBS buffer. An aliquot of 10 μL is taken and loaded into a cartridge for us with the microfluidic channel described herein. Approximately 5,000 PBMC are loaded into a device comprising a multiplex flow channel comprising a microfluidic channel for imaging via a SPAD array. PBMC are acoustophoresically displaced across a multiplex flow channel microfluidic channel with gates, yielding a sorting of cells per size distribution. FIG. 1F shows a fluidic valve operating as a gate to sort cells based on acquired optical signals.

Example 9

Imaging of Cells and 3-D Morphology Construction

Figure 24:
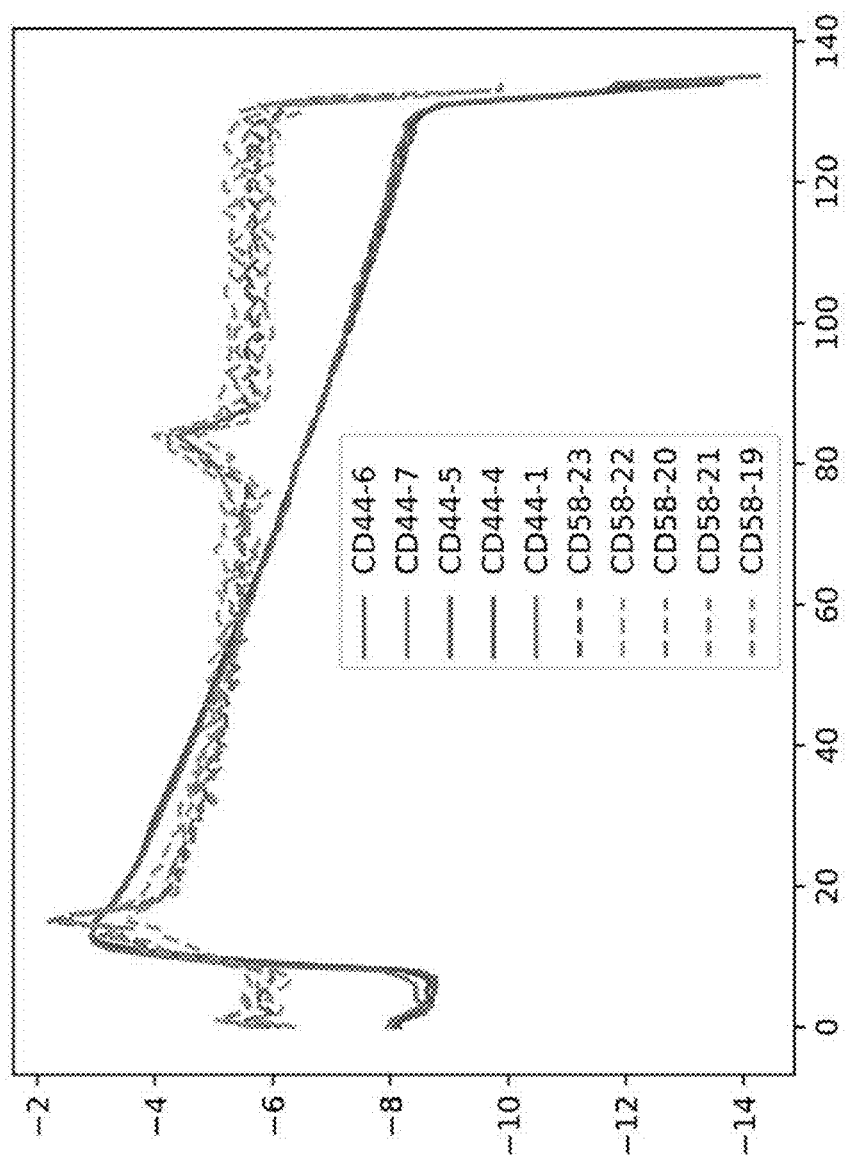
FIG. 24 shows detection mapping of biomarkers via imaging.
Figure 25A:
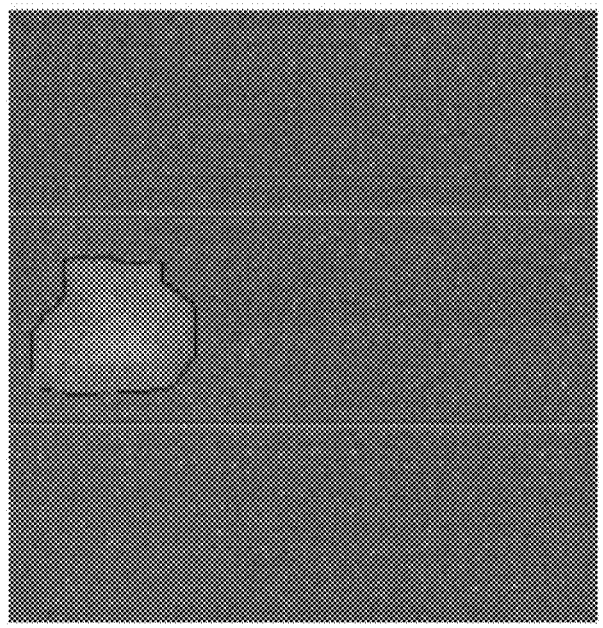
FIG. 25A shows a snapshot of cellular movement within a flow channel of a device described herein.
Figure 25B:
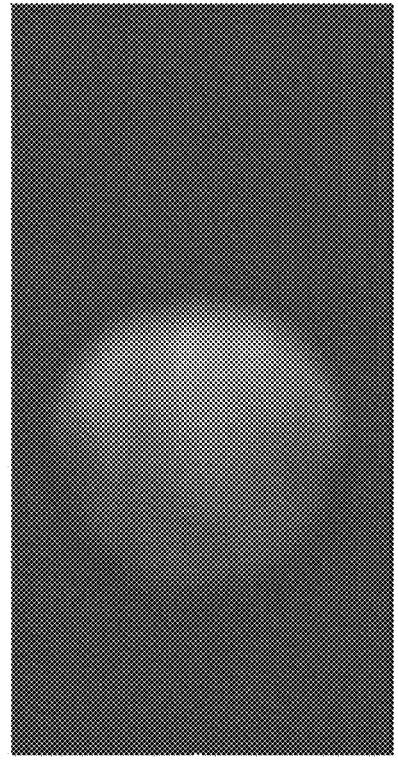
FIG. 25B shows a snapshot of cellular movement within a flow channel of a device described herein.
Figure 26:
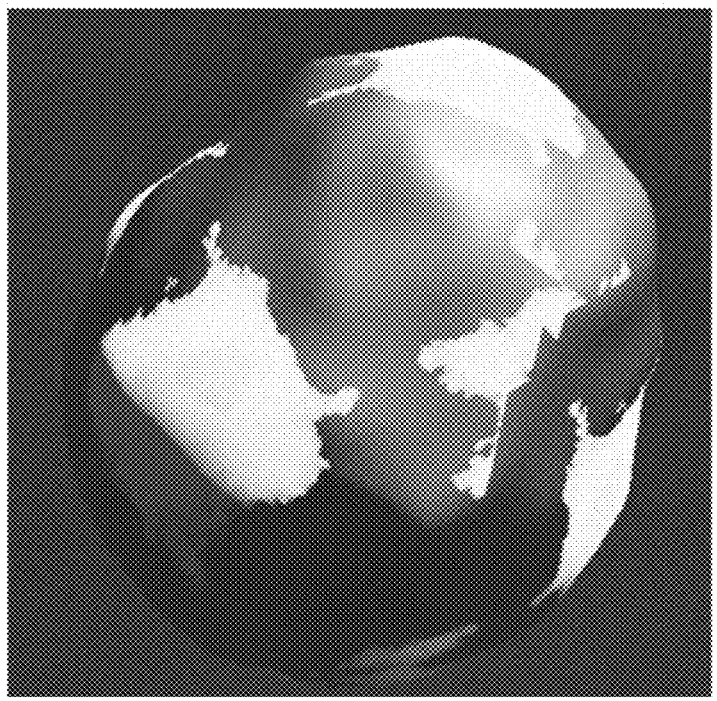
FIG. 26 shows 3-D construction of a cell imaged via a device herein using AI and machine learning.
Figure 27:
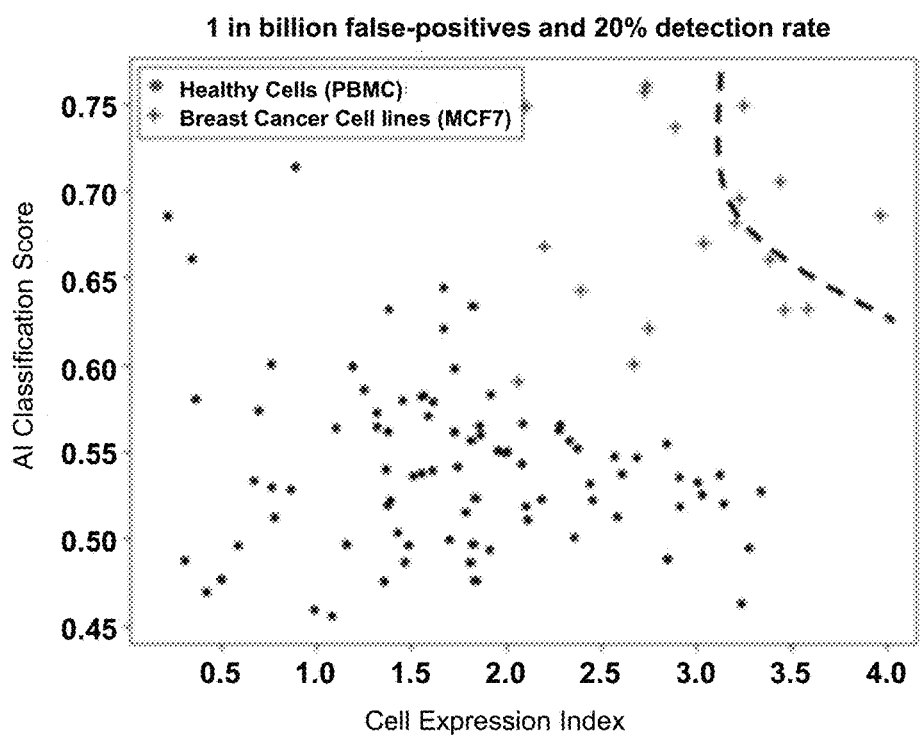
FIG. 27 shows a diagram illustrating cell expression index correlation with AI and machine learning classification.

Cellular imaging and morphological construction were accomplished using a device disclosed herein. FIG. 25A and FIG. 25B shows snapshots from a detection video of a cell moving through a microfluidic channel. With training via the cell markers shown in FIG. 24, a test cell was moved through the analyte processing area. The location of specific biomarkers on the test cell (color not shown) is identified on the cell surface. A 3-D morphological construction is made from the optical signals detected by the device and is visualized in FIG. 26. The construction can be refined further with machine learning algorithms. The accuracy of the device at categorizing healthy PBMC cells and MCF7 breast cancer cells is depicted in FIG. 27. The cell expression index comprises variables related to cellular dye lifetime emission features are detected optically, and the AI classification score enables enhanced detection capabilities towards cancer cell detection. The resulting device has improved imaging capabilities.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A method for determining a location of a cell surface marker on a surface of a cell, the method comprising:
    a. subjecting the cell to flow through a channel;
    b. while the cell is flowing through the channel, exposing the cell to a plurality of diffracted beams generated by diffracting a light from one or more excitation sources using a light diffractive system, wherein upon exposure of the cell to the plurality of diffracted beams, a plurality of photons is emitted from the cell, wherein the light diffractive system comprises a diffractive photonic circuit that causes the light from the one or more excitation sources to diffract into the plurality of diffracted beams that exposes a plurality of spatially separate locations along the channel, thereby exciting the cell M times in one pass of the flowing cell through the channel, wherein an excitation of the cell emits a photon of the plurality of photons;
    c. using a single-photon avalanche diode (SPAD) array disposed in proximity to the channel to detect the plurality of photons; and
    d. processing the plurality of photons detected in (c) to generate a topographic map of the surface of the cell comprising the location of the cell surface marker,
        wherein the SPAD array comprises a plurality of SPADs disposed adjacent to the plurality of spatially separate locations along the channel, and
        wherein the cell enters the channel and iterates through the channel for at least N iterations, thereby generating N*M number of photons.

2. The method of claim 1, wherein the cell is part of a population of cells, and wherein the method further comprises generating a distribution comprising one or more topographic maps of one or more cells of the population of cells.

3. The method of claim 1 further comprising detecting or generating a plurality of two-dimensional images of the cell and using the plurality of two-dimensional images to construct a three-dimensional morphology of the cell.

4. The method of claim 3, wherein the plurality of photons generates the plurality of two-dimensional images at the plurality of spatially separate locations along the channel.

5. The method of claim 1, further comprising pulsing the cell and recording a duration of time between a pulse and detection of a photon of the plurality of photons by the SPAD array, thereby generating a Time of Flight (TOF) of the photon.

6. The method of claim 5, further comprising generating the TOF of the photon repeatedly for the cell at the plurality of spatially separate locations along the channel, thereby generating an array of TOF data for the cell.

7. The method of claim 6, further comprising classifying the cell using the array of TOF data.

8. The method of claim 1, wherein the system comprises T channels, and the method comprises screening C number of cells, wherein a cell of the C number of cells is screened N*M times, and the method comprises detecting N*M*C*T number of photons and generating a composite matrix with C*T sub-matrices, each sub-matrix having the size N*M.

9. The method of claim 8, further comprising classifying the C number of cells using the composite matrix, wherein each sub-matrix is a classification category.

10. The method of claim 1, wherein an orientation of the cell changes during an iteration of the at least N iterations.

11. The method of claim 10, further comprising using an acoustic transducer to change the orientation of the cell in the iteration through the channel.

12. The method of claim 1, wherein the topographic map comprises a location map comprising the cell surface marker, an intensity map comprising the cell surface marker, a density map comprising the cell surface marker, or any combination thereof.

13. The method of claim 1, wherein the topographic map comprises an atlas of cellular expression comprising the cell surface marker.

14. The method of claim 1, wherein M is at least two.

15. The method of claim 14, wherein (c) comprises detections of the at least two M excitations.

16. The method of claim 1, further comprising performing (a)-(d) on a second cell in a second channel.

17. The method of claim 16, wherein performing (a)-(d) on the second cell in the second channel occurs simultaneously with performing (a)-(d) on the cell in the channel.

18. The method of claim 1, further comprising classifying a phenotype of the cell.

19. The method of claim 1, wherein the plurality of photons comprise fluorescent photons and the detection of the plurality of photons comprises fluorescent detection.

* * * * *